United States Patent
Wu et al.

(10) Patent No.: US 11,040,968 B2
(45) Date of Patent: Jun. 22, 2021

(54) PYRIDINE DERIVATIVE AS ASK1 INHIBITOR AND PREPARATION METHOD AND USE THEREOF

(71) Applicant: FUJIAN COSUNTER PHARMACEUTICAL CO., LTD., Fujian (CN)

(72) Inventors: Chengde Wu, Shanghai (CN); Tao Yu, Shanghai (CN); Ning Li, Shanghai (CN); Shuhui Chen, Shanghai (CN)

( * ) Notice: Subject to any disclaimer, the term of this patent is extended or adjusted under 35 U.S.C. 154(b) by 52 days.

(21) Appl. No.: 16/478,132

(22) PCT Filed: Jan. 22, 2018

(86) PCT No.: PCT/CN2018/073640
§ 371 (c)(1),
(2) Date: Jul. 16, 2019

(87) PCT Pub. No.: WO2018/133866
PCT Pub. Date: Jul. 26, 2018

(65) Prior Publication Data
US 2020/0031823 A1    Jan. 30, 2020

(30) Foreign Application Priority Data

Jan. 22, 2017 (CN) .......................... 201710054224.4

(51) Int. Cl.
*C07D 471/04* (2006.01)
(52) U.S. Cl.
CPC ................... *C07D 471/04* (2013.01)
(58) Field of Classification Search
CPC .. C07D 471/04; C07D 255/04; C07D 213/89; A61K 31/4353; A61K 31/4439; A61K 31/444
See application file for complete search history.

(56) References Cited

U.S. PATENT DOCUMENTS

| 8,378,108 B2 * | 2/2013 | Corkey | C07D 471/04 |
| | | | 546/256 |
| 9,067,933 B2 * | 6/2015 | Corkey | A61K 31/585 |
| 2011/0009410 A1 | 1/2011 | Corkey et al. | |

FOREIGN PATENT DOCUMENTS

| CN | 102482257 A | 5/2012 |
| CN | 104080771 A | 10/2014 |
| KR | 10-2012-0034735 A | 4/2012 |
| WO | 2011008709 A | 1/2011 |
| WO | 2013112741 A | 8/2013 |

OTHER PUBLICATIONS

International Search Report and Written Opinion of PCT/CN2018/073640 dated May 2, 2018.
Extended European Search Report issued in counterpart European patent application No. 18741136.8 dated Sep. 23, 2019.
First Office Action and Search Report issued in counterpart Chinese patent application No. 201880001401.5 dated May 17, 2019.
Sergiy A. Starosyla et al., "ASK1 pharmacophore model derived from diverse classes of inhibitors", Bioorganic & Medicinal Chemistry Letters, vol. 24, No. 18, 2014, pp. 4418-4423.
Office Action issued in the counterpart Korean application No. 10-2019-7022629 dated Nov. 20, 2019.
Office Action issued in the counterpart Canadian application No. 3,050,346 dated Dec. 5, 2019.
Nagai H et al, J Biochem Mol Biol, 2007, 40(1), 1-6.
Soga M et al, Int J Cell Biol, 2012, 2012, 439587.
Mar. 5, 2021 The First Examination Report issued in India Patent Application No. 201917028619.

* cited by examiner

*Primary Examiner* — D Margaret M Seaman
(74) *Attorney, Agent, or Firm* — Houston Beshining Law Office PLLC; Liangang Ye

(57) ABSTRACT

Disclosed in the present invention are a compound as shown in formula (II), a tautomer or a pharmaceutically acceptable salt thereof, and also disclosed is the use thereof in preparing a drug for treating an ASK1-associated disease.

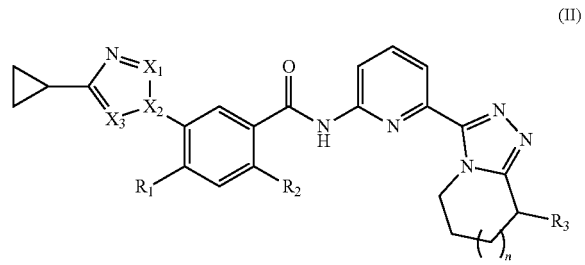

(II)

18 Claims, No Drawings

PYRIDINE DERIVATIVE AS ASK1 INHIBITOR AND PREPARATION METHOD AND USE THEREOF

CROSS REFERENCE TO RELATED APPLICATION

The present application is a National Stage of International Application No. PCT/CN2018/073640, filed on Jan. 22, 2018, which claims the priority of the Chinese Patent Application No. CN201710054224.4 filed on Jan. 22, 2017, the contents of which are incorporated herein in the present application.

FIELD OF INVENTION

The present invention relates to a compound as shown in formula (II), a tautomer thereof or a pharmaceutically acceptable salt thereof, and a use thereof in manufacturing a medicament for treating ASK1-related diseases.

PRIOR ARTS

Apoptosis signal-regulating kinase 1 (ASK1) is a member of the mitogen-activated protein kinase kinase kinase (MAP3K) family. ASK1 can be activated by a variety of stimuli including oxidative stress, reactive oxygen species (ROS), LPS, TNF-α, FasL, endoplasmic reticulum stress, increased intracellular calcium concentration and the like. ASK1 responds to the variety of stimuli by activating JNK (c-Jun N-terminal kinase) and p38 mitogen-activated protein kinases, and induces a variety of apoptosis through the signals involving the mitochondrial cell death pathway. The activation and the signaling of ASK1 play an important role in a broad range of diseases, including neurodegenerative diseases, cardiovascular diseases, inflammatory diseases, autoimmune diseases, and metabolic disorders. Therefore, when the patient suffers from a neurodegenerative disease, a cardiovascular disease, an inflammation, an autoimmune disease, and a metabolic disease, the life of the patient can be improved by the use of the ASK1 inhibitors as therapeutic agents.

CONTENT OF THE PRESENT INVENTION

The present invention provides a compound as shown in formula (II), a pharmaceutically acceptable salt thereof and a tautomer thereof,

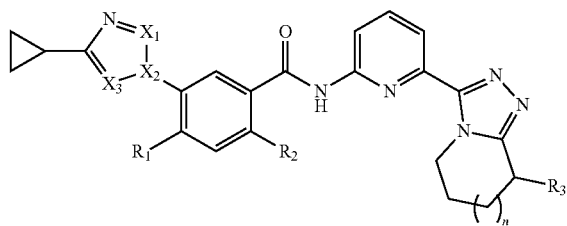

(II)

at least one of $X_1$, $X_2$ and $X_3$ is N, the rest of which is CH;
n is selected from 0 or 1;
$R_1$ is selected from H, F, Cl, Br, I, OH, $NH_2$, or selected from the group consisting of $C_{1-4}$ alkyl, $C_{1-4}$ heteroalkyl, 3-6 membered heterocycloalkyl and 5-6 membered heteroaryl, each of which is optionally substituted by R;
$R_2$ is selected from H, F, Cl, Br, I;
$R_3$ is selected from H, F, Cl, Br, I, OH, $NH_2$;
R is selected from F, Cl, Br, I, OH, $NH_2$, or selected from the group consisting of $C_{1-3}$ alkyl, $C_{1-3}$ alkoxy and 3-6 membered heterocycloalkyl, each of which is optionally substituted by 1, 2 or 3 R;
R' is selected from the group consisting of F, Cl, Br, I, OH, $NH_2$ and $C_{1-3}$ alkyl;
each of the "hetero" in the $C_{1-4}$ heteroalkyl, 5-6 membered heteroaryl and 3-6 membered heterocycloalkyl is independently selected from the group consisting of -NH-, N, -O-, and -S-;
in any of the above cases, the number of the heteroatom or the heteroatomic group is independently selected from 1, 2 or 3.

In some embodiments of the present invention, the above R is selected from F, Cl, Br, I, OH, $NH_2$, or selected from the group consisting of Me,

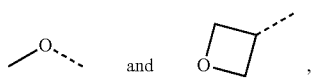

each of which is optionally substituted by 1, 2 or 3 R';

In some embodiments of the present invention, the above R is selected from the group consisting of F, Cl, Br, I, OH, $NH_2$, Me,

In some embodiments of the present invention, the above $R_1$ is selected from H, F, Cl, Br, I, OH, $NH_2$, or selected from the group consisting of $C_{1-3}$ alkyl, $C_{1-3}$ alkoxy, $C_{1-3}$ alkylamino, morpholinyl and pyridyl, each of which is optionally substituted by 1, 2 or 3 R, and other variables are as defined in the present invention.

In some embodiments of the present invention, the above $R_1$ is selected from H, F, Cl, Br, I, OH, $NH_2$, or selected from the group consisting of Me,

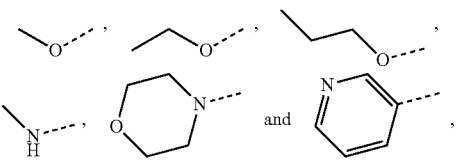

each of which is optionally substituted by 1, 2 or 3 R, and other variables are as defined in the present invention.

In some embodiments of the present invention, the above $R_1$ is selected from the group consisting of H, F, Cl, Br, I, OH, $NH_2$, Me,

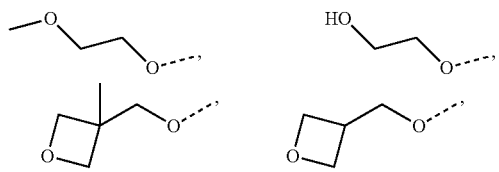

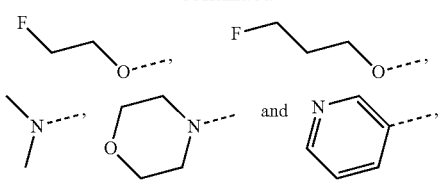

and other variables are as defined in the present invention.

In some embodiments of the present invention, the above moiety

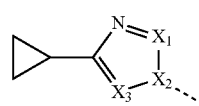

is selected from the group consisting of

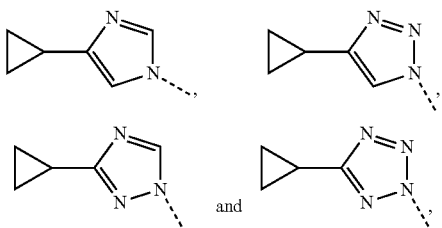

and other variables are as defined in the present invention.

In some embodiments of the present invention, the above moiety

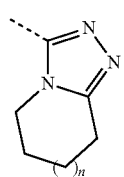

is selected from the group consisting of

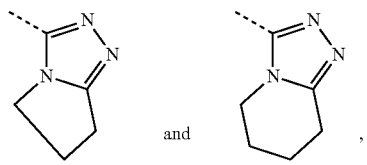

and other variables are as defined in the present invention.

Other embodiments of the present invention can be obtained by the arbitrary combination of the above variables.

In some embodiments of the present invention, the above compound, the pharmaceutically acceptable salt thereof and the tautomer thereof is selected from the group consisting of

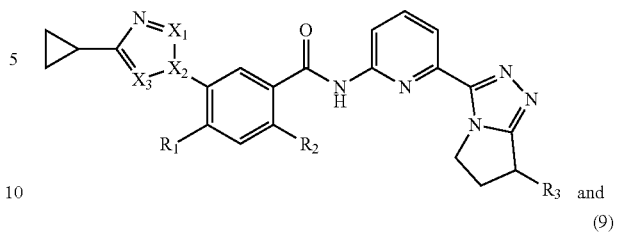

(8)

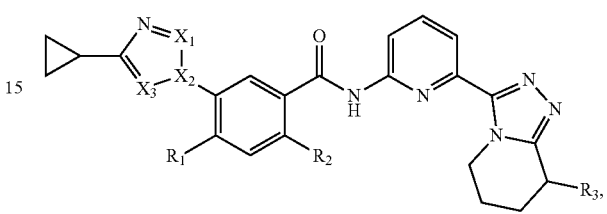

(9)

wherein, $X_1$, $X_2$, $X_3$, $R_1$, $R_2$ and $R_3$ are as defined in the present invention.

In some embodiments of the present invention, the above compound, the pharmaceutically acceptable salt thereof and the tautomer thereof is selected from the group consisting of

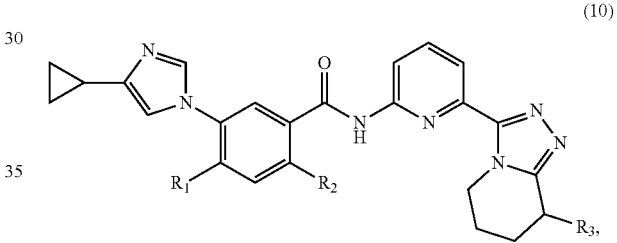

(10)

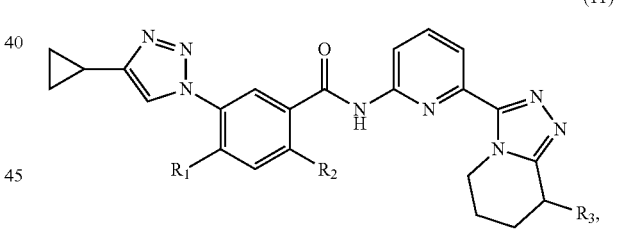

(11)

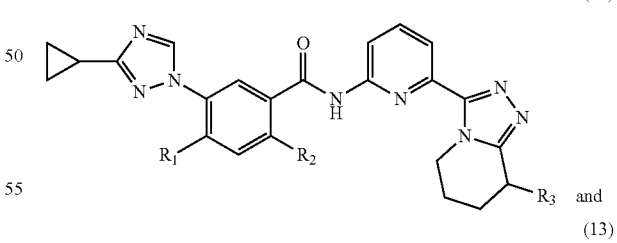

(12)

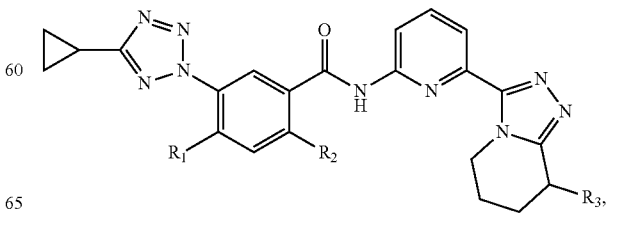

(13)

wherein,
R₁, R₂ and R₃ are as defined in the present invention.

The present invention also provides a compound as shown in formula (I), a pharmaceutically acceptable salt thereof and a tautomer thereof:

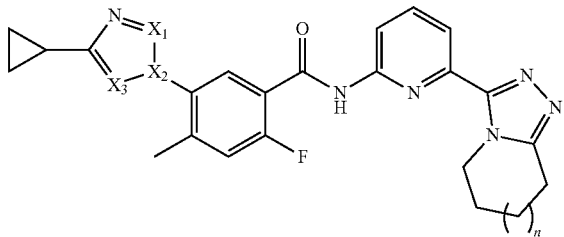
(I)

at least one of X₁, X₂ and X₃ is N, the rest of which is CH;
n is 0 or 1;

In some embodiments of the present invention, the above moiety

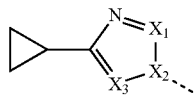

is selected from the group consisting of

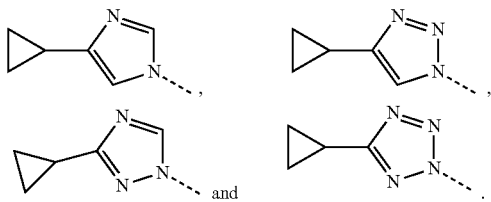

In some embodiments of the present invention, the above moiety

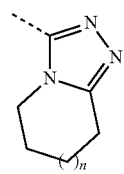

is selected from the group consisting of

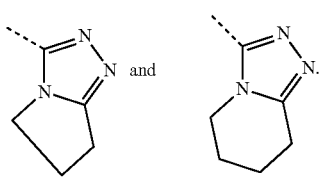

In some embodiments of the present invention, the above moiety

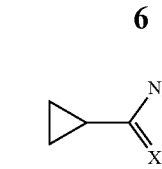

is selected from the group consisting of

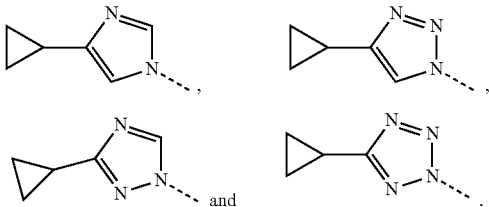

and other variables are as defined in the present invention.

In some embodiments of the present invention, the above moiety

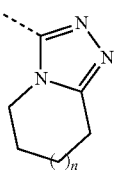

is selected from the group consisting of

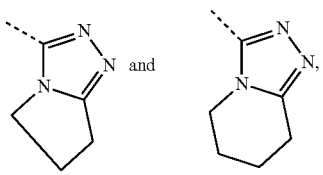

and other variables are as defined in the present invention.

Other embodiments of the present invention can be obtained by the arbitrary combination of the above variables.

In some embodiments of the present invention, the above compound, the pharmaceutically acceptable salt thereof and the tautomer thereof is selected from the group consisting of

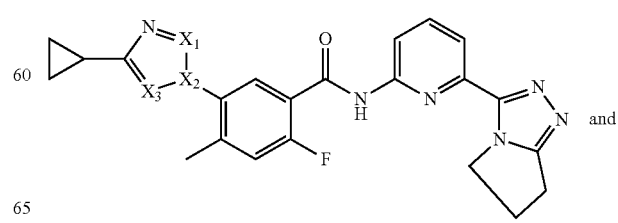
(2)

-continued (3)

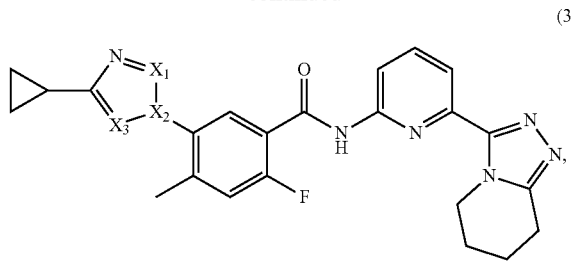

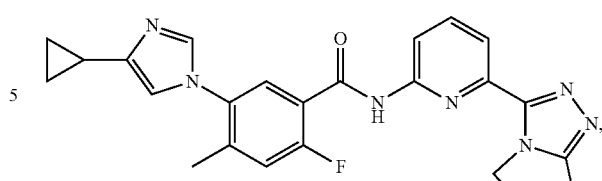

wherein, $X_1$, $X_2$ and $X_3$ are as defined in the present invention.

In some embodiments of the present invention, the above compound, the pharmaceutically acceptable salt thereof and the tautomer thereof is selected from the group consisting of

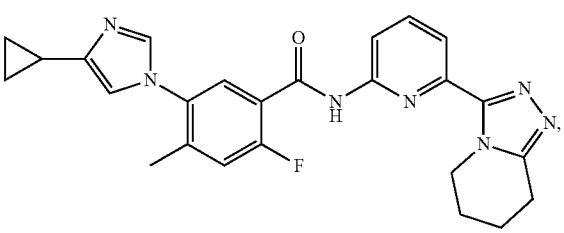

(4)

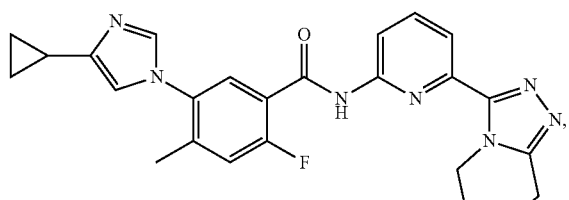

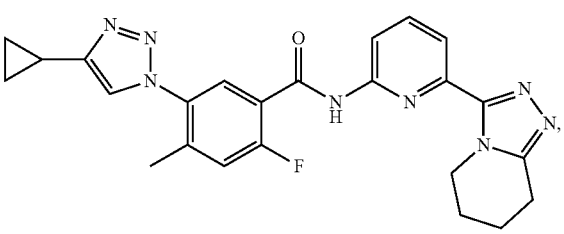

(5)

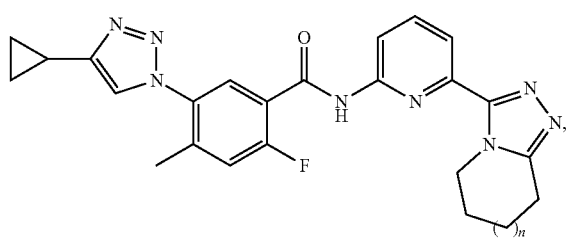

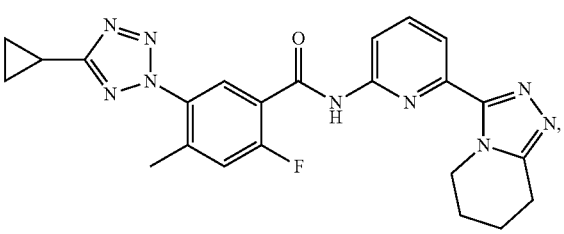

(6)

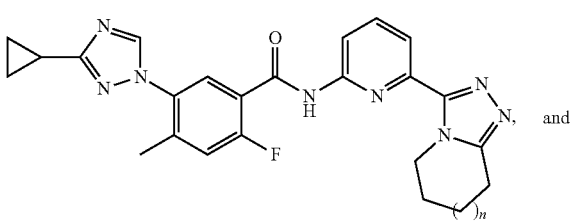

and

(7)

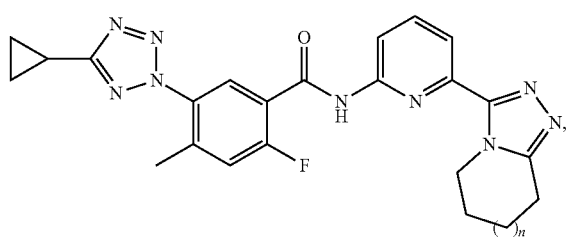

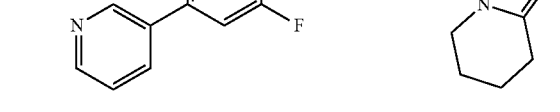

wherein, n is as defined in the present invention.

The present invention also provides a compound, a pharmaceutically acceptable salt thereof and a tautomer thereof which is selected from the group consisting of

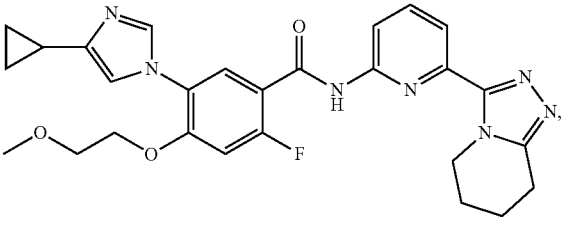

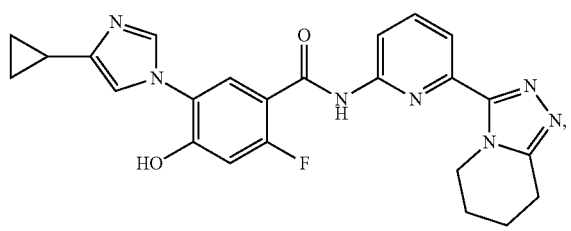
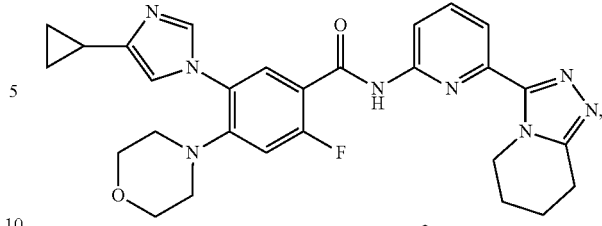

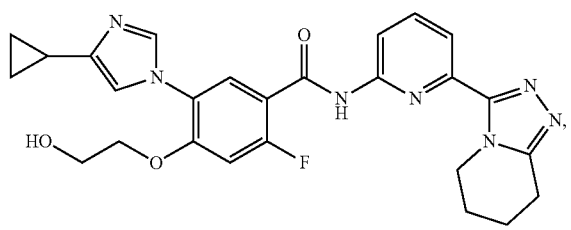
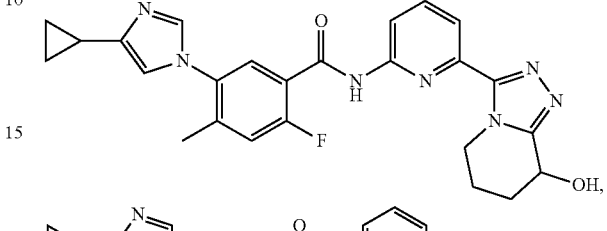

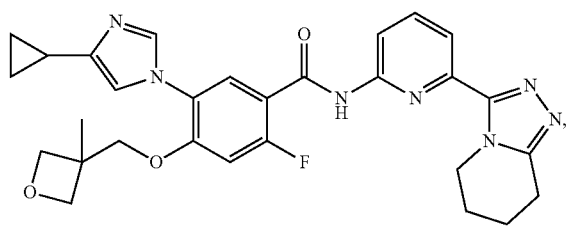
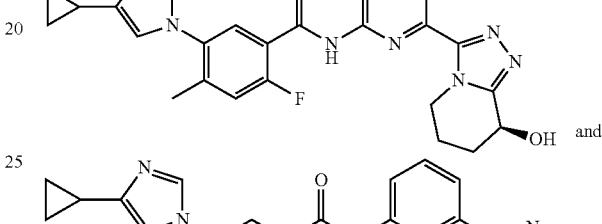

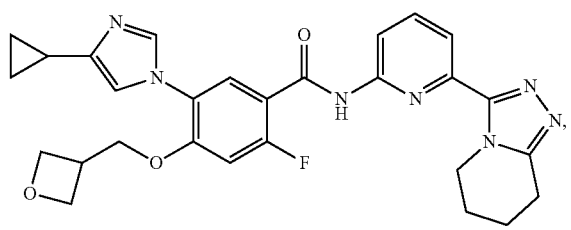
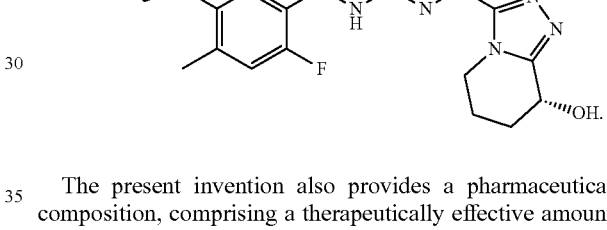

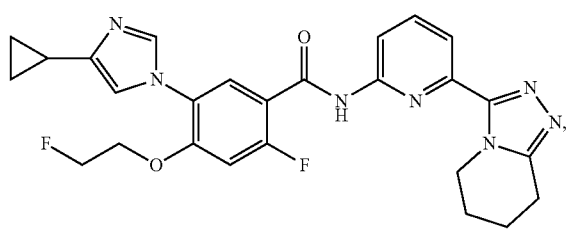

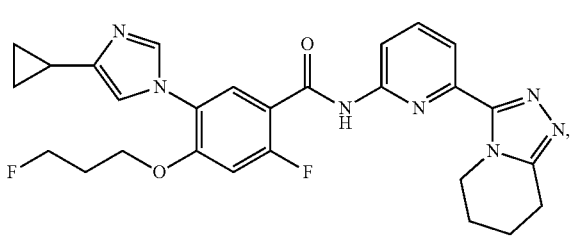

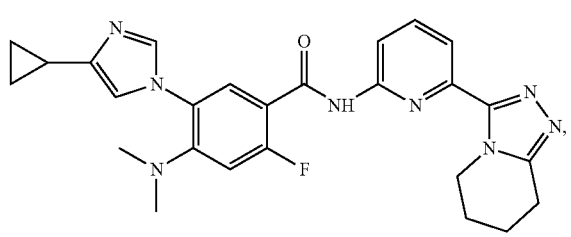

The present invention also provides a pharmaceutical composition, comprising a therapeutically effective amount of the above compound or the pharmaceutically acceptable salt thereof as the active ingredient, and a pharmaceutically acceptable carrier.

The present invention also provides a use of the above compound or the pharmaceutically acceptable salt thereof in manufacturing a medicament for treating ASK1-related diseases.

The present invention also provides a use of the above composition in manufacturing a medicament for treating ASK1-related diseases.

Technical Effect

As a novel ASK1 inhibitor, the compound of the present invention has a significant inhibitory effect against ASK1. Meanwhile, the compound of the present invention has a good druggability due to its good solubility, permeability, and the like, specific targeting, and metabolic stability.

Definition and Description

Unless otherwise indicated, the following terms when used in the descriptions and the claims of the present invention have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present invention that is prepared by reacting the compound having a specific substituent of the present invention with a relatively non-toxic acid or base. When the compound of the present invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (refer to Berge et al., "*Pharmaceutical Salts*", *Journal of Pharmaceutical Science* 66: 1-19 (1977)). Certain specific compounds of the present invention that contain both basic and acidic functional groups can be converted to any base or acid addition salt.

Preferably, through bringing the salt into contact with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound of the present invention, wherein, the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt of the present invention can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided by the present invention also exists in prodrug form. The prodrug of the compound described herein is the compound that readily undergoes chemical change under physiological condition to be converted into the compound of the present invention. Additionally, the prodrug can be converted to the compound of the present invention by a chemical or biochemical method in vivo environment.

Certain compounds of the present invention can exist in a nonsolvated form or a solvated form, including hydrated form. Generally, the solvated form is equivalent to the nonsolvated form, and both are encompassed within the scope of the present invention.

Certain compounds of the present invention can have an asymmetric carbon atom (optical center) or a double bond. The racemate, diastereomer, geometric isomer and single isomer are all encompassed within the scope of the present invention.

Unless otherwise specified, the absolute configuration of a stereogenic center is represented by a wedged solid bond (▰) and a wedged dashed bond (⋯), a wave line (∿) represents a wedged solid bond (▰) or a wedged dashed bond (⋯), and the relative configuration of a stereogenic center is represented by a straight solid bond (▰) and a straight dashed bond (⋯). When the compound described herein contains an olefinic double bond or other geometric asymmetric centers, E and Z geometric isomers are included unless otherwise specified. Likewise, all tautomeric forms are encompassed within the scope of the present invention.

The compound of the present invention may have a specific geometric or stereoisomeric form. The present invention contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present invention. The substituent such as alkyl may have an additional asymmetric carbon atom. All these isomers and mixtures thereof are encompassed within the scope of the present invention.

Optically active (R)- and (S)-isomer, or D and L isomer can be prepared using chiral synthesis or chiral reagents or other conventional techniques. If one kind of enantiomer of certain compound of the present invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine).

The compound of the present invention may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). All isotopic variations of the compound of the present invention, whether radioactive or not, are encompassed within the scope of the present invention.

The term "pharmaceutically acceptable carrier" refers to any agent or carrier medium which is capable of delivering an effective amount of the active substance of the present invention, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field. The additional information about the carrier can be referred to *Remington: The Science and Practice of Pharmacy,* 21st Ed., Lippincott, Williams & Wilkins (2005), the contents of which are incorporated herein by reference.

The term "excipient" generally refers to the carrier, diluent and/or vehicle required to formulate an effective pharmaceutical composition.

For a medicament or a pharmacologically active agent, the term "effective amount" or "therapeutically effective amount" refers to a nontoxic but sufficient amount to achieve a desired effect of the medicament or the agent. For the oral dosage form of the present invention, an "effective amount" of the active substance in the composition refers to an amount required for achieving a desired effect when combining with another active substance in the composition. The effective amount varies from person to person and is determined depending on the age and general condition of the recipient as well as the specific active substance. The appropriate effective amount in an individual case can be determined by the skilled in the art based on routine experiment.

The term "active ingredient", "therapeutic agent", "active substance" or "active agent" refers to a chemical entity which can effectively treat the target disorder, disease or condition.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as -(CRR)$_0$-, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a bond of a substituent can be cross-linked to more than one atom on a ring, such substituent can be bonded to any atom of the ring. For example, the structural unit

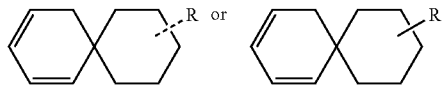

means that the substituent R can be located at any position on cyclohexyl or cyclohexadiene. When an enumerative substituent does not indicate by which atom it is attached to a compound included in the general chemical formula but not specifically mentioned, such substituent can be bonded by any of its atoms. For example, the pyridinyl as a substituent can be attached to the substituted group by any carbon atoms on the pyridine ring. When the enumerative linking group does not indicate the direction for linking, the direction for linking is arbitrary, for example, the linking group L contained in

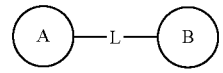

is -MW-, then -MW- can link ring A and ring B to form

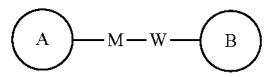

in the direction same as left-to-right reading order, and form

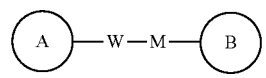

in the direction contrary to left-to-right reading order. A combination of linking group, substituents and/or variants thereof is allowed only when such combination can result in a stable compound.

Unless otherwise specified, the term "hetero" represents a heteroatom or a heteroatomic group (e.g., an atom group containing a heteroatom), including the atom except carbon (C) and hydrogen (H) and the atom group containing the above heteroatom, for example, including oxygen (O), nitrogen (N), sulfur (S), silicon (Si), germanium (Ge), aluminum (Al), boron (B), -O- , -S-, =O, =S, -C(=O)O-, -C(=O)-, -C(=S)-, -S(=O), -S(=O)$_2$-, and the group consisting of -C(=O)N(H)-, -C(=NH)-, -S(=O)$_2$N(H)- and -S(=O)N(H)-, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a link ring, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclo" refers to a stable monocyclic, bicyclic or tricyclic ring containing a heteroatom or a heteroatomic group, which can be saturated, partially unsaturated or unsaturated (aromatic) and can contain carbon atoms and 1, 2, 3 or 4 ring heteroatoms independently selected from the group consisting of N, O and S, wherein any of the above heterocycle can be fused to a benzene ring to form a bicyclic ring. Nitrogen and sulfur heteroatoms can optionally be oxidized (i.e., NO and S(O)p, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O)$_p$, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1,2,3-triazolyl, 1,2,4-triazolyl, 1,2,5-triazolyl, 1,3,4-triazolyl and xanthenyl. Also included are fused-ring compounds and spiro compounds.

Unless otherwise specified, the term "hydrocarbyl" or its hyponyms (e.g., alkyl, alkenyl, alkynyl, and aryl, etc.), by itself or as part of another substituent, refers to a linear, branched chain or cyclic hydrocarbon radical or any combination thereof. They can be fully saturated (e.g., alkyl), mono- or polyunsaturated (e.g., alkenyl, alkynyl, and aryl), can be mono- or poly-substituted, can be monovalent (e.g., methyl), divalent (e.g., methylene) or multivalent (e.g., methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from the group consisting of B, O, N and S, wherein nitrogen and sulfur atoms are optionally oxidized and the nitrogen atom is optionally quaternized. The heteroatom or heteroatomic group can be located at any interior position of a heterohydrocarbyl, including the position where the hydrocarbyl attaches to the rest part of the molecule. But the terms "alkoxy", "alkylamino" and "alkylthio" (or thioalkoxyl) are used by the conventional meaning and refer to an alkyl group connected to the rest part of the molecule via an oxygen atom, an amino or a sulfur atom respectively. Examples include, but are not limited to, -CH$_2$-CH$_2$-O-CH$_3$, -CH$_2$-CH$_2$-NH-CH$_3$, -CH$_2$-CH$_2$-N(CH$_3$)-CH$_3$, -CH$_2$-S-CH$_2$-CH$_3$, -CH$_2$-CH$_2$, -S(O)-CH$_3$, -CH$_2$-CH$_2$-S(O)$_2$-CH$_3$, -CH=CH-O-CH$_3$, -CH$_2$-CH=N-OCH$_3$ and -CH=CH-N(CH$_3$)-CH$_3$. Up to two consecutive heteroatoms can be present, such as, -CH$_2$-NH-OCH$_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g., heteroalkyl, and heterocycloalkyl), one heteroatom can occupy the position where the heterocycle attaches to the remainder position of the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbon group, can be mono-substituted (e.g., -CH$_2$F) or poly-substituted (e.g., -CF$_3$), can be monovalent (e.g. methyl), divalent (e.g., methylene) or multivalent (e.g., methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be monosubstituted or poly-substituted, and can be monovalent, divalent or multivalent. Examples of alkynyl include ethynyl, propynyl, butynyl, pentynyl, and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, bicyclooctane, [4.4.0]bicyclodecanyl and the like.

Unless otherwise specified, cycloalkenyl includes any stable cyclic or polycyclic hydrocarbyl having one or more than one unsaturated carbon-carbon single bonds at any position on the ring, can be mono-substituted or polysubstituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo(C$_1$-C$_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, C$_{1-6}$ alkoxy includes C$_1$, C$_2$, C$_3$, C$_4$, C$_5$ and C$_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from the group consisting of B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyloxazolyl, isoxazolyl, thiazolyl, furanyl, thienyl, pyridyl, pyrimidinyl benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when aryl combines with other terms (such as aryloxy, arylthio, arylalkyl), the aryl includes the aryl and heteroaryl ring as defined above. Thus, the term "aralkyl" is meant to include the group (e.g., benzyl, phenethyl, pyridylmethyl, etc.) where an aryl is attached to an alkyl, including an alkyl where the carbon atom (e.g., methylene) has been replaced by an atom such as oxygen, for example, phenoxymethyl, 2-pyridyloxy, 3-(1-naphthyloxy)propyl, and the like.

The term "leaving group" refers to a functional group or atom which can be replaced by another functional group or atom through a substitution reaction (such as nucleophilic substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl)methyl; silyl such as trimethylsilyl (TMS) and tert-butyldimethylsilyl (TBS) and the like. The term "hydroxy protecting group" refers to a protecting group suitable for blocking the side reaction on hydroxy.

Representative hydroxy protecting groups include, but are not limited to: alkyl such as methyl, ethyl and tert-butyl; acyl such as alkanoyl (e.g., acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the present invention can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present invention.

All of the solvents used in the present invention are commercially available. This present invention adopts the abbreviating words as followed: "Aq" refers to water; "HATU" refers to O-(7-azabenzotriazol-1-yl)-N,N,N',N'-tetramethyluronium hexafluorophosphate; "EDC" refers to N-(3-dimethylaminopropyl)-N'-ethylcarbodiimide hydrochloride; "m-CPBA" refers to 3-chloroperoxybenzoic acid; "eq" refers to equivalent; "CDI" refers to carbonyldiimidazole; "DCM" refers to dichloromethane; "PE" refers to petroleum ether; "DIAD" refers to diisopropyl azodicarboxylate; "DMF" refers to N,N-dimethylformamide; "DMSO" refers to dimethyl sulfoxide; "EtOAc" refers to ethyl acetate; "EtOH" refers to ethanol; "MeOH" refers to methanol; "CBz" refers to benzyloxycarbonyl, which is a protecting group for amines; "BOC" refers to t-butylcarbonyl which is a protecting group for amines; "HOAc" refers to acetic acid; "NaCNBH$_3$" refers to sodium cyanoborohydride; r.t. refers to room temperature; "O/N" refers to overnight; "THF" refers to tetrahydrofuran; "Boc$_2$O" refers to di-tert-butyldicarbonate; "TFA" refers to trifluoroacetic acid; "DIPEA" refers to diisopropylethylamine; "SOCl$_2$" refers to thionyl chloride; "CS$_2$" refers to carbon disulfide; "TsOH" refers to p-toluenesulfonic acid; "NFSI" refers to N-fluoro-N-(phenylsulfonyl)benzenesulfonamide; "NCS" refers to 1-chloropyrrolidine-2,5-dione; "n-Bu$_4$NF" refers to tetrabutylammonium fluoride; "iPrOH" refers to 2-propyl;

"mp" refers to melting point; "LDA" refers to diisopropylamino lithium; "DMP" refers to dimethyl phthalate; "Xantphos" refers to 4,5-bisdiphenylphosphino-9,9-dimethyloxaxime; "Pd$_2$(dba)$_3$" refers to tris(dibenzylideneacetone) dipalladium; "Xant-Phos" refers to 4,5-bisdiphenylphosphino-9,9-dimethyloxaxan; "EGTA" refers to ethylene glycol tetraacetic acid; "DIEA" refers to N,N-diisopropylethylamine; "Xantphos" refers to 4,5-bisdiphenylphosphino-9,9-dimethyloxaxan; "AIBN" refers to 2,2'-azobis(2-methylpropionitrile); "Pd$_2$(dba)$_3$" refers to tris (dibenzylideneacetone)dipalladium; "Pd(dppf)Cl$_2$" refers to [1,1'-bis(diphenylphosphino)ferrocene]palladium dichloride; "BnBr" refers to benzyl bromide; "DMAP" refers to 4-dimethylaminopyridine; "EGTA" refers to ethylene glycol tetraacetic acid; "TMSN$_3$" refers to azidotrimethylsilane; "(Bpin)$_2$" refers to bis(pinacolato)diboron; "BnBr" refers to benzyl bromide; "Tf$_2$O" refers to trifluoromethanesulfonic anhydride; trifluoromethanesulfonic anhydride; "Hepes" refers to 4-hydroxyethylpiperazineethanesulfonic acid; "EGTA" refers to ethylene glycol tetraacetic acid.

Compounds are named manually or by ChemDraw® software, the commercially available compounds use their vendor directory names.

DETAILED DESCRIPTION OF THE PREFERRED EMBODIMENT

The following examples further illustrate the present invention, but by all means the invention is not limited thereto. While the present invention has been described in detail and with reference to specific embodiments thereof, it will be apparent to those skilled in the art that various changes and modifications can be made therein without departing from the spirit and scope thereof.

Fragment WXBB-1:

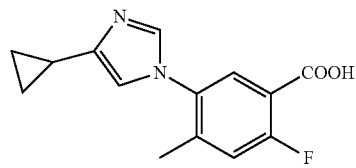 [SMILES: Cc1cc(F)c(C(=O)O)cc1-n1cnc(C2CC2)c1]

Synthetic Route:

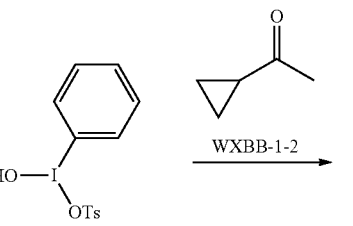

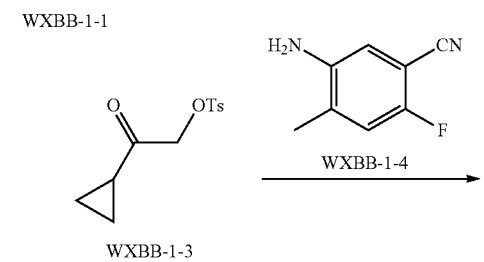

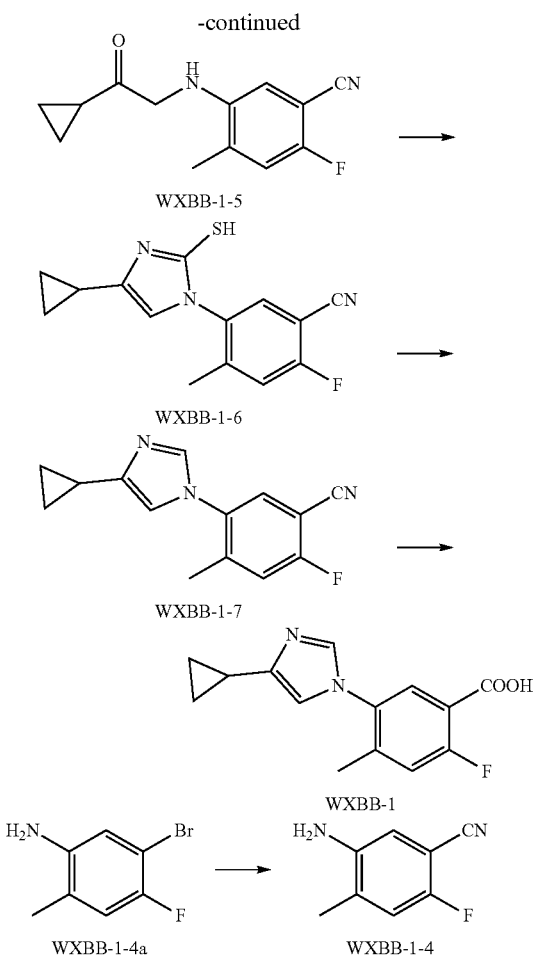

Step 1: Synthesis of Compound WXBB-1-3

WXBB-1-1 (50.00 g, 127.48 mmol, 1.00 eq) was dissolved in acetonitrile (500.00 mL) followed by addition of WXBB-1-2 (12.87 g, 152.98 mmol, 15.14 mL, 1.20 eq). The reaction was carried out at 70° C. for 2 hours under nitrogen atmosphere. After completion of the reaction, the reaction solution was cooled to room temperature, rotary evaporated to dry by water pump under reduced pressure at 40° C., and then dissolved in dichloromethane (150 mL). After washing with water (75 mL*2), the organic phase was concentrated to about 90 mL, and then 75 mL*3 of n-hexane (removing residual dichloromethane) was added and rotary evaporated to give a white solid in the organic phase. The white solid was filtered, and the filter cake was washed with 180 mL of n-hexane and the filter cake was rotary evaporated to dry under reduced pressure to give WXBB-1-3 (27.00 g, 106.17 mmol, 83.29% yield) as a white solid. $^1$H NMR (400 MHz, DMSO-$d_6$) δ ppm 0.79-0.86 (m, 2H) 0.88-0.97 (m, 2H) 1.99-2.10 (m, 1H) 2.42 (s, 3H) 4.98 (s, 2H) 7.49 (d, J=8.16 Hz, 2H) 7.82 (d, J=8.28 Hz, 2H), m/z=255.1 (M+1).

Step 2: Synthesis of Compound WXBB-1-4

WXBB-1-4a (20.00 g, 98.02 mmol, 1.00 eq) was dissolved in N-methylpyrrolidone (100.00 mL), followed by addition of cuprous cyanide (17.56 g, 196.04 mmol, 42.83 mL, 2.00 eq). The reaction was carried out at 180° C. for 3 hours. The reaction solution was cooled to room temperature, followed by addition of water (300 mL) and ammonia (300 mL), stirred at room temperature for 30 minutes, and extracted with ethyl acetate (200 mL*3). The organic phase was washed with saturated brine (200 mL) and water (200 mL), dried over anhydrous sodium sulfate, suction-filtered and rotary evaporated to dry under reduced pressure to give a crude product as a brown-black solid. The crude product was isolated by silica gel column chromatography (PE:EA=20:1-3:1) to give WXBB-1-4 (12.00 g, 79.92 mmol, 81.53% yield) as a yellow solid. $^1$H NMR (400 MHz, CHLOROFORM-d) δ ppm 2.21 (s, 3H) 3.68 (br s, 2H) 6.80 (d, J=5.40 Hz, 1H) 6.91 (d, J=9.29 Hz, 1H).

Step 3: Synthesis of Compound WXBB-1-5

WXBB-1-3 (6.00 g, 39.96 mmol, 1.00 eq), WXBB-1-4 were added into a single-necked flask, followed by addition of diisopropylethylamine (10.85 g, 83.92 mmol, 14.66 mL, 2.10 eq). The reaction was carried out at 100° C. for 18 hours under nitrogen atmosphere. After completion of the reaction, the reaction solution was cooled to room temperature, followed by addition of 50 mL of water. After phase separation, the organic phase was sequentially washed with 50 mL of ammonium chloride solution (27%), 50 mL of sodium hydrogen carbonate solution (9%), and 45 mL of saturated brine, dried over anhydrous sodium sulfate and rotary evaporated to dry with water pump under reduced pressure at 45° C. to about 30 mL of toluene remaining. 60 mL of n-hexane was added to the organic phase, followed by filtration. The filter cake was washed with 60 mL of isopropanol (10 minutes in ice bath) and rotary evaporated to dry with water pump under reduced pressure at 40° C. (white solid). The crude product was purified by column chromatography (SiO$_2$, 100-200 mesh, PE:EA=10:1-3:1) to give WXBB-1-5 (1.80 g, 7.75 mmol, 19.39% yield) as a yellow solid. $^1$H NMR (400 MHz, DMSO-$d_6$) δ ppm 0.81-0.86 (m, 2H) 0.87-0.90 (m, 2H) 2.42 (s, 3H) 4.98 (s, 2H) 5.20-5.28 (m, 1H) 5.23 (s, 1H) 6.67 (d, J=5.52 Hz, 2H) 6.87 (d, J=5.77 Hz, 1H).

Step 4: Synthesis of Compound WXBB-1-6

WXBB-1-5 (1.25 g, 5.38 mmol, 1.00 eq) was placed in a 100 mL single-necked flask containing acetic acid (20.00 mL). Potassium thiocyanate solid (1.05 g, 10.76 mmol, 1.05 mL, 2.00 eq) was added to the reaction solution and charged with nitrogen three times. The reaction was carried out at 110° C. for 5 hours under nitrogen atmosphere. After completion of the reaction, the reaction solution was cooled to room temperature, rotary evaporated to dry with oil pump under reduced pressure at 60° C., and dissolved in 10 mL of dichloromethane. The organic phase was washed with water (5 mL*2), and the aqueous phase was extracted with 10 mL*2 of dichloromethane. The organic phases were combined, dried over anhydrous sodium sulfate and rotary evaporated to dry under reduced pressure to give a brown solid. The obtained brown solid was dissolved with 5 mL of ethyl acetate, follow by addition of 15 mL of n-hexane. The solution was layered with a brown upper layer, and stirred by magnetizer with no precipitation of solids. The mixture is rotary evaporated to dry under reduced pressure to give a brown oil. The crude product was purified by column chromatography (SiO$_2$, 100-200 mesh, PE:EA=10:1-3:1) to give WXBB-1-6 (390.00 mg, 756.23 μmol, 14.06% yield, 53% purity) as a yellow solid. m/z=274.0 (M+1).

Step 5: Synthesis of Compound WXBB-1-7

Acetic acid (8.00 mL), water (1.60 mL) and hydrogen peroxide (487.96 mg, 4.30 mmol, 413.53 μL, 30% purity, 3.01 eq) were added into a pre-dried 100 mL three-necked flask and the mixture was heated to 45° C. (internal temperature) under nitrogen atmosphere. After the addition of WXBB-1-6 (390.00 mg, 1.43 mmol, 1.00 eq) as a solid (the internal temperature was kept below 55° C.), and the reaction solution was reacted at 45° C. for 30 minutes. After completion of the reaction, the reaction solution was cooled to room temperature, followed by addition of 4 mL of a 20% sodium sulfite solution, stirred at room temperature for 0.5 hour and rotary evaporated to dry with oil pump to give a white solid. 4 mL of Water was added to the white solid, and the pH was adjusted to about 10 with 4N ammonia hydroxide. The aqueous phase was extracted with dichloromethane (6 mL*3). The organic phase was dried over anhydrous sodium sulfate and rotary evaporated to dry under reduced pressure to give WXBB-1-7 (200.00 mg, 828.98 μmol, 57.97% yield) as a yellow solid. m/z=242.2 (M+1).

Step 6: Synthesis of Compound WXBB-1

A reaction solution of WXBB-1-7 (200.00 mg, 828.98 μmol, 1.00 eq) and hydrochloric acid (6.00 mL, 38% purity) was added to a dried 100 mL single-necked flask and reacted for at 100° C. 18 hours. After completion of the reaction, the reaction solution was cooled to room temperature and rotary evaporated to dry. 5 mL*2 of Toluene was added thereto and rotary evaporated to dry under reduced pressure to give WXBB-1 (200.00 mg, 768.46 μmol, 92.70% yield) as a brown solid. $^1$H NMR (400 MHz, DMSO-d6) δ ppm 0.81-0.89 (m, 2H) 0.98-1.06 (m, 2H) 1.96-2.05 (m, 1H) 2.24 (s, 3H) 7.54 (d, J=11.29 Hz, 1H) 7.74 (s, 1H) 8.00 (d, J=6.78 Hz, 1H) 9.28 (s, 1H), m/z=261.1 (M+1).

Fragment WXBB-2:

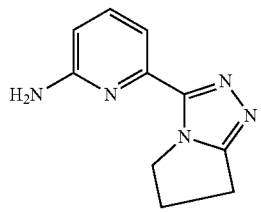 [SMILES: Nc1cccc(-c2nnc3n2CCC3)n1]

Synthetic Route:

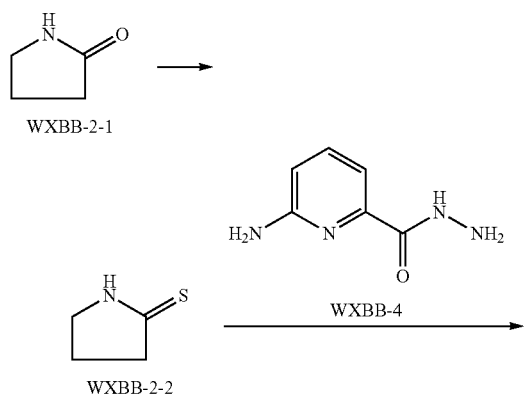

Step 1: Synthesis of Compound WXBB-2-2

Phosphorus pentasulfide (52.24 g, 235.02 mmol, 24.99 mL, 2.00 eq) was dissolved in tetrahydrofuran (300.00 mL), followed by slow addition of sodium carbonate (12.45 g, 117.51 mmol, 1.00 eq). The system was stirred at 20° C. for 1 hour. Compound WXBB-2-1 was added to the system, and the system was warmed to 60° C. and stirred for 48 hours. The reaction solution was cooled to room temperature, followed by filtration. The filtrate was concentrated to dry under reduced pressure to give a crude product. The crude product was purified by column chromatography (0-60% EA/PE) to give Compound WXBB-2-2 (6.20 g, 61.28 mmol, 52.15% yield) as white solid. $^1$H NMR (400 MHz, CHLOROFORM-d) δ ppm 2.166-2.249 (m, 2H) 2.896-2.936 (m, 2H) 3.664-3.699 (m, 2H) 8.676 (s, 1H).

Step 2: Synthesis of Compound WXBB-2

Compound WXBB-2-2 (200.00 mg, 1.98 mmol, 1.00 eq) and Compound WXBB-4 (360.00 mg, 2.37 mmol, 1.19 eq) were dissolved in cyclohexanol (4.00 mL). The system was stirred at 170° C. for 24 hours under nitrogen atmosphere. The reaction solution was cooled to room temperature, diluted with water (80 mL) and extracted with ethyl acetate (30 mL*6). The organic phase was dried over anhydrous sodium sulfate, followed by filtration. The filtrate was concentrated under reduced pressure to give a crude product. The crude product was purified by column chromatography (0-10% MeOH/DCM) to give Compound WXBB-2 (180.00 mg, 831.88 μmol, 42.01% yield, 93% purity) as a yellow solid. $^1$H NMR (400 MHz, DMSO-d6) δ ppm 2.71-2.64 (m, 2H) 2.86 (d, J=7.2 Hz, 2H) 4.32 (t, J=7.2 Hz, 2H) 6.13 (br.s, 2H) 6.48 (d, J=8.4 Hz, 1H) 7.22 (d, J=7.2 Hz, 1H) 7.52-7.47 (m, 1H). m/z=202.0[M+H]+.

Fragment WXBB-3:

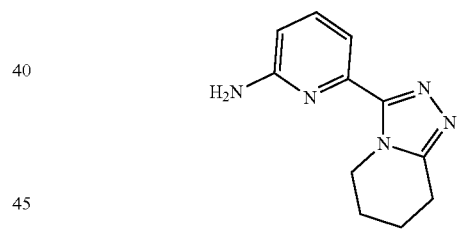

Synthetic Route:

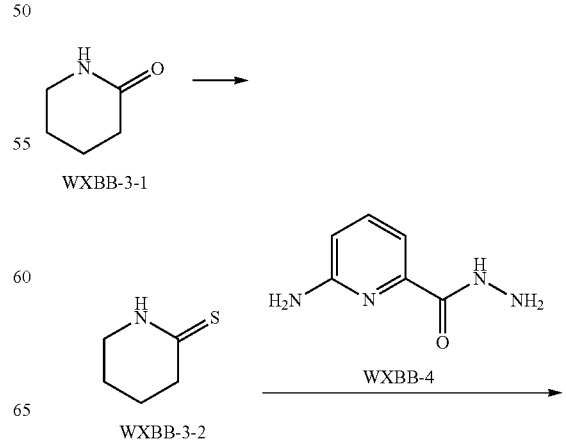

Synthetic Route:

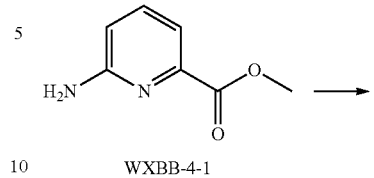

WXBB-4-1

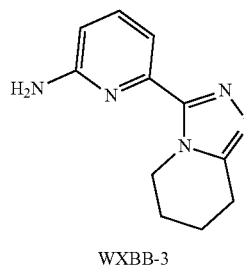

WXBB-3

Step 1: Synthesis of Compound WXBB-3-2

Phosphorus pentasulfide (56.06 g, 252.19 mmol, 26.82 mL, 1.00 eq) was added to acetonitrile (500.00 mL) to form a suspension, followed by slow addition of triethylamine (25.52 g, 252.19 mmol, 34.96 mL, 1.00 eq). The system was stirred at room temperature for 1 hour, followed by addition of WXBB-3-1 (25.00 g, 252.19 mmol, 1.00 eq), and the system was stirred at 60° C. for 19 hours. The reaction solution was poured into sodium hypochlorite (200 mL), and concentrated under reduced pressure to remove acetonitrile and extracted with dichloromethane (200 mL*3). The organic phases were combined, sequentially washed with water (400 mL) and brine (400 mL) and dried over anhydrous magnesium sulfate, followed by filtration. The filtrate was concentrated under reduced pressure to give a crude product. The crude product was purified by column chromatography (0-10% MeOH/DCM) to give Compound WXBB-3-2 (10.00 g, 86.81 mmol, 34.42% yield) as a yellow solid. $^1$H NMR (400 MHz, DMSO-d6) δ ppm 1.53-1.71 (m, 4H) 2.57-2.67 (m, 2H) 3.13 (br s, 1H) 3.18 (td, J=5.77, 2.51 Hz, 1H).

Step 2: Synthesis of Compound WXBB-3

Compound WXBB-3-2 (6.00 g, 52.08 mmol, 1.00 eq) and Compound WXBB-4 (8.72 g, 57.29 mmol, 1.10 eq) were dissolved in cyclohexanol (100.00 mL). The system was stirred at 170° C. for 6 hours under nitrogen atmosphere. The reaction solution was cooled to room temperature, diluted with water (200 mL), adjusted to pH 5 with hydrochloric acid (2N, 100 mL), and extracted with ethyl acetate (200 mL). The aqueous phase was adjusted to pH 9 with sodium hydroxide (2N, 100 mL) and extracted with ethyl acetate (200 mL*2). The organic phases were combined, sequentially washed with water (200 mL) and brine (200 mL) and dried over anhydrous magnesium sulfate, followed by filtration. The filtrate was concentrated under reduced pressure to give a crude product. The crude product was purified by column chromatography (0-10% DCM/MeOH) to give Compound WXBB-3 (5.00 g, 17.50 mmol, 33.60% yield, 75.32% purity) as a brown solid. m/z=216.0 [M+H]+.

Fragment WXBB-4:

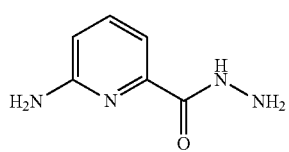 [SMILES: NNC(=O)c1cccc(N)n1]

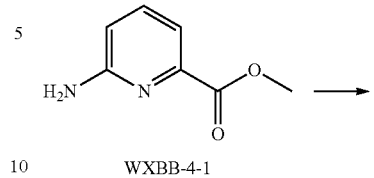

WXBB-4

Step 1: Synthesis of Compound WXBB-4

Compound WXBB-4-1 (20.00 g, 131.45 mmol, 1.00 eq) was dissolved in methanol (200.00 mL) to give a pale-yellow solution, followed by slow addition of hydrazine hydrate (19.74 g, 394.35 mmol, 19.17 mL, 3.00 eq). The reaction system was stirred at 75° C. for 1.5 hours. After completion of the reaction, the reaction mixture was cooled to room temperature, followed by filtration. The filter cake was washed with ethyl acetate (50 mL*2), and the filter cake was rotary evaporated to dry under reduced pressure to give Compound WXBB-4 (20.00 g, 131.45 mmol, 100.00% yield) as a white solid. $^1$H NMR (400 MHz, DMSO-d6) δ ppm 4.48 (br s, 2H) 6.09 (s, 2H) 6.60 (d, J=8.28 Hz, 1H) 7.11 (d, J=7.03 Hz, 1H) 7.51 (t, J=7.78 Hz, 1H) 9.19 (br s, 1H).

Example 001: WX001

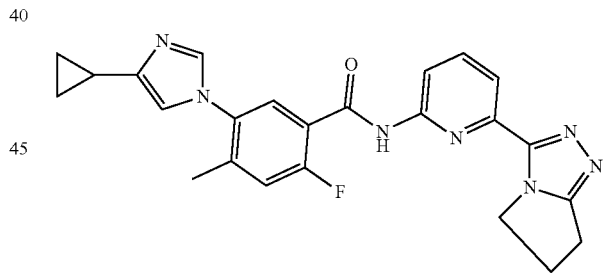

Synthetic Route:

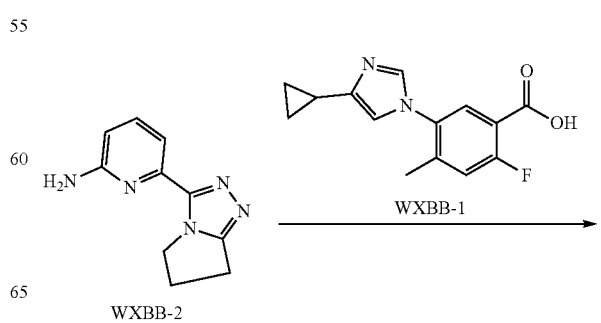

WXBB-2

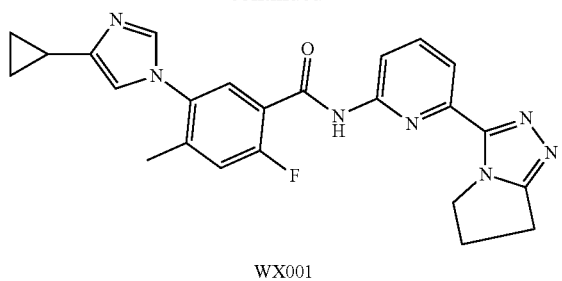

WX001

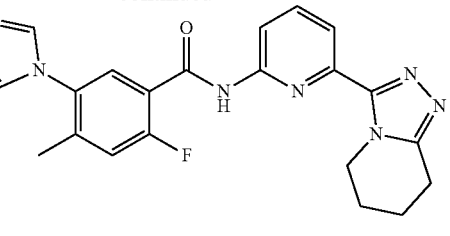

WX002

Step 1: Synthesis of Compound WX001

WXBB-1 (100.00 mg, 337.02 μmol, 1.00 eq, HCl) and WXBB-2 (80.00 mg, 369.73 μmol, 1.10 eq) (93% purity) were dissolved in pyridine (5.00 mL), followed by slow addition of phosphorus oxychloride (50.00 mg, 326.09 μmol, 30.30 μL, 0.97 eq). The reaction system was stirred at 50° C. for 1 hour. The reaction solution was quenched with water and concentrated under reduced pressure to give a crude product. The crude product was isolated and purified by prep-HPLC (neutral system) to give WX001. $^1$HNMR: 0.63-0.71 (m, 2H) 0.74-0.83 (m, 2H) 1.76-1.89 (m, 1H) 2.23 (s, 3H) 2.67 (quin, J=7.34 Hz, 2H) 2.81-2.92 (m, 2H) 4.38 (t, J=7.03 Hz, 2H) 7.17 (d, J=0.75 Hz, 1H) 7.47 (d, J=10.79 Hz, 1H) 7.56-7.64 (m, 1H) 7.68 (d, J=1.00 Hz, 1H) 7.85 (d, J=7.53 Hz, 1H) 7.98 (t, J=7.91 Hz, 1H) 8.15 (d, J=8.28 Hz, 1H) 10.90 (s, 1H). m/z=444.2 (M+1).

Step 1: Synthesis of Compound WX002

WXBB-1 (100.00 mg, 337.02 μmol, 1.21 eq, HCl) was dissolved in dichloromethane (5.00 mL), followed by addition of oxalyl chloride (70.76 mg, 557.49 μmol, 48.80 μL, 2.00 eq) and N,N-dimethylformamide (20.37 mg, 278.75 μmol, 21.45 μL, 1.00 eq) under nitrogen atmosphere. The system was stirred at 0° C. for 1 hour. The reaction solution was rotary evaporated to dry under reduced pressure, followed by sequential addition of dichloromethane (5.00 mL), WXBB-3 (60.00 mg, 278.75 μmol, 1.00 eq) and DMAP (136.22 mg, 1.12 mmol, 4.00 eq). The system was stirred at 0° C. for 3 hours. The reaction solution was rotary evaporated under reduced pressure to give a crude product. The crude product was isolated by prep-TLC plate (DCM:MeOH=20:1) to give WX002. $^1$H NMR (400 MHz, METHANOL-d4) ppm 9.17 (s, 1H), 8.47 (d, J=8.3 Hz, 1H), 8.16-8.08 (m, 1H), 8.06-7.96 (m, 2H), 7.63 (s, 1H), 7.50 (d, J=10.8 Hz, 1H), 4.82 (br. s., 2H), 3.27 (t, J=6.0 Hz, 2H), 2.36 (s, 3H), 2.20 (br. s., 2H), 2.15-2.04 (m, 3H), 1.22-1.12 (m, 2H), 0.98-0.89 (m, 2H).

Example 002: WX002

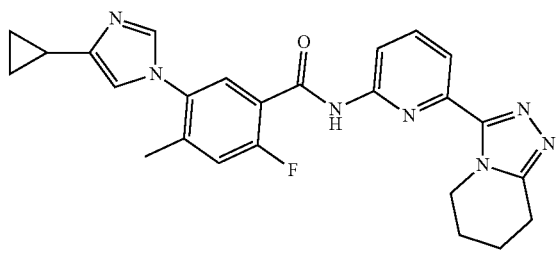 [SMILES: Cc1cc(F)c(C(=O)Nc2cccc(-c3nnc4n3CCCC4)n2)cc1-n1cnc(C2CC2)c1]

Example 003: WX003

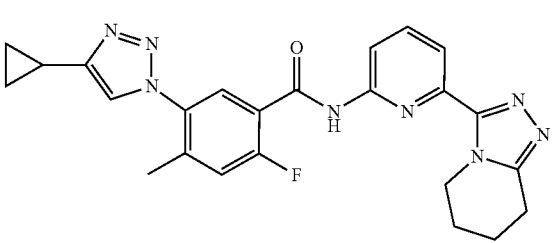 [SMILES: Cc1cc(F)c(C(=O)Nc2cccc(-c3nnc4n3CCCC4)n2)cc1-n1cc(C2CC2)nn1]

Synthetic Route:

Synthetic Route:

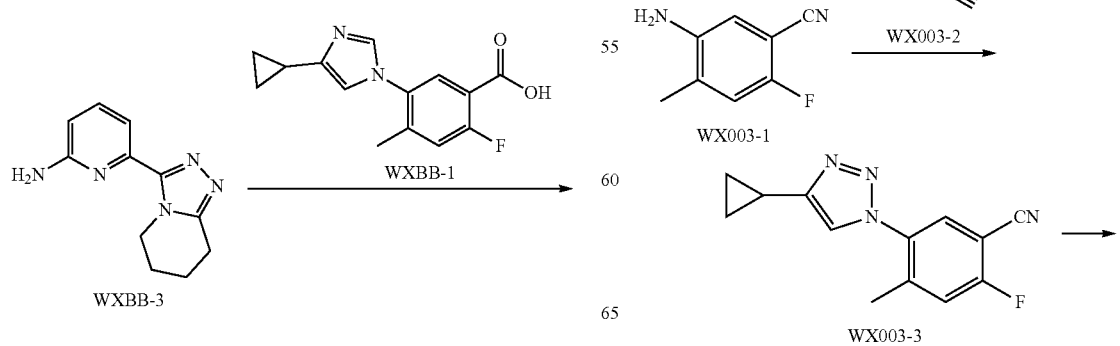

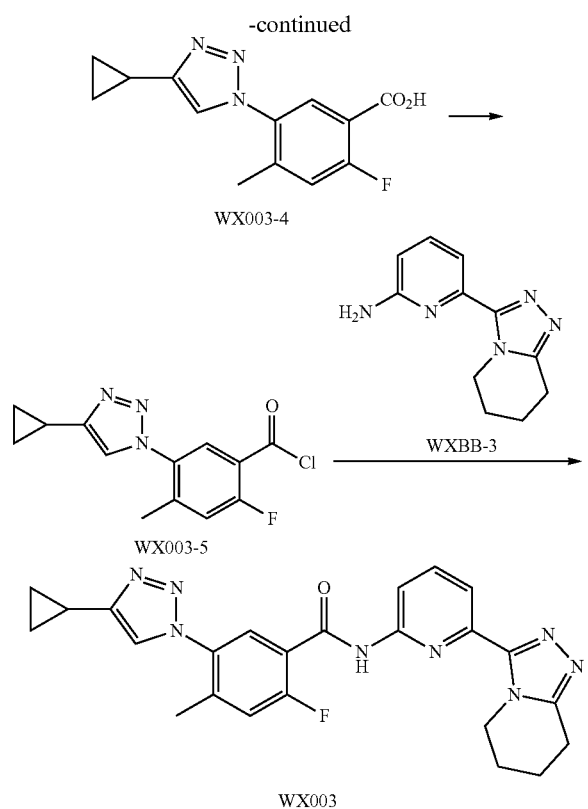

Step 1: Synthesis of Compound WX003-3

WX003-1 (1.50 g, 9.99 mmol, 1.00 eq) was dissolved in acetonitrile (60.00 mL) and cooled to 0° C., followed by addition of isoamyl nitrite (1.76 g, 14.99 mmol, 2.02 mL, 1.50 eq), then TMSN$_3$ (1.73 g, 14.99 mmol, 1.96 mL, 1.50 eq) was added dropwise to the reaction solution. The ice bath was removed after 25 minutes. The reaction solution was warmed to room temperature 25° C. and reacted for 2 hours. WX003-2 (1.98 g, 29.97 mmol, 2.48 mL, 3.00 eq) and Cu$_2$O (142.95 mg, 999.00 μmol, 102.11 μL, 0.10 eq) were then added to the reaction solution, and the reaction was carried out at 50° C. for 18 hours under nitrogen atmosphere. After completion of the reaction, the reaction solution was cooled to room temperature and rotary evaporated to dry, diluted with 50 mL of dichloromethane, sequentially washed with 30 mL of saturated ammonium chloride and 30 mL of saturated brine and dried over anhydrous sodium sulfate, rotary evaporated to dry. The crude product was purified by column chromatography (SiO$_2$, PE:EA=10:1 to 4:1) to give WX003-3. m/z=242.9 [M+1].

Step 2: Synthesis of Compound WX003-4

WX003-3 (380.00 mg, 1.57 mmol, 1.00 eq) was added in 38% hydrochloric acid (15.00 mL) and refluxed at 100° C. for 18 hours. The reaction solution was adjusted to pH 9 with sodium carbonate solid, and extracted with 10 mL*3 of ethyl acetate. The aqueous phase was retained, adjusted to pH 2 with 2N HCl and extracted with 30 mL*3 of ethyl acetate. The organic phase was retained, and dried over anhydrous sodium sulfate, followed by filtration. The filtrate was rotary evaporated to dry to give WX003-4. m/z=261.9 [M+1].

Step 3: Synthesis of Compound WX003-5

WX003-4 (300.00 mg, 1.15 mmol, 1.00 eq) was dissolved in anhydrous dichloromethane (10.00 mL) and charged with nitrogen gas, followed by addition of oxalyl chloride (248.15 mg, 1.95 mmol, 171.14 μL, 1.70 eq) to form an emulsion. Afterwards, anhydrous N,N-dimethylformamide (8.41 mg, 115.00 μmol, 8.85 μL, 0.10 eq) was added thereto, and the reaction was carried out at 25° C. for 2 hours under nitrogen atmosphere. 5 mL of anhydrous dichloromethane was added to the reaction solution and concentrated under reduced pressure at 35° C. to 5 mL of anhydrous dichloromethane remaining. Such procedures were repeated four times and the resulting product in anhydrous DCM was used directly in the next step. The resulting WX003-5 was dissolved in 5 mL of dichloromethane. m/z=276.1 [methyl ester MS].

Step 4: Synthesis of Compound WX003

Diisopropylethylamine (131.82 mg, 1.02 mmol, 178.14 μL, 1.00 eq) was added to a solution of WX003-5 (285.29 mg, 1.02 mmol, 1.00 eq) in anhydrous dichloromethane (6.00 mL) under nitrogen atmosphere, followed by the addition of WXBB-3 (220.00 mg, 1.02 mmol, 1.00 eq). The reaction was carried out at 25° C. for 18 hours under nitrogen atmosphere. After completion of the reaction, 5 mL of saturated brine was added to the reaction solution. The organic phase was separated and rotary evaporated (40° C. water pump rotary evaporation) to dry under reduced pressure to give a crude product. The crude product was purified by prep-HPLC (column: water Xbridge 150*25 5 u; mobile phase: [Water (10 mM NH$_4$HCO$_3$)-ACN]; B %: 12%-52%, 10.5 min) to give compound WX003. $^1$H NMR (400 MHz, CHLOROFORM-d) δ ppm 0.95-1.00 (m, 2H) 1.03-1.10 (m, 2H) 1.95-2.02 (m, 2H) 2.04-2.12 (m, 3H) 2.35 (s, 3H) 3.10 (t, J=6.34 Hz, 2H) 4.51 (t, J=6.09 Hz, 2H) 7.2366, 1H) 7.50 (s, 1H) 7.90 (t, 3=8.03 Hz, 1H) 8.12 (dd, J=15.37, 7.34 Hz, 2H) 8.36 (d, J=8.28 Hz, 1H) 9.02 (br d, J=14.30 Hz, 1H).

Example 004: WX004

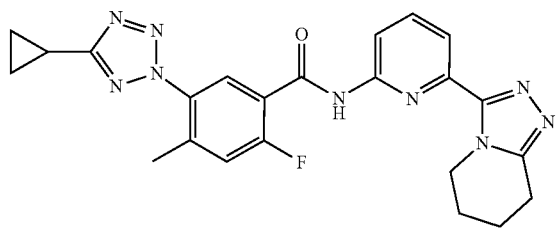 [SMILES: Cc1cc(F)c(C(=O)Nc2cccc(-c3nnc4n3CCCC4)n2)cc1-n1nnc(C2CC2)n1]

Synthetic Route:

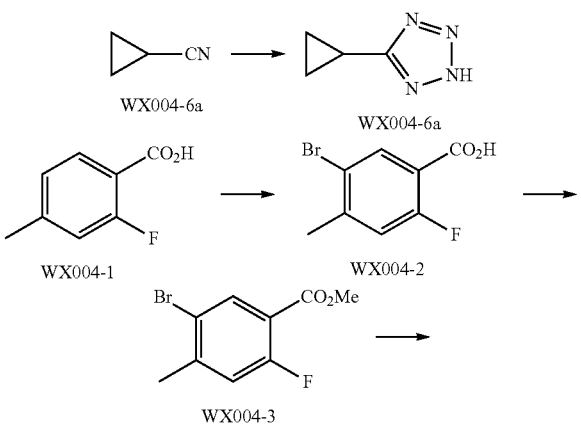

Step 1: Synthesis of Compound WX004-2

N-bromosuccinimide (22.97 g, 129.75 mmol, 1.00 eq) was added to a mixture of WX004-1 (20.00 g, 129.75 mmol, 1.00 eq) and concentrated sulfuric acid (200.00 mL), and stirred at 20° C. for 20 minutes. The reaction solution was poured into ice water (1000 mL) while stirring, and a white solid was formed. After filtration, the filter cake was dissolved with 500 mL of dichloromethane, dried over magnesium sulfate, filtered and evaporated to dry to give WX004-2. $^1$H NMR (400 MHz, CHLOROFORM-d) δ ppm 2.45 (s, 3H) 7.07 (d, J=11.17 Hz, 1H) 8.16 (d, J=6.90 Hz, 1H).

Step 2: Synthesis of Compound WX004-3

The raw material WX004-2 (27.00 g, 115.86 mmol, 1.00 eq) was dissolved in methanol (200.00 mL), followed by addition of concentrated sulfuric acid (11.36 g, 115.86 mmol, 6.18 mL, 1.00 eq). The reaction was carried out at 90° C. for 18 hours. The reaction solution was evaporated to dry and dissolved in 250 mL of dichloromethane, followed by addition of 150 mL of saturated sodium bicarbonate solution, extraction and evaporation to dry to give WX004-3. $^1$H NMR (400 MHz, CHLOROFORM-d) δ ppm 2.42 (s, 3H) 3.92 (s, 3H) 7.04 (d, J=11.04 Hz, 1H) 8.09 (d, J=6.90 Hz, 1H).

Step 3: Synthesis of Compound WX004-4

WX004-3 (5.00 g, 20.24 mmol, 1.00 eq) was dissolved in dioxane (60.00 mL) followed by addition of (Bpin)$_2$ (7.71 g, 30.36 mmol, 1.50 eq), potassium acetate (5.96 g, 60.72 mmol, 3.00 eq) and Pd(dppf)Cl$_2$ (2.96 g, 4.05 mmol, 0.20 eq), and charged with nitrogen gas. The reaction was carried out at 90° C. for 18 hours under nitrogen atmosphere. After completion of the reaction, the reaction mixture was filtered through diatomite, and the filtrate was evaporated to dry. The crude product was purified by column chromatography (SiO$_2$, PE:EA=20:1-7:1) to give WX004-4. $^1$H NMR (400 MHz, CHLOROFORM-d) δ ppm 1.31-1.37 (m, 12H) 2.53-2.58 (m, 3H) 3.90 (s, 3H) 6.92 (d, J=12.17 Hz, 1H) 8.32 (d, J=8.53 Hz, 1H)

Step 4: Synthesis of Compound WX004-5

WX004-4 was dissolved in tetrahydrofuran (35.00 mL), followed by addition of sodium periodate (5.09 g, 23.80 mmol, 1.32 mL, 2.00 eq) and 1N hydrochloric acid solution (10.00 mL), The reaction solution was reacted at 25° C. for 18 hours. After completion of the reaction, the reaction solution was evaporated to dry and diluted with 60 mL of ethyl acetate. The organic phase was washed with 40 mL of water and 40 mL of saturated brine, dried over anhydrous sodium sulfate and evaporated to dry to give a crude product. The crude product was purified by column chromatography (SiO$_2$, PE:EA=5:1 to EA) to give WX004-5.

Step 5: Synthesis of Compound WX004-6

Sodium azide (9.69 g, 149.05 mmol, 2.50 eq) and tributyl stannous chloride (48.52 g, 149.05 mmol, 40.10 mL, 2.50 eq) were added to a solution of WX004-6a (4.00 g, 59.62 mmol, 4.40 mL, 1.00 eq) in o-xylene (50.00 mL). The reaction was carried out at 160° C. for 6 hours under nitrogen atmosphere. (The reaction apparatus was quenched with sodium hypochlorite). After the reaction solution was cooled to room temperature, the reaction solution was adjusted to pH 9 with 20% sodium hydroxide, and stirred at room temperature for 1 hour, followed by separation. The aqueous phase was adjusted to pH=2 with 2N hydrochloric acid, extracted with 100 mL*3 of ethyl acetate, dried over anhydrous sodium sulfate, and evaporated to dry with the placement of the baffles to give WX004-6. $^1$H NMR (400 MHz, METHANOL-d$_4$) δ ppm 1.01-1.09 (m, 2H) 1.19-1.25 (m, 2H) 2.17-2.25 (m, 1 H).

Step 6: Synthesis of Compound WX004-7

WX004-6 (800.00 mg, 7.26 mmol, 1.00 eq), WX004-5 (1.54 g, 7.26 mmol, 1.00 eq) and Cu$_2$O (51.98 mg, 363.00 μmol, 37.13 μL, 0.05 eq) were sequentially added in dimethylsulfoxide (24.00 mL). The solution was reacted at 110° C. for 18 hours under O$_2$ atmosphere. After completion of the reaction, the reaction solution was cooled to room temperature, diluted with 80 mL of dichloromethane, and washed with 60 mL of 1M hydrochloric acid and 60 mL of saturated brine. After separation, the organic phase was dried over anhydrous sodium sulfate and evaporated to dry. The crude product was purified by column chromatography (SiO$_2$, petroleum ether:ethyl acetate=1:0 to 50:1 to 20:1) to give WX004-7. $^1$H NMR (400 MHz, CHLOROFORM-d) δ ppm 1.1 (m, 2H) 1.2 (m, 2H) 2.2 (m, 1H) 2.42 (s, 3H) 3.94 (m, 3H) 7.19 (d, J=10.67 Hz, 1H) 8.19 (d, J=6.65 Hz, 1H).

Step 7: Synthesis of Compound WX004-8

WX004-7 (500.00 mg, 1.81 mmol, 1.00 eq) was dissolved in tetrahydrofuran (5.00 mL) and water (5.00 mL), followed by addition of LiOH (130.04 mg, 5.43 mmol, 3.00 eq). The reaction solution was reacted at 25° C. for 2 hours, and extracted with 10 mL of methyl tert-butyl ether. The isolated aqueous phase was adjusted to pH 2 with 2N hydrochloric acid, and extracted with 20 mL*3 of ethyl acetate. The organic phase was dried over anhydrous sodium sulfate, evaporated to dry to give WX004-8. $^1$H NMR (400 MHz, CHLOROFORM-d) δ ppm 1.18 (d, J=6.78 Hz, 4H) 2.26-2.36 (m, 1H) 2.45 (s, 3H) 7.23 (d, J=10.79 Hz, 1H) 8.27 (d, J=6.65 Hz, 1H).

Step 8: Synthesis of Compound WX004-9

WX004-8 (150.00 mg, 572.00 μmol, 1.00 eq) was added into a vial containing anhydrous dichloromethane (7.00 mL) and charged with nitrogen gas three times. Oxalyl chloride (123.43 mg, 972.40 μmol, 85.12 μL, 1.70 eq) was then added thereto to form an emulsion, followed by addition of N,N-dimethylformamide (4.18 mg, 57.20 μmol, 4.40 μL, 0.10 eq). The reaction was carried out at 25° C. for 1 hour under nitrogen atmosphere. 5 mL of anhydrous dichloromethane was added to the reaction solution, and evaporated at room temperature under reduced pressure to 2 mL of anhydrous dichloromethane remaining. Such procedures were repeated four times to give WX004-9 dissolved in 2 mL of anhydrous dichloromethane. m/z=277.1 (M+1) (methyl ester MS).

Step 9: Synthesis of Compound WX004

WX004-9 (130.40 mg, 464.58 μmol, 1.00 eq) was dissolved in anhydrous dichloromethane (3.00 mL) in a vial, followed by addition of WXBB-3 (100.00 mg, 464.58 μmol, 1.00 eq) and diisopropylethylamine (60.04 mg, 464.58 μmol, 81.14 μL, 1.00 eq). The reaction was carried out at 25° C. for 18 hours under nitrogen atmosphere. The reaction solution was washed with 10 mL of saturated brine, dried over anhydrous sodium sulfate and evaporated to give a crude product. The crude product was purified by prep-HPLC (column: Waters Xbridge 150*25 mm 5 μm; mobile phase: [water (10 mM NH4HCO3)-ACN]; B %: 25%-60%, 10.5 min) to give WX004. m/z=460.2 [M+1]. $^1$H NMR (400 MHz, CHLOROFORM-d) δ ppm 1.19 (d, J=6.65 Hz, 4H) 1.94-2.13 (m, 4H) 2.32 (t, J=6.53 Hz, 1H) 2.49 (s, 3H) 3.11 (t, J=6.15 Hz, 2H) 4.52 (t, J=5.96 Hz, 2H) 7.26 (br s, 1H) 7.91 (t, J=8.03 Hz, 1H) 8.11 (d, J=7.28 Hz, 1H) 8.35-8.40 (m, 1H) 8.45 (d, J=7.28 Hz, 1H) 9.01 (br d, J=15.06 Hz, 1H)

Example 005: WX005

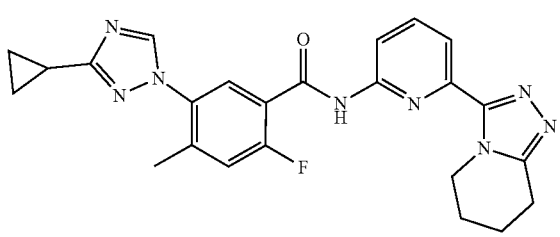 [SMILES: Cc1cc(F)c(C(=O)Nc2cccc(-c3nnc4n3CCCC4)n2)cc1-n1cnc(C2CC2)n1]

Synthetic Route:

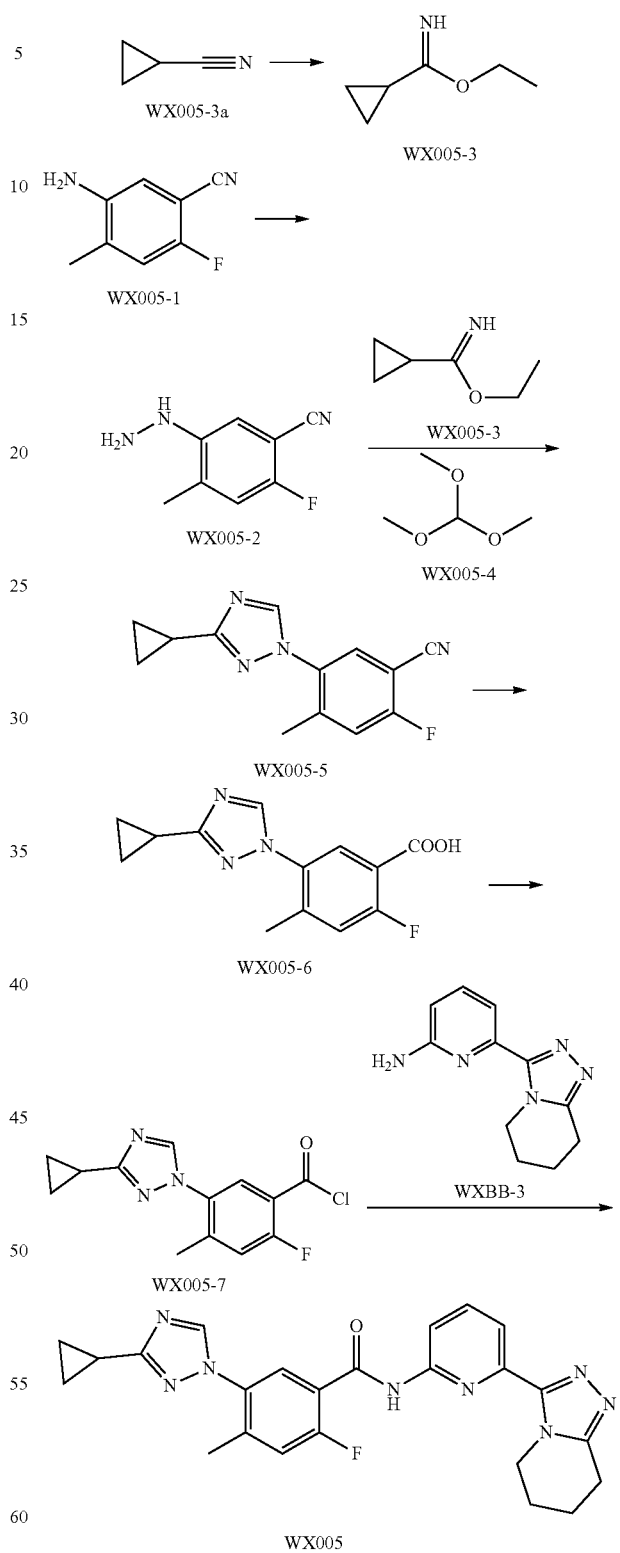

Step 1: Synthesis of Compound WX005-3

WX005-3a (2.28 g, 33.91 mmol, 2.50 mL, 1.00 eq) was added into a pre-dried 100 mL three-necked flask, and charged with nitrogen gas three times, followed by addition of 10 mL of hydrochloric acid (4.87 N in dioxane). Afterwards, anhydrous ethanol (1.56 g, 33.91 mmol, 1.98 mL, 1.00 eq) was added dropwise to the reaction system under nitrogen atmosphere. After completion of the addition, the mixture was reacted at 25° C. for 3 hours. The reaction solution was filtered and evaporated to dry to give WX005-3. $^1$H NMR (400 MHz, CHLOROFORM-d) δ ppm 1.12-1.23 (m, 4H) 1.36 (t, J=7.03 Hz, 3H) 2.30-2.41 (m, 1H) 4.54 (q, J=7.03 Hz, 2H) 11.15 (br s, 1H) 12.24 (br s, 1H).

Step 2: Synthesis of Compound WX005-2

WX005-1 (1.72 g, 11.46 mmol, 1.00 eq) was dissolved in hydrochloric acid (63.00 mL) and cooled to 0° C., followed by dropwise addition of a solution of sodium nitrite (948.49 mg, 13.75 mmol, 746.84 μL, 1.20 eq) in water (6.00 mL) solution. After completion of the dropwise addition, the reaction was carried out at 0-5° C. for 0.5 hour. A solution of stannous chloride dihydrate (7.76 g, 34.38 mmol, 2.86 mL, 3.00 eq) in hydrochloric acid (4 mL, 37%) was dropwise added to the reaction solution, and the reaction was carried out at 25° C. for 3 hours, forming a large amount of gray precipitates. After completion of the reaction, the reaction solution was filtered, and methanol (20 mL) was added to the filter cake. The filtrate was adjusted to pH 8 with saturated aqueous solution of sodium bicarbonate and extracted with ethyl acetate (3×100 mL). The organic phases were combined, washed with saturated brine (2×100 mL), dried over anhydrous sodium sulfate and concentrated under reduced pressure to give a dark yellow solid. The dark yellow solid was isolated by flash column chromatography (silica gel: 100-200 mesh; DCM:MeOH=20:1) to give product WX005-2. m/z=166.3 [M+1].

Step 3: Synthesis of Compound WX005-5

WX005-2 (3.00 g, 14.88 mmol, 1.00 eq) and WX005-3 (2.23 g, 14.88 mmol, 1.00 eq) were added into a pre-dried 40 mL vial, followed by addition of anhydrous ethanol (45.00 mL) and triethylamine (3.01 g, 29.76 mmol, 4.12 mL, 2.00 eq). The reaction was carried out at 20° C. for 0.5 hour. The solvent was removed by rotary evaporation. Afterwards, WX005-4 (15.79 g, 148.80 mmol, 16.28 mL, 10.00 eq) and carbamic acid (1.88 g, 29.76 mmol, 2.00 eq) were added to the crude product, respectively. The temperature was raised to C and the reaction was carried out for 15.5 hours. The reaction system was cooled to room temperature, diluted with 50 mL of saturated sodium bicarbonate and 50 mL of ethyl acetate. The organic phase was collected after separation and the aqueous was extracted with ethyl acetate (20 mL×3). The organic phase were combined, washed with saturated brine (50 mL), dried over anhydrous sodium sulfate and concentrated under reduced pressure to give a yellow solid. The crude product was recrystallized with ethyl acetate/petroleum ether=1/5 (30 mL) to give product WX005-5. $^1$H NMR (400 MHz, CHLOROFORM-d) δ=8.01 (s, 1H), 7.54 (d, J=5.9 Hz, 1H), 7.23-7.13 (m, 1H), 2.31-2.21 (m, 3H), 2.05 (quin, J=6.6 Hz, 1H), 0.97 (d, J=6.7 Hz, 4H).

Step 4: Synthesis of Compound WX005-6

WX005-5 (500.00 mg, 2.06 mmol, 1.00 eq) was added into a pre-dried 100 mL flask and dissolved in hydrochloric acid (10.20 g, 279.76 mmol, 10.00 mL, 135.81 eq). The reaction was stirred at 100° C. for 16 hours. The reaction system was cooled to room temperature, and a large amount of solid was precipitated after cooling, followed by filtration through a five-hole funnel. The filter cake was collected to give WX005-6. $^1$H NMR (400 MHz, METHANOL-d4) δ=9.67 (s, 1H), 8.06 (d, J=6.6 Hz, 1H), 7.36 (d, J=11.0 Hz, 1H), 2.32 (s, 3H), 2.26-2.11 (m, 1H), 1.27-1.18 (m, 2H), 1.15-1.05 (m, 2H).

Step 5: Synthesis of Compound WX005-7

WX005-6 (300.00 mg, 1.15 mmol, 1.00 eq) was added into a pre-dried 40 mL vial. Anhydrous dichloromethane (5.00 mL) was added thereto and charged with nitrogen gas, followed by slow addition of oxalyl chloride (291.51 mg, 2.30 mmol, 201.04 μL, 2.00 eq) and anhydrous N,N-dimethylformamide (8.39 mg, 114.83 μmol, 8.83 μL, 0.10 eq) at 0° C. After completion of the addition, the reaction was carried out at 20° C. for 1 hour. The reaction system was concentrated under reduced pressure and repeatedly dissolved with anhydrous dichloromethane, followed by evaporated to dry three times to give WX005-7.

Step 6: Synthesis of Compound WX005

Raw material WX005-7 (300.00 mg, 1.07 mmol, 1.00 eq) was added into a pre-dried 40 mL vial, followed by addition of dichloromethane (3 mL), the reaction system was charged with nitrogen gas and cooled to 0° C. in an ice-water bath. Afterwards, raw material WXBB-3 (230.32 mg, 1.07 mmol, 1.00 eq) was added, and a solution of diisopropylethylamine (138.29 mg, 1.07 mmol, 186.88 μL, 1.00 eq) in dichloromethane (2 mL) was slowly added at 0° C. The temperature was naturally raised to room temperature, and the reaction was stirred at 20° C. for 16 hours. The reaction system was diluted with 10 mL of water/10 mL of dichloromethane. The organic phase was collected after separation, and the aqueous phase was extracted with dichloromethane (5 mL×3). The organic phases were combined, washed with saturated brine (20 mL), dried over anhydrous sodium sulfate and concentrated under reduced pressure. The crude product was isolated and purified by prep-HPLC (neutral) to give the pure product WX005. $^1$H NMR (400 MHz, CHLOROFORM-d) δ=9.02 (br d, J=14.8 Hz, 1H), 8.36 (d, J=7.7 Hz, 1H), 8.16-8.08 (m, 2H), 7.90 (t, J=7.9 Hz, 1H), 7.22 (d, J=12.3 Hz, 1H), 4.51 (t, J=6.1 Hz, 2H), 3.10 (t, J=6.5 Hz, 2H), 2.37 (s, 3H), 2.22-2.11 (m, 1H), 2.11-2.03 (m, 2H), 2.02-1.92 (m, 2H), 1.10-1.00 (m, 4H).

Example 006: WX006

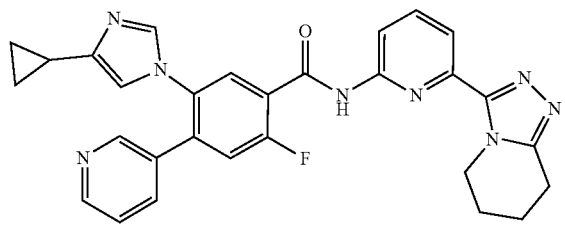 [SMILES: O=C(Nc1cccc(-c2nnc3n2CCCC3)n1)c1cc(-n2cnc(C3CC3)c2)c(-c2cccnc2)cc1F]

Synthetic Route:

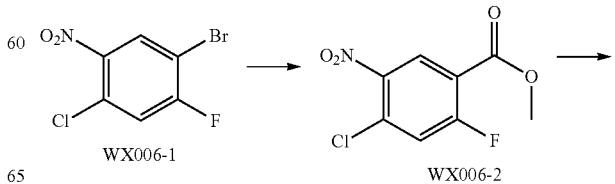

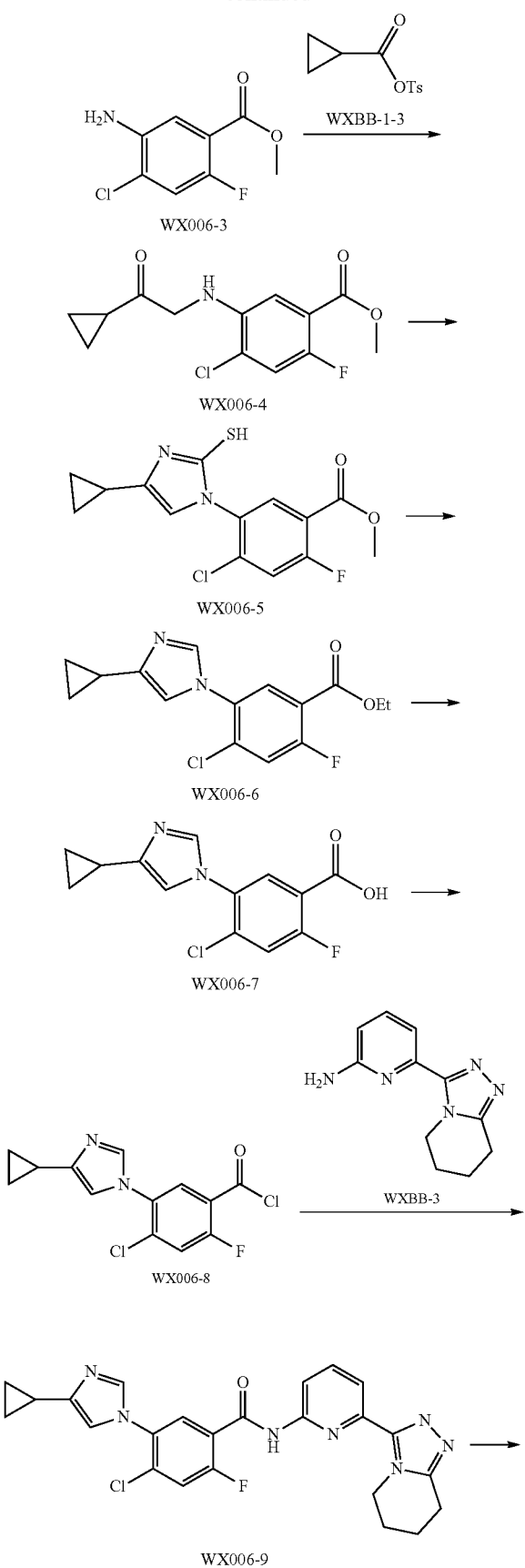

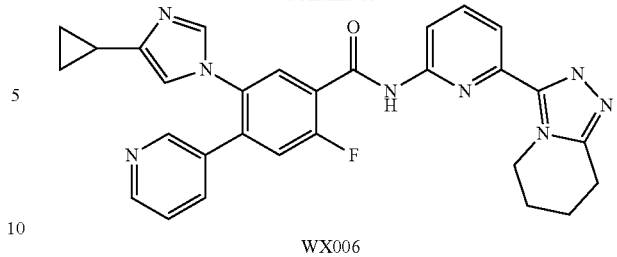

WX006

Step 1: Synthesis of Compound WX006-2

WX006-1 (100.00 g, 455.48 mmol, 1.00 eq) and EtOH (700.00 mL) were added into a pre-dried 250 mL three-necked flask. $H_2SO_4$ (223.37 g, 2.28 mol, 121.40 mL, 5.00 eq) was added dropwise to the reaction solution and refluxed at 80° C. for 5 hours. The reaction system was cooled to room temperature, diluted with 200 mL of EA. The organic phase was collected after separation, and the aqueous phase was extracted with EA (2*100 mL). The organic phases were combined, sequentially washed with saturated aqueous sodium bicarbonate solution (2*100 mL), water (2*100 mL) and saturated brine (2*100 mL), dried over anhydrous sodium sulfate and concentrated under reduced pressure to give residue WX006-2.

Step 2: Synthesis of Compound WX006-3

WX006-2 (117.00 g, 472.52 mmol, 1.00 eq), Fe (65.98 g, 1.18 mol, 2.50 eq), $NH_4Cl$ (27.80 g, 519.77 mmol, 18.17 mL, 1.10 eq) and the solvents $H_2O$ (345.00 mL) and EtOH (1.10 L) were added into a pre-dried 2 L round bottom flask, and the reaction solution was refluxed at 80° C. for 6 hours. The reaction solution was cooled to room temperature and filtrated through the Buchner funnel with diatomite. The filter cake was washed with dichloromethane (300 mL), and the filtrate was extracted with dichloromethane (2×400 mL). The organic phases were combined, washed with saturated brine (2×300 mL), dried over anhydrous sodium sulfate and concentrated under reduced pressure to give residue WX006-3.

Step 3: Synthesis of Compound WX006-4

WX006-3 (37.00 g, 170.02 mmol, 1.00 eq), WXBB-1-3 (47.56 g, 187.02 mmol, 1.10 eq) and DIEA (65.92 g, 510.06 mmol, 89.08 mL, 3.00 eq) were added into a pre-dried 500 mL round bottom flask, followed by addition of xylene (300.00 mL), and stirred continuously at 140° C. for 10 hours. The reaction system was cooled to room temperature and diluted with 150 mL of water. The organic phase was collected after separation, and the aqueous phase was extracted with EA (2*150 mL). The organic phases were combined, sequentially washed with saturated ammonium chloride solution (2*150 mL), saturated brine (2*100 mL), dried over anhydrous sodium sulfate and concentrated under reduced pressure to give WX006-4.

Step 4: Synthesis of Compound WX006-5

WX006-4 (47.80 g, 159.48 mmol, 1.00 eq) and AcOH (250.00 mL) were added into a pre-dried 500 mL flask, followed by addition of potassium thiocyanate (31.00 g, 318.96 mmol, 31.00 mL, 2.00 eq), and stirred continuously at 110° C. for 4 hours. After completion the reaction, the reaction solution was evaporated to dry under reduced pressure, and the residue was dissolved in DCM (150 mL), followed by addition of water (150 mL). The aqueous phase was extracted with DCM (2×100 mL). The organic phases were combined and dried over anhydrous sodium sulfate, followed by suction-filtration and evaporation to dry under reduced pressure. The residue was recrystallized with EA (15 ml) to give WX006-5.

Step 5: Synthesis of Compound WX006-6

Acetic acid (53.19 mL), water (10.00 mL) and hydrogen peroxide (4.49 g, 39.61 mmol, 3.81 mL, 30% purity, 3.00 eq) were added into a pre-dried 250 mL three-necked flask, and the reaction temperature was controlled at 45° C. with an internal thermometer, followed by addition of WX006-5 (4.5 g, 13.20 mmol, 1.00 eq) in portions. The temperature was controlled below 55° C., and the reaction was carried out at this temperature for 30 minutes. After 30-minutes reaction, the reaction solution was cooled to room temperature, followed by addition of 20 mL of saturated sodium sulfite solution. No blue color was detected by the potassium iodide starch paper. After rotary evaporation under reduced pressure, the residue was dissolved in 100 mL of water, and adjusted to pH 10 with ammonia hydroxide, followed by extraction with dichloromethane (2×150 mL). The organic phases were combined and dried over anhydrous sodium sulfate, followed by rotary evaporation under reduced pressure. The crude product was purified by silica gel column chromatography (EA:PE=1:10-1:2) to give WX006-6.

Step 6: Synthesis of Compound WX006-7

WX006-6 (3.85 g, 12.47 mmol, 1.00 eq), lithium hydroxide (895.97 mg, 37.41 mmol, 3.00 eq) and tetrahydrofuran (38.00 mL) and water (38.00 mL) were added into a pre-dried 250 mL round bottom flask. The clear solution was stirred at 25° C. for 2 hours, and adjusted to pH 4-5 with 2N hydrochloric acid, followed by extraction with chloroform: isopropyl alcohol (3:1, 5×50 mL). The organic phases were combined, and dried over anhydrous sodium sulfate, followed by suction-filtration and rotary evaporation to give WX006-7. m/z=281.1 [M+1].

Step 7: Synthesis of Compound WX006-8

WX006-7 (2.06 g, 7.34 mmol, 1.00 eq) was added into a pre-dried 100 mL round bottom flask, and charged with nitrogen gas three times, followed by addition of dichloromethane (54.00 mL). Afterwards, oxalyl chloride (1.86 g, 14.68 mmol, 1.29 mL, 2.00 eq) and N,N-dimethylformamide (53.65 mg, 734.00 μmol, 56.47 μL, 0.10 eq) were slowly added dropwise thereto under nitrogen atmosphere. After completion of the dropwise addition, the reaction was carried out at 25° C. for 1 hour, followed by rotary evaporation with water pump. When the volume of the solution was reduced to about one-third of its original volume, 10 mL of anhydrous dichloromethane was added. Such procedures were repeated for three times to give a solution of WX006-8 in dichloromethane for direct use in the next reaction. m/z=295.1 [M+14].

Step 8: Synthesis of Compound WX006-9

A 100 mL round bottom flask containing WX006-8 (1.08 g, 3.61 mmol, 1.00 eq) was charged with nitrogen gas three times, followed by addition of dichloromethane (30 mL) and diisopropylethylamine (699.93 mg, 5.42 mmol, 943.30 μL, 1.5 eq). WXBB-3 (816.03 mg, 3.79 mmol, 1.05 eq) was added thereto under nitrogen atmosphere, and the clear solution was reacted at 25° C. for 0.5 hour. The product was re-dissolved with dichloromethane (20 mL), and extracted with water of pH=2 (3×30 mL). Afterwards, the aqueous phase was adjusted to pH=10 and extracted with dichloromethane (3×50 mL). The organic phases were combined, and dried over anhydrous sodium sulfate, followed by suction-filtration and evaporation to dry to give WX006-9. m/z=478.2 [M+1].

Step 9: Synthesis of Compound WX006

WX006-9 (0.3 g, 627.72 μmol, 1.00 eq), 3-pyridine boronic acid (154.32 mg, 1.26 mmol, 2.00 eq), palladium acetate (14.09 mg, 62.77 μmol, 0.10 eq), n-butylbis(1-adamantyl)phosphine (22.51 mg, 62.77 μmol, 0.10 eq) and potassium carbonate (260.27 mg, 1.88 mmol, 3.00 eq) were added into a pre-dried 10 mL vial, and charged with nitrogen gas three times, followed by addition of water (0.5 mL) and dioxane (5 mL). The reaction system was placed in an oil bath at 90° C. under nitrogen atmosphere, and stirred for 2 hours. The reaction solution was evaporated to dry, and purified by short silica gel column (100-200 mesh) to give WX006. $^1$H NMR (400 MHz, CHLOROFORM-d) δ ppm 0.59-0.67 (m, 2H) 0.73-0.83 (m, 2H) 1.73 (ddd, J=13.34, 8.38, 4.96 Hz, 1H) 1.86-2.07 (m, 4H) 3.03 (br t, J=6.28 Hz, 2H) 4.44 (br t, J=5.95 Hz, 2H) 6.53 (s, 1H) 7.16 (s, 1H) 7.21-7.26 (m, 1H) 7.32 (d, J=11.91 Hz, 1H) 7.85 (t, J=8.05 Hz, 1H) 8.05 (d, J=7.72 Hz, 1H) 8.17 (d, J=7.06 Hz, 1H) 8.31 (d, J=8.38 Hz, 1H) 8.46 (d, J=1.76 Hz, 1H) 8.57 (dd, J=4.52, 1.65 Hz, 1H) 8.99 (br d, J=13.89 Hz, 1H).

Example 007: WX007

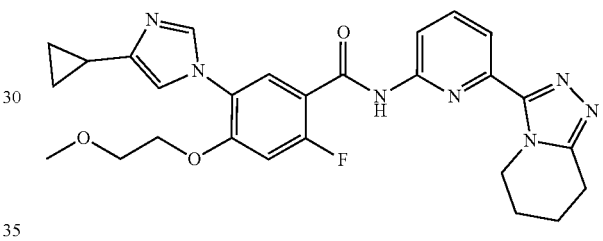

Synthetic Route:

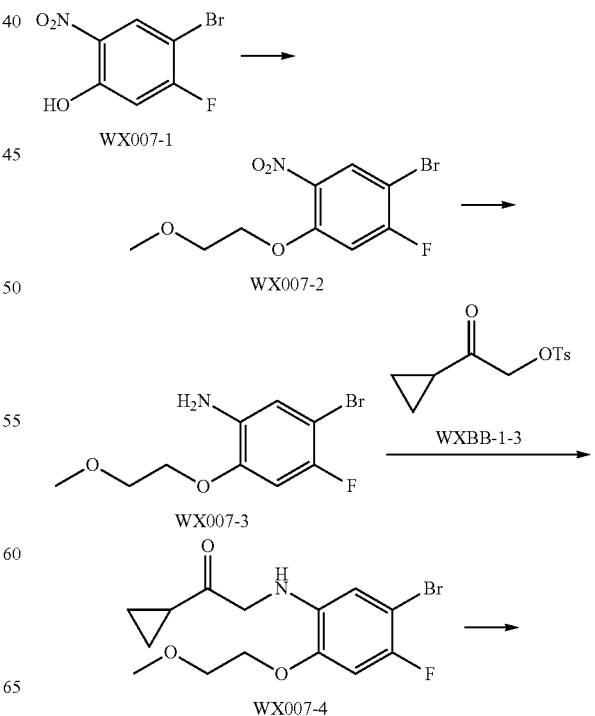

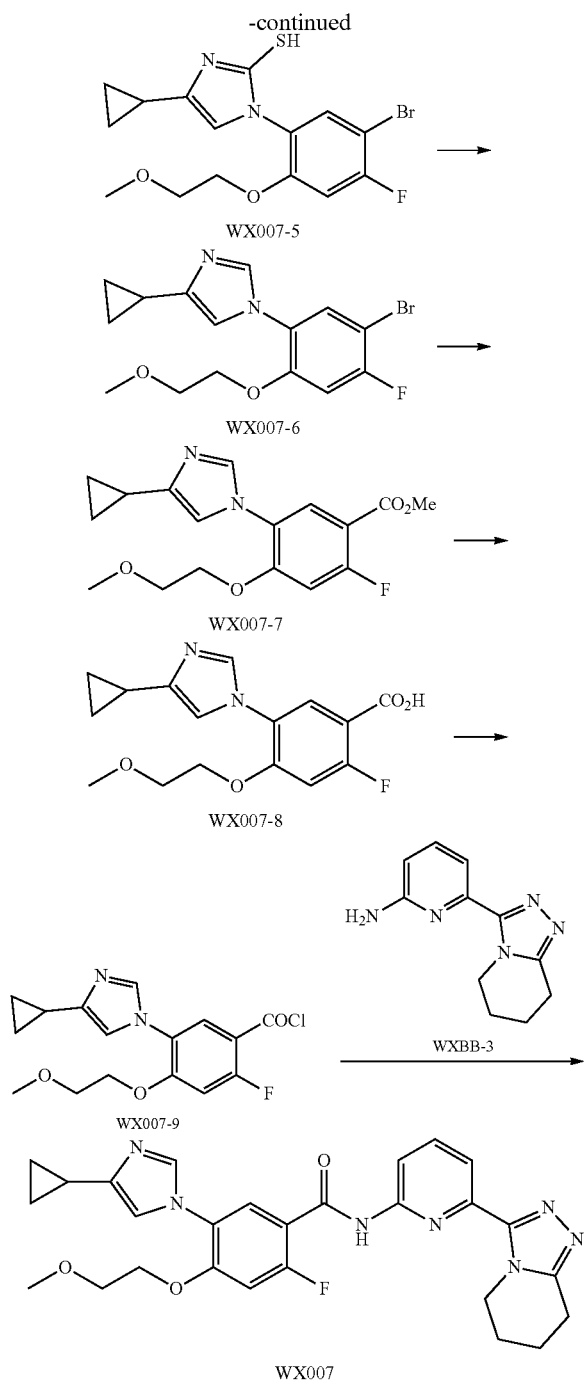

crude product was purified by a flash silica gel column (EA:PE=1:10-1:4) to give WX007-2. ¹H NMR (400 MHz, CHLOROFORM-d) δ ppm 3.41 (s, 3H) 3.73-3.82 (m, 2H) 4.14-4.28 (m, 1H) 4.14-4.28 (m, 1H) 6.93 (d, J=9.92 Hz, 1H) 8.10 (d, J=7.28 Hz, 1H).

Step 2: Synthesis of Compound WX007-3

WX007-2 (22.3 g, 75.83 mmol, 1.00 eq), Fe powder (12.71 g, 227.49 mmol, 3 eq), ammonium chloride (4.46 g, 83.41 mmol, 2.92 mL, 1.10 eq), water (130 mL) and ethanol (400 mL). were added into a pre-dried 1000 mL eggplant-shaped flask. The reaction solution was refluxed at 80° C. for 6 hours. The reaction solution was passed through diatomite, followed by rotary evaporation to dry and dissolution in dichloromethane (100 mL) and water (80 mL). The aqueous phase was extracted with dichloromethane (2×50 mL). The organic phases were combined, washed with saturated brine (2×100 mL), dried, filtered and concentrated to give a crude product. WX007-3 was given by flash silica gel column (ethyl acetate:petroleum ether=1:8-1:1). ¹H NMR (400 MHz, CHLOROFORM-d) δ ppm 3.41 (s, 3H) 3.71-3.77 (m, 4H) 4.06-4.10 (m, 2H) 6.62 (d, J=9.92 Hz, 1H) 6.80 (d, J=6.84 Hz, 1H).

Step 3: Synthesis of Compound WX007-4

WX007-3 (12.64 g, 47.86 mmol, 1.00 eq), WXBB-10 (13.39 g, 52.65 mmol, 1.10 eq) and toluene (120 mL) were added into a pre-dried 500 mL reaction flask. The temperature of the reaction was raised to 100° C., followed by addition of diisopropylethylamine (12.37 g, 95.72 mmol, 16.67 mL, 2.00 eq). The reaction was carried out at 100° C. for 10 hour, followed by rotary evaporation to dry and purification by column chromatography (ethyl acetate:petroleum ether=0-1:10) to give WX007-4. m/z=346.1, 348.1 [M+1].

Step 4: Synthesis of Compound WX007-5

WX007-4 (14.85 g, 42.90 mmol, 1.00 eq) and glacial acetic acid (200 mL) were added into a pre-dried 500 mL round bottom flask, followed by addition of potassium thiocyanate (8.34 g, 85.79 mmol, 8.34 mL, 2.00 eq). The temperature of the reaction was raised to 110° C. and reacted for 3 hours. After completion of the reaction, the reaction solution was rotary evaporated to dry under reduced pressure, and the residue was re-dissolved in dichloromethane (60 mL), followed by addition of water (60 mL). The aqueous phase was extracted with dichloromethane (2×40 mL). The organic phases were combined, washed with saturated brine (2×50 mL) and dried over anhydrous sodium sulfate, followed by suction-filtration, rotary evaporation and purification by column chromatography (ethyl acetate: petroleum ether=1:10-1:1) to give WX007-5. m/z=387.1, 389.1 [M+1].

Step 5: Synthesis of Compound WX007-6

Glacial acetic acid (100 mL), water (18 mL) and hydrogen peroxide (9.39 g, 82.80 mmol, 7.95 mL, 30% purity, 3.00 eq) were added into a pre-dried 250 mL three-necked flask, and the reaction temperature was controlled at 45° C. with an internal thermometer, followed by addition of WX007-5 (10.69 g, 27.60 mmol, 1.00 eq) in portions. The temperature was controlled below 55° C., and the reaction was carried out at this temperature for 30 minutes. The reaction was cooled to room temperature, followed by addition of 20 mL of saturated sodium sulfite solution. No blue color was detected by the potassium iodide starch paper. After rotary evaporation under reduced pressure, the residue was dissolved in 100 mL of water, and adjusted to pH 10 with ammonia hydroxide, followed by extraction with dichloromethane (2×150 mL). The organic phases were combined Step 1: Synthesis of Compound WX007-2

2-Bromo-1-methoxyethane (20 g, 84.75 mmol, 1 eq) and N,N-dimethylformamide (150 mL) were added into a pre-dried 250 mL round bottom flask, followed by addition of WX007-1 (14.13 g, 101.70 mmol, 9.55 mL, 1.2 eq) and potassium carbonate (23.43 g, 169.49 mmol, 2 eq). The system was reacted at 50° C. for 20 hours. The reaction solution was evaporated to dry and re-dissolved in ethyl acetate (100 mL) and water (100 mL). The organic phase and the aqueous phase were separated, and the aqueous phase was extracted with ethyl acetate (3×50 mL). The organic phases were combined, washed with saturated brine (2×150 mL) and dried over anhydrous sodium sulfate, followed by suction-filtration to give a crude product. The and dried over anhydrous sodium sulfate, followed by rotary evaporation under reduced pressure to give WX007-6. m/z=355.1, 357.1 [M+1].

Step 6: Synthesis of Compound WX007-7

WX007-6 (7.1 g, 19.99 mmol, 1.00 eq) and triethylamine (4.05 g, 39.98 mmol, 5.56 mL, 2.00 eq) were added into a 250 mL hydrogenation flask followed by addition of methanol (100 mL) and Pd(dppf)Cl$_2$ (2.19 g, 3.00 mmol, 0.15 eq), and charged with carbon monoxide three times and pressurized to 50 psi. The reaction vessel was placed in an oil bath at 70° C. (external temperature) and stirred for 10 hours. The reaction solution was rotary evaporated and isolated by column chromatography (ethyl acetate:petroleum ether=1: 10-1:1) to give WX007-7. $^1$H NMR (400 MHz, CHLOROFORM-d) δ ppm 0.70-0.78 (m, 2H) 0.81-0.89 (m, 2H) 1.81-1.91 (m, 1H) 3.36 (s, 3H) 3.66-3.73 (m, 2H) 3.88 (s, 3H) 4.14-4.21 (m, 2H) 6.78 (d, J=11.69 Hz, 1H) 6.90 (s, 1H) 7.66 (s, 1H) 7.84 (d, J=7.50 Hz, 1H).

Step 7: Synthesis of Compound WX007-8

WX007-7 (0.6 g, 1.79 mmol, 1.00 eq), lithium hydroxide (128.94 mg, 5.38 mmol, 3.00 eq), tetrahydrofuran (12 mL) and water (12 mL) were added into a pre-dried 100 mL flask. The clear solution was stirred at 25° C. for 1 hour. After completion of the reaction, the reaction solution was directly rotary evaporated with water pump, followed by addition of toluene (2×10 mL) to remove the residual water left by the rotary evaporation to give WX007-8. m/z=321.2 [M+1].

Step 8: Synthesis of Compound WX007-9

WX007-8 (574.83 mg, 1.79 mmol, 1.00 eq) was added into a pre-dried 100 mL round bottom flask, and displaced with nitrogen three times, followed by addition of dichloromethane (20 mL). Afterwards, oxalyl chloride (455.57 mg, 3.59 mmol, 314.19 μL, 2.00 eq) and N,N-dimethylformamide (13.12 mg, 179.46 μmol, 13.81 μL, 0.10 eq) were slowly added dropwise thereto under nitrogen atmosphere. After completion of the dropwise addition, the reaction was carried out at 25° C. for 1 hour, followed by rotary evaporation with water pump. When the volume of the solution was reduced to about one-third of its original volume, 20 mL of anhydrous dichloromethane was added. Such procedures were repeated for three times to give a solution of WX007-9 in dichloromethane for direct use in the next reaction. m/z=335.2 [M+14].

Step 9: Synthesis of Compound WX007

A 100 mL round bottom flask containing WX007-9 (721.80 mg, 2.13 mmol, 1.05 eq) was charged with nitrogen gas three times, followed by addition of dichloromethane (30 mL) and diisopropylethylamine (393.39 mg, 3.04 mmol, 530.17 μL, 1.5 eq). WXBB-3 (687.43 mg, 2.03 mmol, 1.00 eq) was added thereto under nitrogen atmosphere, and the clear solution was reacted at 25° C. for 10 hours, followed by extraction with water of pH=2 (3×30 mL). Afterwards, the aqueous phase was adjusted to pH=10 and extracted with dichloromethane (3×50 mL). The organic phases were combined, and dried over anhydrous sodium sulfate, followed by suction-filtration and rotary evaporation to dry to give a crude product. The crude product was isolated by rapid preparation to give WX007 (42.7 mg, 82.50 μmol, 4.07% yield). $^1$H NMR (400 MHz, METHANOL-d4) δ ppm 0.78-0.91 (m, 2H) 1.02-1.10 (m, 2H) 1.98-2.13 (m, 5H) 3.05 (t, J=6.40 Hz, 2H) 3.41 (s, 3H) 3.77 (dd, J=5.14, 3.39 Hz, 2H) 4.34-4.42 (m, 2H) 4.59 (t, J=5.96 Hz, 2H) 7.32 (d, J=12.42 Hz, 1H) 7.46 (s, 1H) 7.91 (d, J=7.15 Hz, 1H) 7.99-8.06 (m, 2H) 8.34 (d, J=7.78 Hz, 1H) 8.66 (s, 1H).

Example 008: WX008

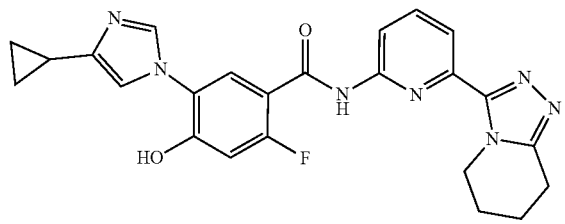 [SMILES: O=C(Nc1cccc(-c2nnc3n2CCCC3)n1)c1cc(-n2cnc(C3CC3)c2)c(O)cc1F]

Synthetic Route:

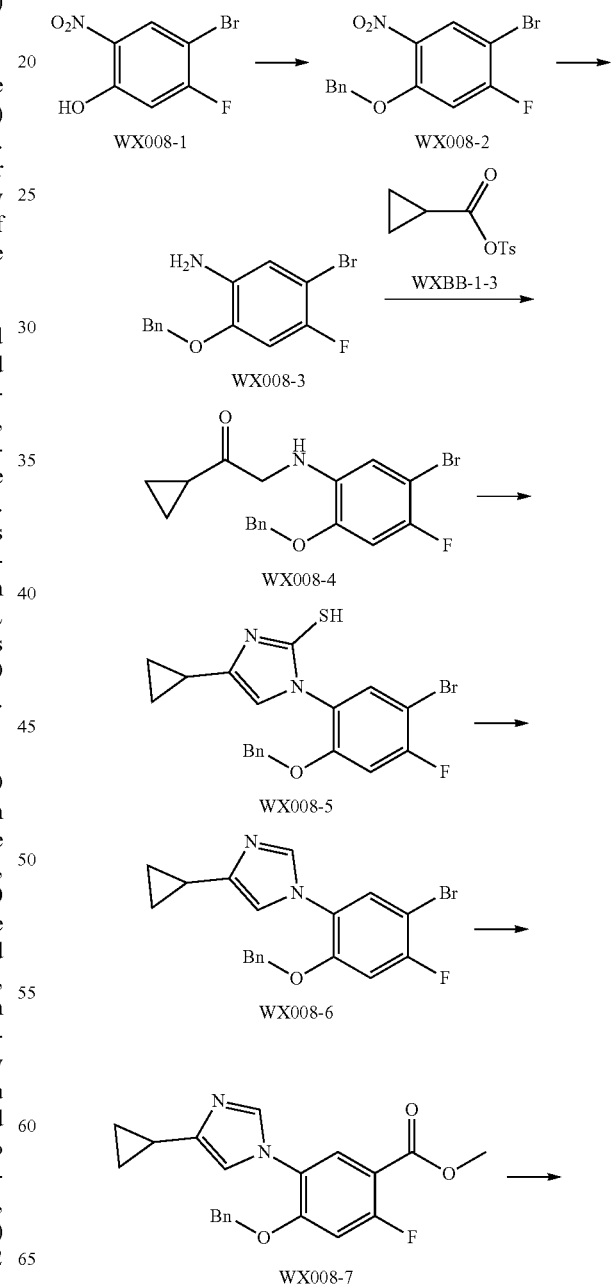

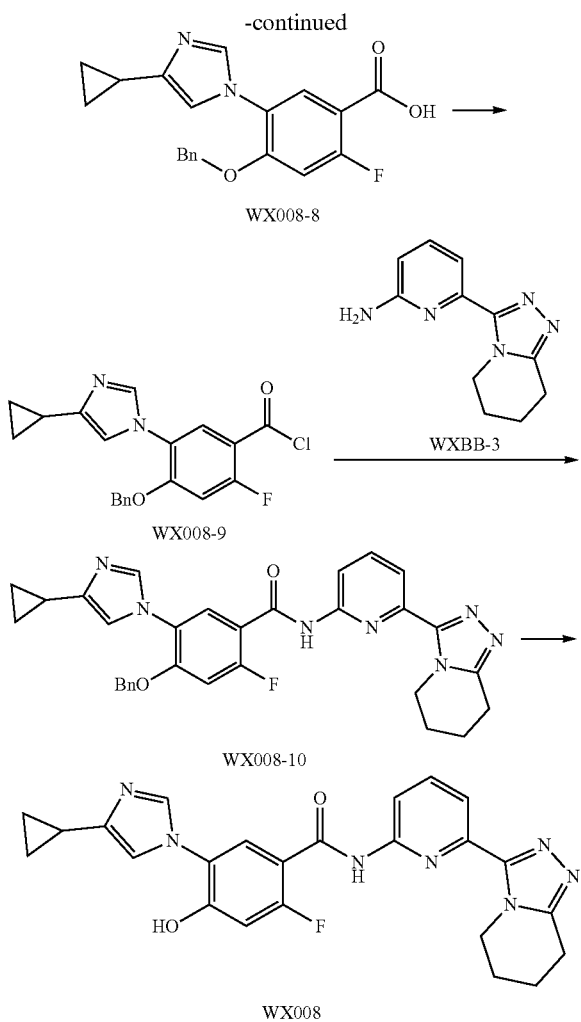

Step 1: Synthesis of Compound WX008-2

WX008-1 (28 g, 118.65 mmol, 1 eq) was dissolved in anhydrous DMF (200 mL), followed by addition of K₂CO₃ (32.80 g, 237.29 mmol, 2 eq) and BnBr (24.35 g, 142.38 mmol, 16.91 mL, 1.2 eq). The mixture was stirred at 20° C. for 16 hours. The reaction solution was poured into water (600 mL), and extracted with EA (300 mL*2). The organic phase was washed with water (300 mL) and saturated brine (300 mL) and dried over anhydrous sodium sulfate, followed by filtration. The filtrate was evaporated to dry under reduced pressure. Slurrying of the crude product was carried out with PE/EA=5/1 (120 mL) at 20° C. for 0.5 hour, followed by filtration. The filter cake was suction-filtered to dryness under reduced pressure to give WX008-2. $^1$H NMR (400 MHz, CHLOROFORM-d) δ=8.20 (d, J=7.3 Hz, 1H), 7.50-7.38 (m, 5H), 6.94 (d, J=9.8 Hz, 1H), 5.25 (s, 2H).

Step 2: Synthesis of Compound WX008-3

WX008-2 (26.5 g, 81.26 mmol, 1 eq) was dissolved in MeOH (500 mL), followed by addition of NiCl.6H₂O (69.53 g, 292.53 mmol, 3.6 eq) in portions, and addition of NaBH₄ (15.37 g, 406.26 mmol, 5 eq) in portions at 0° C. The mixture was stirred at 25° C. for 0.5 hours, followed by the addition of saturated ammonium chloride solution (500 mL). The reaction solution was rotary evaporated to remove the methanol, followed by addition of EA (500 mL), and stirred for 10 minutes. The insoluble solid was filtered off. The filtrate was separated to collect the organic phase, and the aqueous phase was extracted with EA (250 mL). The organic phases were combined, washed with saturated brine (250 mL) and dried over anhydrous sodium sulfate, followed by filtration. The filtrate was rotary evaporated to dry under reduced pressure to give WX008-3. $^1$H NMR (400 MHz, CHLOROFORM-d) δ=7.43 (br s, 5H), 6.87 (br d, J=5.0 Hz, 1H), 6.70 (br d, J=9.5 Hz, 1H), 5.07 (br s, 2H), 3.75 (br s, 2H).

Step 3: Synthesis of Compound WX008-4

WX008-3 (22 g, 63.81 mmol, 1 eq) (purity: 85.59%) was added to anhydrous toluene (200 mL), followed by addition of WXBB-1-3 (17.04 g, 67.00 mmol, 1.05 eq) and DIEA (16.49 g, 127.62 mmol, 22.23 mL, 2 eq). The mixture was stirred at 100° C. for 16 hours. The reaction solution was rotary evaporated to dry, followed by addition of water (200 mL) and extraction with EA (200 mL*2). The organic phase was washed with saturated brine (100 mL), and dried over anhydrous sodium sulfate, followed by filtration. The filtrate was rotary evaporated to dry under reduced pressure. PE/EA=5/1 (60 mL) was added to the crude product, and slurrying was carried out at 20° C. for 0.5 hour, followed by filtration. The filter cake was rotary evaporated to dry under reduced pressure to give WX008-4. $^1$H NMR (400 MHz, CHLOROFORM-d) δ=7.38-7.23 (m, 5H), 6.58 (d, J=9.8 Hz, 1H), 6.48 (d, J=6.8 Hz, 1H), 5.02 (br d, J=4.8 Hz, 1H), 5.00 (s, 2H), 4.06 (d, J=5.0 Hz, 2H), 1.98-1.88 (m, 1H), 1.08 (quin, J=3.8 Hz, 2H), 0.96-0.87 (m, 2H)

Step 4: Synthesis of Compound WX008-5

WX008-4 (15 g, 35.58 mmol, 1 eq) (purity: 89.71%) was added to AcOH (120 mL), followed by addition of KSCN (6.91 g, 71.15 mmol, 6.91 mL, 2 eq). The mixture was stirred at 110° C. for 4 hours under nitrogen atmosphere. The reaction solution was cooled to room temperature, poured into water (300 mL), and stirred for 15 minutes with the precipitation of solids, followed by filtration. The filter cake was rotary evaporated to dry under reduced pressure to give WX008-5. $^1$H NMR (400 MHz, CHLOROFORM-d) δ=11.56 (br s, 1H), 7.60 (d, J=7.3 Hz, 1H), 7.30-7.21 (m, 5H), 6.79 (d, J=9.8 Hz, 1H), 6.31 (s, 1H), 5.02 (s, 2H), 1.67-1.58 (m, 1H), 0.84-0.77 (m, 2H), 0.61-0.53 (m, 2H).

Step 5: Synthesis of Compound WX008-6

WX008-5 was dissolved in a mixed solution of AcOH (150 mL) and H₂O (15 mL), followed by dropwise addition of H₂O₂ (12.97 g, 114.42 mmol, 10.99 mL, 30% purity, 3.22 eq) and the system was stirred at 45° C. for 0.5 hour. After cooling to room temperature, the reaction solution was slowly added to a solution of sodium sulfate (30 g) in water (30 mL), followed by extraction with EA (300 mL*2). The organic phase was washed with saturated sodium bicarbonate (300 mL) and dried over anhydrous sodium sulfate, followed by filtration. The filtrate was rotary evaporated to dry. The crude product was purified by column chromatography (EA/PE=0-10% to 20%) to give WX008-6. $^1$H NMR (400 MHz, CHLOROFORM-d) δ=7.64 (d, J=1.0 Hz, 1H), 7.48 (d, J=7.0 Hz, 1H), 7.42-7.34 (m, 3H), 7.33-7.29 (m, 2H), 6.94-6.88 (m, 2H), 5.11 (s, 2H), 1.95-1.86 (m, 1H), 0.92-0.86 (m, 2H), 0.83-0.77 (m, 2H).

Step 6: Synthesis of Compound WX008-7

WX008-6 (6 g, 14.56 mmol, 1 eq) (purity 93.95%) was dissolved in anhydrous MeOH (100 mL), followed by addition of Pd(dppf)Cl₂ (1.07 g, 1.46 mmol, 0.1 eq) and Et₃N (2.95 g, 29.11 mmol, 4.05 mL, 2 eq). The system was stirred at 80° C. for 4 hours under CO atmosphere (50 psi). The reaction solution was filtered, and the filtrate was rotary evaporated to dry. The crude product was purified by column chromatography (EA/PE=0-10%-20%-40%) to give WX008-7. $^1$H NMR (400 MHz, CHLOROFORM-d) δ=7.92

(d, J=7.5 Hz, 1H), 7.67 (d, J=0.8 Hz, 1H), 7.44-7.31 (m, 5H), 6.93 (d, J=0.8 Hz, 1H), 6.87 (d, J=11.8 Hz, 1H), 5.19 (s, 2H), 3.94 (s, 3H), 1.96-1.86 (m, 1H), 0.93-0.86 (m, 2H), 0.84-0.78 (m, 2H).

Step 7: Synthesis of Compound WX008-8

WX008-7 (2.7 g, 7.37 mmol, 1 eq) was dissolved in anhydrous THF (20 mL), followed by addition of a solution of LiOH (530 mg, 22.13 mmol, 3 eq) in H₂O (10 mL). The mixture was stirred at 20° C. for 1 hour. The reaction solution was directly dried to give a crude product. Slurrying of the crude product was carried out with (DCM:MeOH=10:1, 44 mL) at 20° C. for 0.5 hour, followed by filtration. The filtrate was rotary evaporated to dry under reduced pressure to give WX008-8. $^1$H NMR (400 MHz, DMSO-d$_6$) δ ppm 0.59-0.65 (m, 2H) 0.69-0.78 (m, 2H) 1.73-1.83 (m, 1H) 5.15 (s, 2H) 6.99 (d, J=11.80 Hz, 1H) 7.08 (s, 1H) 7.33 (br dd, J=7.78, 4.77 Hz, 1H) 7.36 (d, J=1.51 Hz, 2H) 7.37 (br s, 2H) 7.57 (d, J=7.78 Hz, 1H) 7.64 (s, 1H).

Step 8: Synthesis of Compound WX008-9

Compound WX008-8 (690 mg, 1.96 mmol, 1 eq) was added into a pre-dried 50 mL round bottom flask, and charged with nitrogen gas three times, followed by addition of dichloromethane (50.00 mL). Afterwards, oxalyl chloride (497.12 mg, 3.92 mmol, 342.84 μL, 2 eq) and N,N-dimethylformamide (14.31 mg, 195.82 μmol, 15.07 μL, 0.1 eq) were slowly added dropwise thereto at 25° C. under nitrogen atmosphere. After completion of the dropwise addition, the reaction was carried out at 25° C. for 1 hour, followed by rotary evaporation with water pump. When the volume of the solution was reduced to about one-third of its original volume, 50 mL of anhydrous dichloromethane was added. Such procedures were repeated for three times to give a solution of WX008-9 (0.726 g) in dichloromethane for direct use in the next reaction. MS: m/z=367 [methyl ester M+1].

Step 9: Synthesis of Compound WX008-10

Dichloromethane (30 mL) was added into a round bottom flask containing Compound WX008-9 (0.726 g, 1.96 mmol, 1 eq), and a solution of Compound WXBB-3 (442.52 mg, 2.06 mmol, 1.05 eq) in dichloromethane (20 mL) solution was rapidly dropwise added into the reaction flask, followed by addition of diisopropylethylamine (278.34 mg, 2.15 mmol, 375.13 μL, 1.1 eq) under nitrogen atmosphere. The clear solution was reacted at 25° C. for 1 hour. The reaction solution was concentrated, and the product was then re-dissolved with dichloromethane (100 mL), adjusted to pH=2-3 with 1 M aqueous hydrochloric acid solution. The reaction solution was fully stirred, and then allowed to stand for separation. The aqueous phase was collected and adjusted to pH=8-9 with sodium bicarbonate with precipitation of solids, followed by filtration to give the solids. The solids were dissolved with dichloromethane and dried over anhydrous sodium sulfate, followed by filtration. The filtrate was concentrated to give WX008-10 (0.8 g, 1.30 mmol, 66.17% yield, 89% purity). $^1$H NMR (400 MHz, CHLOROFORM-d) δ=8.89 (br d, J=14.8 Hz, 1H), 8.28 (d, J=8.2 Hz, 1H), 8.07 (d, J=8.2 Hz, 1H), 8.00 (d, J=7.5 Hz, 1H), 7.82 (t, J=7.9 Hz, 1H), 7.65 (d, J=0.9 Hz, 1H), 7.36-7.30 (m, 2H), 7.30-7.25 (m, 2H), 6.90 (s, 1H), 6.84 (d, J=13.5 Hz, 1H), 5.15 (s, 2H), 4.41 (t, J=6.0 Hz, 2H), 3.02 (t, J=6.4 Hz, 2H), 2.04-1.95 (m, 2H), 1.94-1.88 (m, 2H), 1.83 (br dd, J=4.1, 9.2 Hz, 1H), 0.87-0.79 (m, 2H), 0.76-0.69 (m, 2H).

Step 10: Synthesis of Compound WX008

Compound WX008-9 (0.8 g, 1.46 mmol, 1 eq) was dissolved in methanol (50 mL), followed by addition of palladium on carbon (0.8 g, 50% purity). The mixture was stirred at 25° C. for 2 hours under hydrogen atmosphere (50 Psi). The reaction solution was filtered with diatomite. The filter cake was sequentially washed with methanol (500 mL), dichloromethane (500 mL), tetrahydrofuran (500 mL) and methanol (500 mL). The filtrate was concentrated under reduced pressure to give a crude product. Slurrying of the crude product was carried out with methanol (10 mL), followed by filtration. The filtrate was concentrated to give WX008 (0.15 g, 319.93 μmol, 21.98% yield, 98% purity). $^1$H NMR (400 MHz, DMSO-d6) δ=10.66 (s, 1H), 8.16 (d, J=7.9 Hz, 1H), 7.98 (t, J=7.9 Hz, 1H), 7.85 (d, J=7.5 Hz, 1H), 7.80 (s, 1H), 7.69 (d, J=7.5 Hz, 1H), 7.23 (d, J=0.9 Hz, 1H), 6.90 (d, J=11.9 Hz, 1H), 4.47 (t, J=5.8 Hz, 2H), 2.91 (t, J=6.3 Hz, 2H), 1.92 (br d, J=4.6 Hz, 2H), 1.88-1.79 (m, 3H), 0.82-0.75 (m, 2H), 0.71-0.64 (m, 2H).

Example 009: WX009

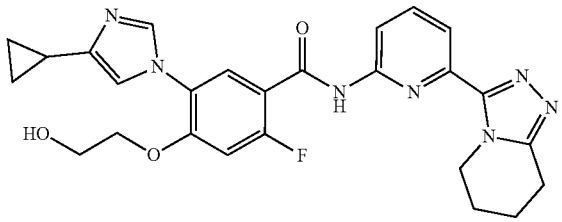 [SMILES: O=C(Nc1cccc(-c2nnc3n2CCCC3)n1)c1cc(-n2cnc(C3CC3)c2)c(OCCO)cc1F]

Synthetic Route:

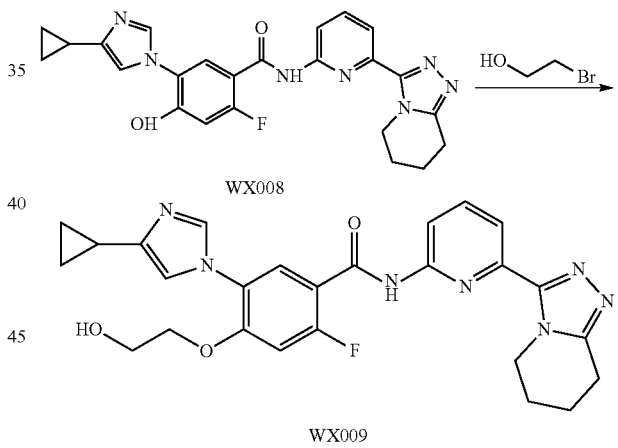

Step 1: Synthesis of Compound WX009

Compound WX008 (200 mg, 435.28 μmol, 1 eq), potassium carbonate (120.32 mg, 870.56 μmol, 2 eq), acetone (50 mL) and 2-bromoethanol (81.59 mg, 652.92 μmol, 46.36 μL, 1.5 eq) were added into a pre-dried 40 mL vial. The reaction solution was stirred at 75° C. for 16 hours. The reaction solution was concentrated under reduced pressure with an oil pump to give a crude solid. The solid crude product was dissolved in N,N-dimethylformamide (8 mL), and then isolated and purified by rapid preparation (water (10 mM NH₄HCO₃)—CAN) to give Compound WX009. $^1$H NMR (400 MHz, METHANOL-d4) δ=8.32 (d, J=8.2 Hz, 1H), 8.02-7.88 (m, 4H), 7.23 (m, 2H), 4.57 (t, J=5.8 Hz, 2H), 4.30-4.22 (m, 2H), 3.90 (t, J=4.4 Hz, 2H), 3.07-2.99 (m, 2H), 2.06 (br d, J=4.2 Hz, 2H), 2.00 (br s, 2H), 1.89 (br s, 1H), 0.87 (br d, J=6.0 Hz, 2H), 0.75 (br s, 2H).

Example 010: WX010

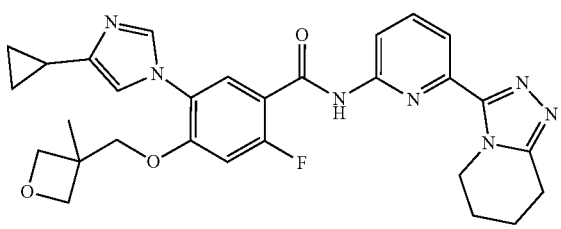 [SMILES: CC1(COc2cc(F)c(C(=O)Nc3cccc(-c4nnc5n4CCCC5)n3)cc2-n2cnc(C3CC3)c2)COC1]

Synthetic Route:

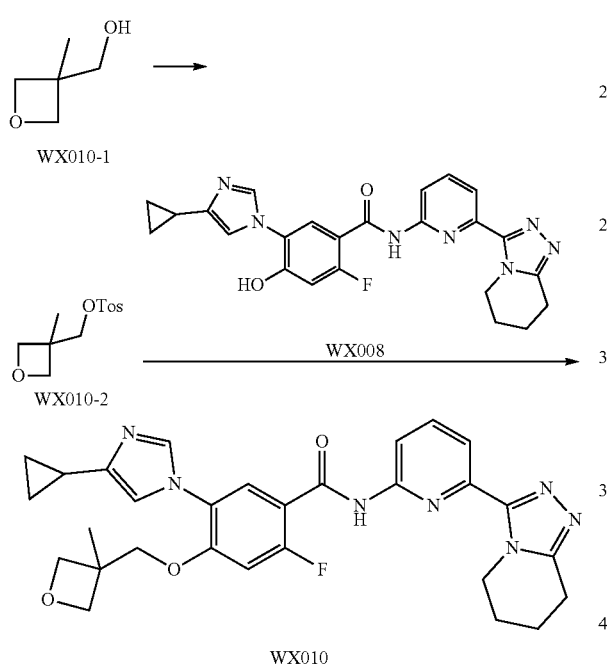

Step 1: Synthesis of Compound WX010-2

Compound WX010-1 (200 mg, 1.96 mmol, 194.17 μL, 1 eq) and dichloromethane (5 mL) were added into a pre-dried 40 mL reaction vial, followed by sequential addition of triethylamine (297.24 mg, 2.94 mmol, 408.85 μL, 1.5 eq), dimethylaminopyridine (23.92 mg, 195.83 μmol, 0.1 eq) and p-toluenesulfonyl chloride (448.01 mg, 2.35 mmol, 1.2 eq). The reaction solution was stirred at 25° C. for 3 hours. A saturated aqueous solution of ammonium chloride (10 mL) was added to the reaction solution, and extracted with dichloromethane (10 mL×3). The organic phases were combined, dried over anhydrous sodium sulfate and concentrated under reduced pressure to give a crude product. The crude product was purified by thin layer chromatography silica gel plate (petroleum ether:ethyl acetate=3:1) to give WX010-2. $^1$H NMR (400 MHz, CHLOROFORM-d) δ=7.82 (d, J=8.2 Hz, 2H), 7.37 (d, J=7.9 Hz, 2H), 4.44-4.30 (m, 4H), 4.12 (s, 2H), 2.47 (s, 3H), 1.32 (s, 3H).

Step 2: Synthesis of Compound WX010

Compound WX008 (100 mg, 217.64 μmol, 1 eq), potassium carbonate (45.12 mg, 326.46 μmol, 1.5 eq), N,N-dimethylformamide (4 mL) and Compound WX010-2 (66.94 mg, 261.17 μmol, 1.2 eq) were sequentially added into a pre-dried 40 mL reaction vial. The reaction solution was stirred at 80° C. for 16 hours. The reaction solution was isolated and purified by rapid preparation (water (10 mM NH$_4$HCO$_3$)-ACN) to give WX010. 1H NMR (400 MHz, CHLOROFORM-d) δ=8.99 (d, J=14.8 Hz, 1H), 8.37 (d, J=8.2 Hz, 1H), 8.17 (d, J=8.2 Hz, 1H), 8.09 (d, J=7.7 Hz, 1H), 7.91 (t, J=8.0 Hz, 1H), 7.63 (d, J=1.3 Hz, 1H), 6.98-6.89 (m, 2H), 4.54-4.49 (m, 2H), 4.48 (s, 4H), 4.23 (s, 2H), 3.11 (t, J=6.4 Hz, 2H), 2.09-2.08 (m, 2H), 2.06-2.00 (m, 2H), 1.99-1.91 (m, 1H), 1.39 (s, 3H), 0.90-0.88 (m, 2H), 0.82-0.79 (m, 2H).

Example 011: WX011

Synthetic Route:

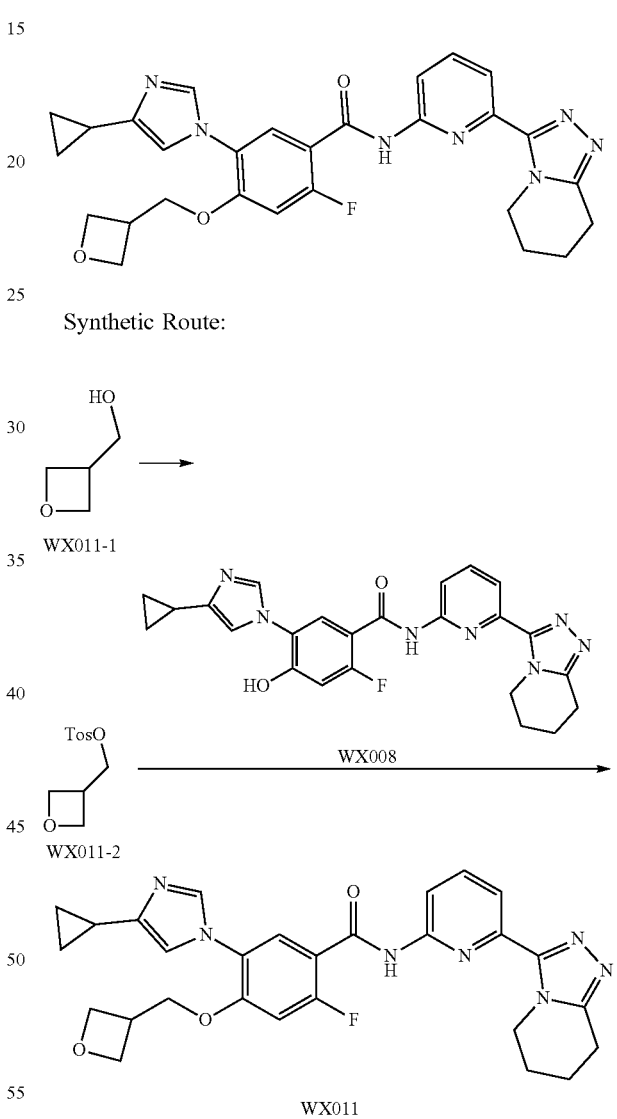

Step 1: Synthesis of Compound WX011-2

Compound WX011-1 (200 mg, 2.27 mmol, 1 eq) and dichloromethane (5 mL) were added into a pre-dried 40 mL reaction flask, followed by triethylamine (344.56 mg, 3.41 mmol, 473.94 μL, 1.5 eq), dimethylaminopyridine (27.73 mg, 227.00 μmol, 0.1 eq) and p-toluenesulfonyl chloride 1 (519.34 mg, 2.72 mmol, 1.2 eq). The reaction solution was stirred at 25° C. for 16 hours. A saturated aqueous solution of ammonium chloride (20 mL) was added to the reaction solution, and extracted with dichloromethane (20 mL×3).

The organic phases were combined, dried over anhydrous sodium sulfate and concentrated under reduced pressure to give a crude product. The crude product was purified by thin layer chromatography silica gel plate (petroleum ether:ethyl acetate=3:1) to give WX011-2. $^1$H NMR (400 MHz, CHLOROFORM-d) δ=7.78 (d, J=8.0 Hz, 2H), 7.34 (d, J=8.0 Hz, 2H), 4.70 (dd, J=7.6, 6.4 Hz, 2H), 4.30 (t, J=6.4 Hz, 2H), 4.23 (d, J=76.8 Hz, 2H), 3.29-3.22 (m, 1H), 2.43 (s, 3H).

Step 2: Synthesis of Compound WX011

Compound WX008 (100 mg, 217.64 μmol, 1 eq) and N,N-dimethylformamide (4 mL) were added into a pre-dried 40 mL reaction vial, followed by sequential addition of potassium carbonate (45.12 mg, 326.46 μmol, 1.5 eq), potassium iodide (18.06 mg, 108.82 μmol, 0.5 eq) and Compound WX011-2 (63.28 mg, 261.17 μmol, 2.32 μL, 1.2 eq). The reaction solution was stirred at 80° C. for 16 hours. The reaction solution was filtered, separated and purified by rapid preparation. The reaction solution was separated and purified by rapid preparation to give WX011. 1H NMR (400 MHz, DMSO-d6) δ=10.83 (s, 1H), 8.17 (d, J=7.7 Hz, 1H), 8.00 (t, J=8.0 Hz, 1H), 7.87 (dd, J=0.8, 7.6 Hz, 1H), 7.80-7.74 (m, 2H), 7.40 (d, J=12.1 Hz, 1H), 7.24 (d, J=1.3 Hz, 1H), 4.68 (dd, J=6.2, 7.9 Hz, 2H), 4.47 (br t, J=5.7 Hz, 2H), 4.43-4.37 (m, 4H), 3.44-3.36 (m, 1H), 2.92 (t, J=6.3 Hz, 2H), 1.97-1.89 (m, 2H), 1.84 (br dd, J=5.2, 8.5 Hz, 3H), 0.81-0.75 (m, 2H), 0.68-0.63 (m, 2H).

Example 012: WX012

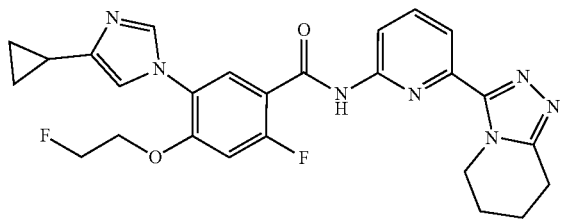 [SMILES: O=C(Nc1cccc(-c2nnc3n2CCCC3)n1)c1cc(-n2cnc(C3CC3)c2)c(OCCF)cc1F]

Synthetic Route:

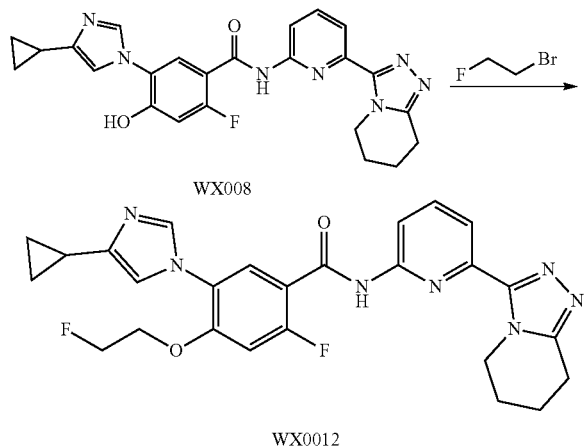

Step 1: Synthesis of Compound WX012

Compound WX008 (150 mg, 221.99 μmol, 1 eq), potassium carbonate (61.36 mg, 443.99 μmol, 2 eq), N,N-dimethylformamide (4 mL) and 1-bromo-2-fluoro-ethane (56.37 mg, 443.99 μmol, 30.91 μL, 2 eq) were sequentially added into a pre-dried 40 mL reaction flask. The reaction solution was stirred at 100° C. for 5 hours. The reaction solution was filtered through a filter to give a clear solution, which was isolated and purified by rapid preparation to give WX012. $^1$H NMR (400 MHz, CHLOROFORM-d) δ=8.98 (br d, J=14.8 Hz, 1H), 8.39-8.33 (m, 1H), 8.16 (d, J=8.2 Hz, 1H), 8.08 (dd, J=0.9, 7.7 Hz, 1H), 7.95-7.86 (m, 1H), 7.73 (d, J=1.1 Hz, 1H), 6.99 (d, J=1.1 Hz, 1H), 6.89 (d, J=13.2 Hz, 1H), 4.86-4.81 (m, 1H), 4.75-4.68 (m, 1H), 4.50 (t, J=6.1 Hz, 2H), 4.41-4.37 (m, 1H), 4.36-4.31 (m, 1H), 3.10 (t, J=6.4 Hz, 2H), 2.11-2.03 (m, 2H), 2.02-1.95 (m, 2H), 1.95-1.88 (m, 1H), 0.94-0.87 (m, 2H), 0.87-0.81 (m, 2H).

Example 013: WX013

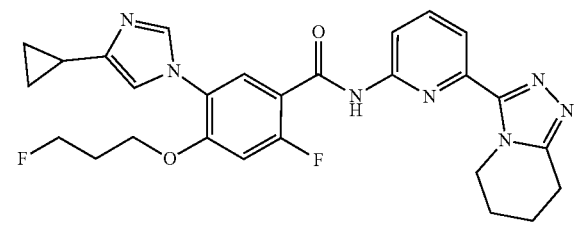 [SMILES: O=C(Nc1cccc(-c2nnc3n2CCCC3)n1)c1cc(-n2cnc(C3CC3)c2)c(OCCCF)cc1F]

Synthetic Route:

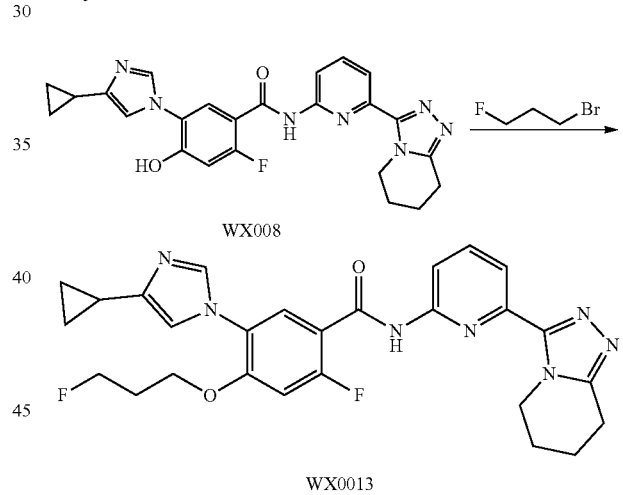

Step 1: Synthesis of Compound WX013

Compound WX008 (100 mg, 148.00 μmol, 1 eq), potassium carbonate (40.91 mg, 295.99 μmol, 2 eq), N,N-dimethylformamide (1 mL) and 1-bromo-3-fluoro-propane (41.73 mg, 295.99 μmol, 30.91 μL, 2 eq) were sequentially added into a pre-dried 40 mL reaction flask. The reaction solution was stirred at 90° C. for 2 hours. The reaction solution was filtered through a filter to give a clear solution. The clear solution was isolated and purified by rapid preparation to give WX013. $^1$H NMR (400 MHz, CHLOROFORM-d) δ=8.99 (br d, J=15.2 Hz, 1H), 8.37 (d, J=8.2 Hz, 1H), 8.15 (d, J=8.2 Hz, 1H), 8.08 (d, J=7.7 Hz, 1H), 7.90 (t, J=8.0 Hz, 1H), 7.67 (d, J=0.9 Hz, 1H), 6.96-6.86 (m, 2H), 4.64 (t, J=5.5 Hz, 1H), 4.56-4.47 (m, 3H), 4.25 (t, J=6.1 Hz, 2H), 3.10 (t, J=6.4 Hz, 2H), 2.24 (t, J=5.7 Hz, 1H), 2.18 (t, J=5.7 Hz, 1H), 2.11-2.03 (m, 2H), 2.02-1.95 (m, 2H), 1.94-1.87 (m, 1H), 0.94-0.86 (m, 2H), 0.85-0.79 (m, 2H).

Example 014: WX014

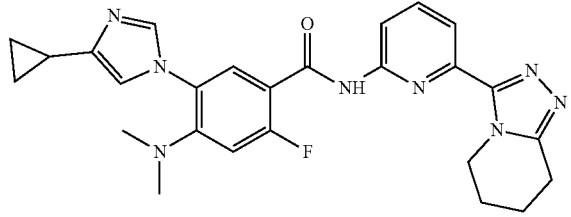 [SMILES: CN(C)c1cc(F)c(C(=O)Nc2cccc(-c3nnc4n3CCCC4)n2)cc1-n1cnc(C2CC2)c1]

Synthetic Route:

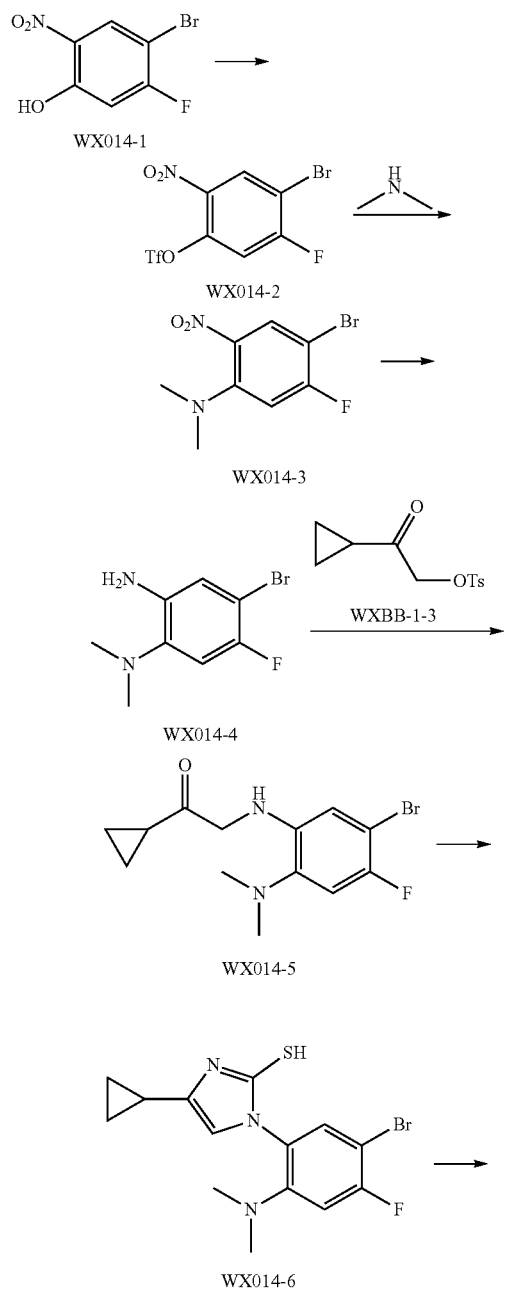

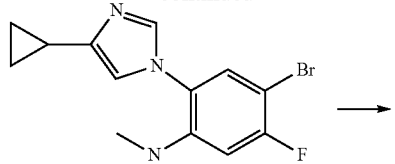

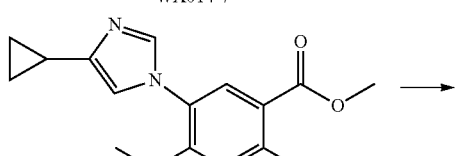

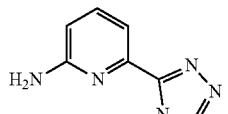

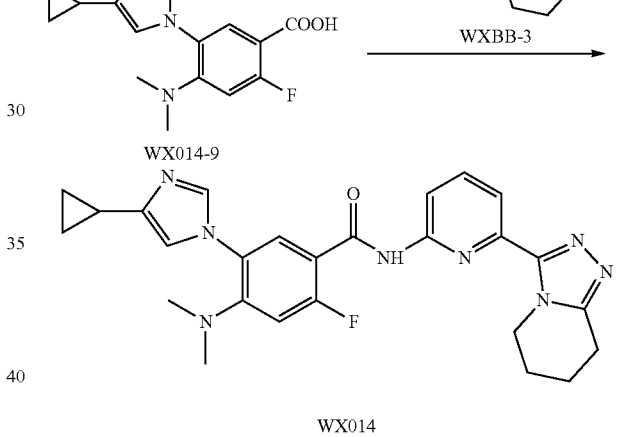

Step 1: Synthesis of Compound WX014-2

Compound WX014-1 (24 g, 101.70 mmol, 1 eq) was dissolved in anhydrous dichloromethane (200 mL), followed by addition of dimethylaminopyridine (0.65 g, 5.32 mmol, 0.05 eq) and diisopropylethylamine (26.29 g, 203.39 mmol, 35.43 mL, 2 eq). The system was cooled to 0° C., followed by slow addition of trifluoromethanesulfonic anhydride (43.04 g, 152.55 mmol, 25.17 mL, 1.5 eq) at 0° C. The system was then warmed to 20° C. and stirred for 2 hours. Water (200 mL) was added to the reaction solution while stirring. The organic phase was rotary evaporated to dry under reduced pressure to give a crude product. The crude product was purified by column chromatography (ethyl acetate/petroleum ether=0 to 5%) to give Compound WX014-2. $^1$H NMR (400 MHz, CHLOROFORM-d) δ ppm 7.29 (d, J=7.53 Hz, 1H) 8.51 (d, J=6.52 Hz, 1H).

Step 2: Synthesis of Compound WX014-3

Compound WX014-2 (24 g, 65.21 mmol, 1 eq) was dissolved in dry toluene (200 mL) and charged with nitrogen gas three times, followed by addition of dimethylamine (4.80 g, 58.86 mmol, 5.39 mL, 0.9 eq, HCl), sodium tert-butoxide (9.36 g, 97.39 mmol, 1.49 eq) and Pd$_2$(dba)$_3$ (4.80 g, 5.24 mmol, 0.08 eq). The mixture was stirred at 105° C. for 12 hours under nitrogen atmosphere. The reaction solution was cooled to room temperature, followed by addition of water (400 mL) and extraction with ethyl acetate (200 mL*3). The organic phases were combined, washed with saturated brine (300 mL), and dried over anhydrous sodium sulfate, followed by filtration. The filtrate was rotary evaporated to dry under reduced pressure to give a crude product. The crude product was purified by column chromatography (ethyl acetate/petroleum ether=0 to 5%) to give Compound WX014-3. $^1$H NMR (400 MHz, CHLOROFORM-d) δ ppm 2.91 (s, 6H) 6.75 (d, J=11.04 Hz, 1H) 8.02-8.07 (m, 1H).

Step 3: Synthesis of Compound WX014-4

Compound WX014-3 (9 g, 28.59 mmol, 1 eq) (purity: 83.568%) was dissolved in acetic acid (80 mL), followed by addition of Fe powder (6.39 g, 114.36 mmol, 4 eq) in portions. The mixture was stirred at 20° C. for 16 hours. The reaction solution was added dropwise to saturated NaOH (100 mL), and extracted with ethyl acetate (50 mL*3). The organic phases were combined, washed with saturated brine (300 mL), and dried over anhydrous sodium sulfate, followed by filtration. The filtrate was rotary evaporated to dry under reduced pressure. The crude product was purified by column (ethyl acetate/petroleum ether=0-25%) to give Compound WX014-4. $^1$H NMR (400 MHz, CHLOROFORM-d) δ ppm 2.65 (s, 6H) 6.80 (d, J=10.29 Hz, 1H) 6.86 (d, J=6.78 Hz, 1H).

Step 4: Synthesis of Compound WX014-5

Compound WX014-4 (1.1 g, 3.42 mmol, 1 eq) (purity 72.474%) was dissolved in anhydrous toluene (10 mL), followed by addition of Compound WXBB-1-3 (3 g, 11.80 mmol, 3.45 eq) and diisopropylethylamine (928.29 mg, 7.18 mmol, 1.25 mL, 2.1 eq). The mixture was reacted at 140° C. for 0.5 hour under microwave condition. The reaction solution was cooled to room temperature, followed by addition of water (50 mL) and extraction with ethyl acetate (50 mL*3). The organic phases were combined, washed with sodium chloride (50 mL), and dried over anhydrous sodium sulfate, followed by filtration. The filtrate was rotary evaporated to dry under reduced pressure. The crude product was purified by column chromatography (ethyl acetate/petroleum ether=0 to 10%) to give Compound WX014-5. $^1$H NMR (400 MHz, CHLOROFORM-d) δ ppm 0.93 (dq, J=7.47, 3.70 Hz, 2H) 1.09 (quin, J=3.83 Hz, 2H) 1.90-1.99 (m, 1H) 2.56 (s, 6H) 4.07 (d, J=3.51 Hz, 2H) 6.49 (d, J=6.53 Hz, 1H) 6.73 (d, J=10.04 Hz, 1H).

Step 5: Synthesis of Compound WX014-6

Compound WX014-5 (750 mg, 2.38 mmol, 1 eq) was dissolved in acetic acid (8 mL), and charged with nitrogen gas three times, followed by addition of potassium thiocyanate (463 mg, 4.76 mmol, 463.00 µL, 2 eq). The mixture was stirred at 110° C. for 4 hours under nitrogen atmosphere. The reaction solution was cooled to room temperature, concentrated under reduced pressure, adjusted to pH=8 with saturated sodium bicarbonate (20 mL), and extracted with dichloromethane (20 mL*3). The organic phase was washed with saturated sodium chloride (30 mL), and dried over anhydrous sodium sulfate, followed by filtration. The filtrate was rotary evaporated to dry under reduced pressure. Compound WX014-6 was given as the product, which was used directly in the next reaction without purification. $^1$H NMR (400 MHz, DMSO-d6) δ ppm 0.64-0.71 (m, 2H) 0.78-0.89 (m, 2H) 1.67-1.76 (m, 1H) 2.57 (s, 6H) 6.75 (d, J=1.51 Hz, 1H) 7.00 (d, J=11.80 Hz, 1H) 7.40 (d, J=7.53 Hz, 1H) 12.28 (br s, 1H).

Step 6: Synthesis of Compound WX014-7

Compound WX014-6 (500 mg, 1.40 mmol, 1 eq) was dissolved in acetic acid (5 mL), followed by addition of water (1 mL) and hydrogen peroxide (477 mg, 4.21 mmol, 404.24 µL, 30% purity, 3 eq). The mixture was stirred at 45° C. for 1 hour. The reaction solution was cooled to room temperature, and saturated sodium sulfite was added thereto until no blue color was detected by the potassium iodide starch paper. A part of the solvent was evaporated off, and no residual hydrogen peroxide was detected by the potassium iodide starch paper. The reaction solution was adjust to pH=8 with saturated sodium bicarbonate (20 mL), and extracted with dichloromethane (20 mL*3). The organic phase was washed with saturated sodium chloride (50 mL), and dried over anhydrous sodium sulfate, followed by filtration. The filtrate was rotary evaporated to dry under reduced pressure. Compound WX014-7 was given as the product, which was used directly in the next reaction without purification. $^1$H NMR (400 MHz, DMSO-d6) δ ppm 0.62-0.71 (m, 2H) 0.77-0.82 (m, 2H) 2.32-2.34 (m, 1H) 2.43 (s, 6H) 7.08 (d, J=11.29 Hz, 1H) 7.14 (s, 1H) 7.56 (d, J=7.53 Hz, 1H) 7.69 (s, 1H).

Step 7: Synthesis of Compound WX014-8

Compound WX014-7 (400 mg, 1.09 mmol, 1 eq) (purity 88.522%) was dissolved in methanol (4 mL), followed by addition of Pd(dppf)Cl$_2$ (120 mg, 164.00 µmol, 0.15 eq) and triethylamine (221 mg, 2.18 mmol, 303.99 µL, 2 eq), and introduction of carbon monoxide (50 Psi). The mixture was stirred at 70° C. for 16 hours. The reaction solution was concentrated. The crude product was purified by column chromatograph (ethyl acetate/petroleum ether=0 to 30%). The product was further purified by prep-TLC (ethyl acetate) to give Compound WX014-8. $^1$H NMR (400 MHz, CHLOROFORM-d) δ ppm 0.77-0.83 (m, 2H) 0.85-0.92 (m, 2H) 1.86-1.95 (m, 1H) 2.61 (s, 6H) 3.89 (s, 3H) 6.63 (d, J=13.30 Hz, 1H) 6.86 (d, J=1.00 Hz, 1H) 7.54 (d, J=1.00 Hz, 1H) 7.73 (d, J=7.78 Hz, 1H).

Step 8: Synthesis of Compound WX014-9

Compound WX014-8 (200 mg, 566.13 µmol, 1 eq) (purity 85.863%) was dissolved in a mixture of tetrahydrofuran (1 mL) and water (1 mL) (volume ratio: 1:1), followed by addition of lithium hydroxide (41 mg, 1.71 mmol, 3.02 eq). The mixture was stirred at 20° C. for 1 hour. The reaction solution was concentrated to give Compound WX014-9. $^1$H NMR (400 MHz, DMSO-d6) δ ppm 0.65-0.71 (m, 2H) 0.75-0.81 (m, 2H) 1.79-1.88 (m, 1H) 2.41 (s, 6H) 6.67 (d, J=12.30 Hz, 1H) 7.06 (s, 1H) 7.44 (d, J=8.03 Hz, 1H) 7.61 (s, 1H).

Step 9: Synthesis of Compound WX014

Compound WX014-9 (160 mg, 553.05 µmol, 1 eq) was dissolved in dichloromethane (2 mL), followed by addition of N,N-dimethylformamide (4 mg, 54.72 µmol, 4.21 µL, 0.1 eq) and oxalyl chloride (120 mg, 945.43 µmol, 82.76 µL, 1.71 eq). The mixture was stirred at 20° C. for 2 hours. The solvent was evaporated off under reduced pressure until the mixture was viscous, followed by addition of 5 mL of anhydrous dichloromethane. Such procedures were repeated three times, followed by addition of Compound WXBB-3 (119 mg, 552.84 µmol, 1 eq) and diisopropylethylamine (72 mg, 557.09 µmol, 97.04 µL, 1.01 eq). The mixture was stirred at 20° C. for 1 hour, followed by addition of water (50 mL) and extraction with dichloromethane (20 mL*3). The organic phase was washed with saturated sodium chloride (50 mL), and dried over anhydrous sodium sulfate, followed by filtration. The filtrate was rotary evaporated to dry under reduced pressure. The dried crude product was purified by prep-TLC (dichloromethane/methanol=10/1), and isolated by rapid preparation to give WX014. $^1$H NMR (400 MHz, DMSO-d6) δ ppm 0.69 (br s, 2H) 0.79 (br d, J=8.03 Hz, 2H) 1.24 (br s, 1H) 1.80-2.00 (m, 6H) 2.53 (br s, 6H) 4.43-4.51 (m, 2H) 6.97 (br d, J=13.05 Hz, 1H) 7.15 (s, 1H) 7.55 (br d, J=7.28 Hz, 1H) 7.71 (s, 1H) 7.85 (d, J=7.53 Hz, 1H) 7.98 (t, J=7.91 Hz, 1H) 8.15 (d, J=8.03 Hz, 1H) 10.61 (s, 1H).

Example 015: WX015

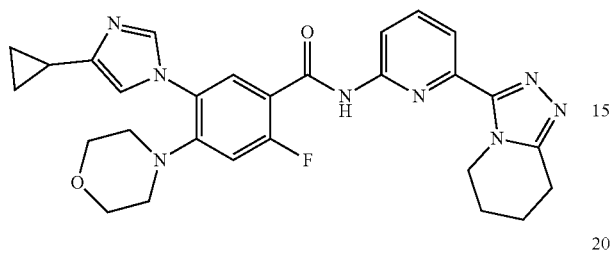

Synthetic Route:

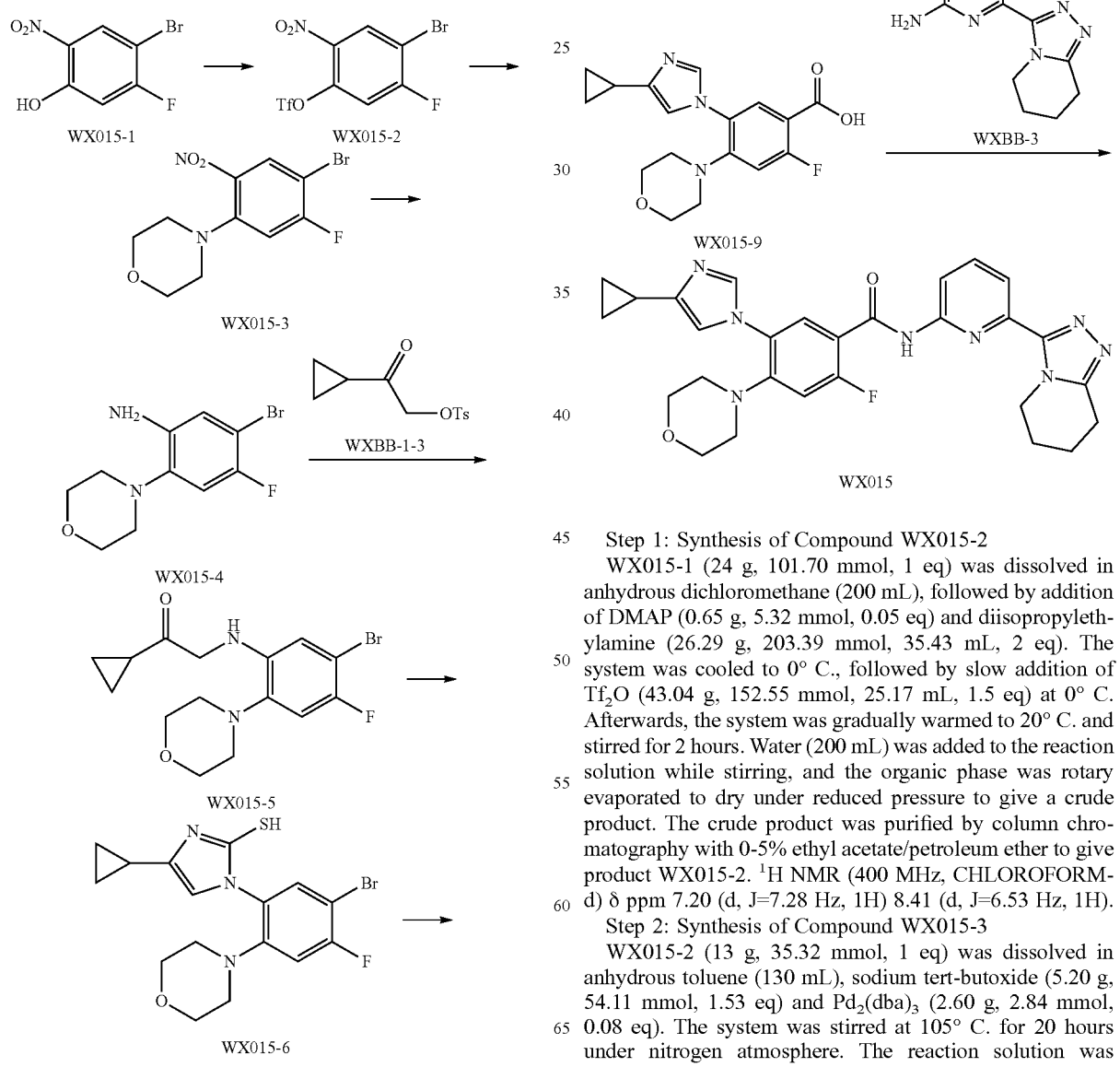

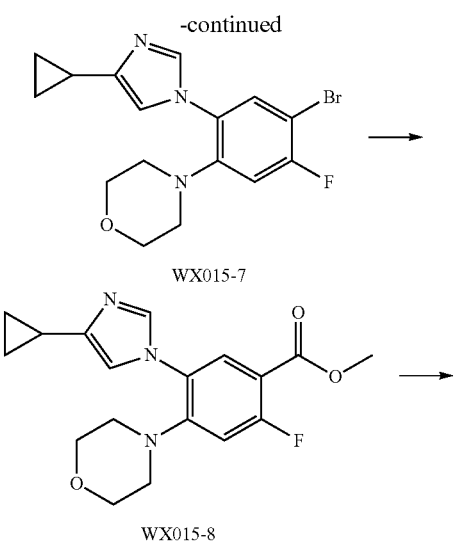

Step 1: Synthesis of Compound WX015-2

WX015-1 (24 g, 101.70 mmol, 1 eq) was dissolved in anhydrous dichloromethane (200 mL), followed by addition of DMAP (0.65 g, 5.32 mmol, 0.05 eq) and diisopropylethylamine (26.29 g, 203.39 mmol, 35.43 mL, 2 eq). The system was cooled to 0° C., followed by slow addition of Tf$_2$O (43.04 g, 152.55 mmol, 25.17 mL, 1.5 eq) at 0° C. Afterwards, the system was gradually warmed to 20° C. and stirred for 2 hours. Water (200 mL) was added to the reaction solution while stirring, and the organic phase was rotary evaporated to dry under reduced pressure to give a crude product. The crude product was purified by column chromatography with 0-5% ethyl acetate/petroleum ether to give product WX015-2. $^1$H NMR (400 MHz, CHLOROFORM-d) δ ppm 7.20 (d, J=7.28 Hz, 1H) 8.41 (d, J=6.53 Hz, 1H).

Step 2: Synthesis of Compound WX015-3

WX015-2 (13 g, 35.32 mmol, 1 eq) was dissolved in anhydrous toluene (130 mL), sodium tert-butoxide (5.20 g, 54.11 mmol, 1.53 eq) and Pd$_2$(dba)$_3$ (2.60 g, 2.84 mmol, 0.08 eq). The system was stirred at 105° C. for 20 hours under nitrogen atmosphere. The reaction solution was cooled to room temperature, added into water (200 mL), and extracted with ethyl acetate (200 mL*2). The organic phase was sequentially washed with water (300 mL), saturated brine (300 mL), and dried over anhydrous sodium sulfate, followed by filtration. The filtrate was rotary evaporated to dry under reduced pressure to give a crude product. The crude product was purified by column chromatography with 0-20% ethyl acetate/petroleum ether to give product WX015-3. $^1$H NMR (400 MHz, CHLOROFORM-d) δ ppm 3.04-3.09 (m, 4H) 3.84-3.87 (m, 4H) 6.86 (d, J=10.04 Hz, 1H) 8.12 (d, J=7.03 Hz, 1H).

Step 3: Synthesis of Compound WX015-4

WX015-3 (8 g, 26.22 mmol, 1 eq) was dissolved in glacial acetic acid (80 mL), followed by slow addition of Fe powder (5.86 g, 104.88 mmol, 4 eq) in portions while stirring. The system was stirred at 20° C. for 1 hour. The reaction solution was rotary evaporated to dry under reduced pressure to give a crude material, and diluted with water (200 mL). The solution was adjusted to pH 8-9 with saturated sodium bicarbonate solution (200 mL), and extracted with dichloromethane (100 mL*2). The organic phase was washed with water (200 mL), and dried over anhydrous sodium sulfate, followed by filtration. The filtrate was rotary evaporated to dry to give product WX015-4.

Step 4: Synthesis of Compound WX015-5

WXBB-1-3 (6.98 g, 27.47 mmol, 3 eq) was dissolved in anhydrous toluene (30 mL), followed by addition of WX015-4 (3 g, 9.16 mmol, 1 eq) (purity: 83.959%) and diisopropylethylamine (2.49 g, 19.27 mmol, 3.36 mL, 2.1 eq). The system was heated to 140° C. under microwave condition and stirred for 1 hour. The reaction solution was cooled to room temperature, followed by addition of water (50 mL) and extraction with ethyl acetate (50 mL*2). The organic phase was dried over anhydrous sodium sulfate, followed by filtration. The filtrate was rotary evaporated to dry under reduced pressure to give a crude product. The crude product was purified by column chromatography (0-12% ethyl acetate/petroleum ether) to give product WX015-5.

Step 5: Synthesis of Compound WX015-6

WX015-5 (1.2 g, 2.71 mmol, 1 eq) (purity 80.641%) was dissolved in glacial acetic acid (20 mL), followed by addition of potassium thiocyanate (0.36 g, 3.70 mmol, 360.00 μL, 1.37 eq). The system was stirred at 110° C. for 3 hours. The reaction solution was cooled to room temperature, diluted with water (100 mL), and extracted with dichloromethane (50 mL*3). The organic phases were combined, followed by addition of saturated sodium bicarbonate solution (200 mL), and stirred for 5 minutes. The pH of the organic phase was 7-8 measured by pH test paper. The organic phase was isolated, washed with water (200 mL), and dried over anhydrous magnesium sulfate, followed by filtration. The filtrate was rotary evaporated to dry under reduced pressure to give product WX015-6.

Step 6: Synthesis of Compound WX015-7

WX015-6 (1.2 g, 2.62 mmol, 1 eq) (purity 87.114) was dissolved in a mixture of glacial acetic acid (12 mL) and water (2.5 mL), followed by addition of hydrogen peroxide (0.9 g, 7.94 mmol, 762.71 μL, 30% purity, 3.02 eq) while stirring. The system was stirred at 45° C. for 0.5 hour. The reaction solution was cooled to room temperature, diluted with water (100 mL), and extracted with dichloromethane (50 mL*3). The organic phases were combined, followed by addition of saturated sodium sulfite solution (50 mL), and stirred for 5 minutes. No blue color was detected by the potassium iodide starch paper. Afterwards, saturated Na$_2$CO$_3$ solution (200 mL) was added thereto, and stirred for 5 minutes. The pH of the organic phase was 7-8 measured by pH test paper. The organic phase was isolated, washed with water (200 mL), and dried over anhydrous magnesium sulfate, followed by filtration. The filtrate was rotary evaporated to dry under reduced pressure to give product WX015-7.

Step 7: Synthesis of Compound WX015-8

WX015-7 (1 g, 1.78 mmol, 1 eq) (purity 65.303%) was dissolved in methanol (10 mL), followed by addition of Pd(dppf)Cl$_2$ (0.04 g, 54.67 μmol, 0.15 eq) and triethylamine (400.00 mg, 3.95 mmol, 550.21 μL, 2.22 eq). The system was stirred at 70° C. for 16 hours under CO atmosphere (50 psi). The reaction solution was rotary evaporated to dry under reduced pressure to give a crude material, which is purified by column chromatography with 0-40% ethyl acetate/petroleum ether to give product WX015-8.

Step 8: Synthesis of Compound WX015-9

WX015-8 (0.6 g, 1.55 mmol, 1 eq) (purity: 89.457%) was dissolved in anhydrous tetrahydrofuran (5 mL), followed by addition of a solution of lithium hydroxide (0.112 g, 4.68 mmol, 3.01 eq) in water (5 mL). The system was stirred at 20° C. for 1 hour. The reaction solution was rotary evaporated to dry under reduced pressure to give a crude material. A mixed solution of dichloromethane/methanol=10/1 (15 mL) was added to the crude product, and stirred for 15 min, followed by filtration. The filtrate was rotary evaporated to dry under reduced pressure to give product WX015-9. $^1$H NMR (400 MHz, DMSO-d$_6$) δ ppm 0.66 (br d, J=3.01 Hz, 2H) 0.72-0.84 (m, 2H) 1.77-1.91 (m, 1H) 2.58 (br s, 4H) 3.55 (br s, 4H) 6.74 (d, J=11.80 Hz, 1H) 7.16 (s, 1H) 7.50 (d, J=7.78 Hz, 1H) 7.72 (s, 1H).

Step 9: Synthesis of Compound WX015

WX015-9 (0.1 g, 301.80 μmol, 1 eq) was dissolved in anhydrous dichloromethane (2 mL), followed by addition of N,N-dimethylformamide (5 mg, 68.41 μmol, 5.26 μL, 2.27e-1 eq), and addition of oxalyl chloride (0.08 g, 630.29 μmol, 55.17 μL, 2.09 eq) under nitrogen atmosphere. The system was stirred at 20° C. for 0.5 hours. The reaction solution was rotary evaporated to dry under reduced pressure until viscous, followed by addition of anhydrous dichloromethane (2 mL). Such procedures were repeated three times, followed by sequential addition of anhydrous dichloromethane (2 mL), WXBB-3 (0.065 g, 301.97 μmol, 1.00 eq) and diisopropylethylamine (0.08 g, 618.99 μmol, 107.82 μL, 2.05 eq). The system was stirred at 20° C. for 1 hour. The reaction solution was diluted with water (20 mL), and extracted with dichloromethane (20 mL*2). The organic phase was washed with water (30 mL), and dried over anhydrous sodium sulfate, followed by filtration. The filtrate was rotary evaporated to dry under reduced pressure to give a crude product. The crude product was isolated and purified by rapid preparation to give WX015. $^1$H NMR (400 MHz, CHLOROFORM-d) δ ppm 0.80 (br d, J=3.26 Hz, 2H) 0.91 (br d, J=8.03 Hz, 2H) 1.87-1.94 (m, 1H) 1.96-2.09 (m, 4H) 2.79 (br d, J=4.02 Hz, 4H) 3.10 (br t, J=6.27 Hz, 2H) 3.73 (br s, 4H) 4.50 (br t, J=6.02 Hz, 2H) 6.81 (d, J=13.80 Hz, 1H) 6.99 (s, 1H) 7.71 (s, 1H) 7.84-7.96 (m, 1H) 8.05 (dd, J=15.69, 7.91 Hz, 2H) 8.36 (d, J=8.28 Hz, 1H) 9.00 (br d, J=15.56 Hz, 1H)

Example 016: WX016

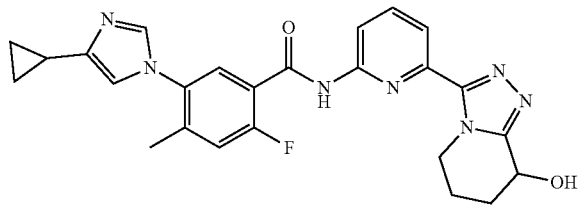 [SMILES: Cc1cc(F)c(C(=O)Nc2cccc(-c3nnc4n3CCCC4O)n2)cc1-n1cnc(C2CC2)c1]

Synthetic Route:

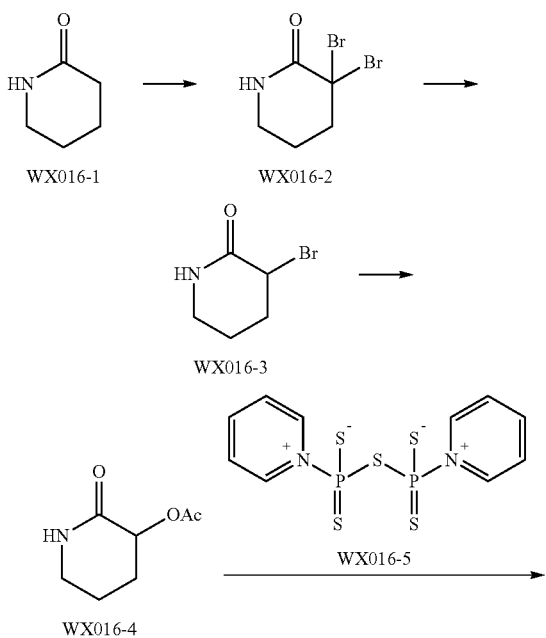

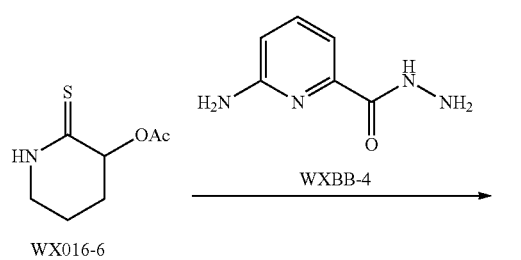

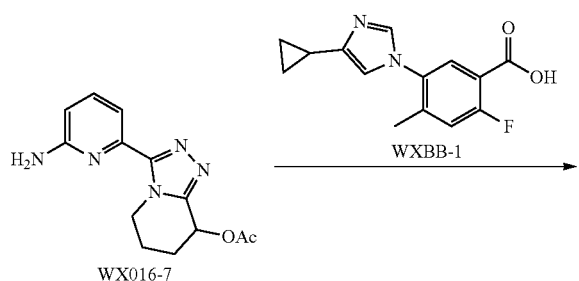

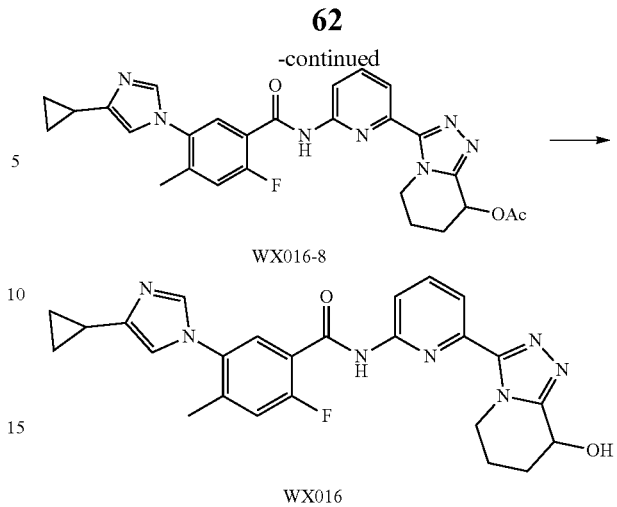

WX016

Step 1: Synthesis of Compound WX016-2

WX016-1 (20 g, 201.75 mmol, 1 eq) was dissolved in CHCl$_3$ (200 mL) in a pre-dried 100 mL round bottom flask. After the reaction system was cooled to 0° C., PCl$_5$ (84.03 g, 403.51 mmol, 2 eq) was added thereto in portions. The system was reacted at 0° C. for 30 minutes. Afterwards, ZnCl$_2$ (1.37 g, 10.09 mmol, 472.48 μL, 0.05 eq) and Br$_2$ (64.48 g, 403.51 mmol, 20.80 mL, 2 eq) were added to the system. The temperature of the reaction was then raised to 0-25° C. and the reaction was carried out for 5 hours. Saturated sodium sulfite solution was slowly added to the reaction solution while stirring until pH=8-9. The organic phase was collected after separation, and the aqueous phase was extracted with dichloromethane (3*100 mL). The organic phases were combined, washed with saturated brine (1*200 mL) and dried over anhydrous sodium sulfate, followed by filtration. The filtrate was concentrated under reduced pressure to give WX016-2.

Step 2: Synthesis of Compound WX016-3

Raw material WX016-2 (10 g, 38.92 mmol, 1 eq) was added into a pre-dried 250 mL round bottom flask, followed by addition of a mixture of H$_2$O (5 mL) and MeOH (45 mL). PPh$_3$ (10.21 g, 38.92 mmol, 1 eq) was slowly added to the system at 40° C. and stirred for 3 hours. The solvent of the reaction system was concentrated to about half of its original volume in vacuum, and water was added slowly until no solids were precipitated. The solids were filtered off, and the filtrate was extracted with dichloromethane (3*30 mL). The organic phase was washed with saturated brine (2*40 mL), dried over anhydrous sodium sulfate, filtered and concentrated under reduced pressure to give WX016-3. $^1$H NMR (400 MHz, CHLOROFORM-d) δ ppm 1.73-1.87 (m, 2H) 2.13-2.23 (m, 2H) 2.23-2.31 (m, 3H) 3.37-3.49 (m, 2H) 4.51 (t, J=4.39 Hz, 1H), m/z=178.09 [M+1].

Step 3: Synthesis of Compound WX016-4

WX016-3 (7.2 g, 28.31 mmol, 1 eq) was added into a dry round bottom flask, followed by addition of ACN (20 mL), KOAc (11.11 g, 113.24 mmol, 4 eq) and 18-crown-6 (2.24 g, 8.49 mmol, 0.3 eq) while stirring, and heated to reflux at 85° C. for 1 hour. The reaction system was cooled to room temperature, adjusted to pH=3-4 with 1M hydrochloric acid and extracted with dichloromethane (3×20 mL). The organic phases were combined, adjusted with saturated sodium bicarbonate to pH=8-9, and extracted with dichloromethane (3×30 mL). The organic phases were washed with saturated brine (2×40 mL), dried over anhydrous sodium sulfate, and concentrated under reduced pressure. The residue was purified by column chromatography (DCM:MeOH=100:0 to 40:1 to 20:1) to give WX016. ¹H NMR (400 MHz, CHLOROFORM-d) δ ppm 1.79-1.96 (m, 4H) 2.01-2.08 (m, 1H) 2.22-2.32 (m, 2H) 3.25-3.37 (m, 3H) 5.17-5.25 (m, 1H), m/z=158.1 [M+1].

Step 4: Synthesis of Compound WX016-6

Compound WX016-4 (20.00 g, 127.25 mmol, 1 eq) and Compound WX016-5 (14.52 g, 38.18 mmol, 0.3 eq) were added into a dry round bottom flask, followed by addition of acetonitrile (250 mL). The reaction system was warmed to 60° C. and stirred for 4 hours. The reaction solution was cooled to room temperature, followed by rotary evaporation to dry. Water (250 mL) and dichloromethane (250 mL) were added into the reaction flask. After the organic phase and the aqueous phase were separated, the aqueous phase was extracted with dichloromethane (200 mL*2). The organic phases were combined, washed with saturated brine (200 mL), dried over anhydrous sodium sulfate, filtered and rotary evaporated to dry under reduced pressure to give WX016-6. ¹H NMR (1H NMR (400 MHz, CHLOROFORM-d) δ ppm 1.86-1.93 (m, 2H) 1.96-2.07 (m, 2H) 2.11 (s, 3H) 3.28-3.35 (m, 2H) 5.41-5.47 (m, 1H)

Step 5: Synthesis of Compound WX016-7

Compound WX016-6 (12.00 g, 67.29 mmol, 1 eq) was added into a dry round bottom flask, followed by sequential addition of Compound WXBB-4 (10.54 g, 69.27 mmol, 1 eq) and cyclohexanol (200 mL). The air in the system was charged with a nitrogen balloon, and the procedures were repeated twice. The reaction system was heated to 135° C. and stirred for 12 hours. The reaction solution was cooled to room temperature, followed by addition of water (250 mL), and adjusted to pH=4-5 with 1M hydrochloric acid. The aqueous phase was washed with ethyl acetate (200 mL*3), and the obtained aqueous phase was adjusted to pH=9 with 1 M sodium hydroxide, followed by extraction with dichloromethane (250 mL*3). The organic phases were combined, wash with saturated brine (250 mL), and dried over anhydrous sodium sulfate, followed by filtration. The filtrate was rotary evaporated to dry under reduced pressure (water pump, 50° C.) to give a crude product. The crude product was isolated and purified by prep-HPLC (water (0.04% NH₃.H₂O+10 mM NH₄HCO₃)—CAN) to give Compound WX016-7. ¹H NMR (400 MHz, CHLOROFORM-d) δ ppm 1.99-2.09 (m, 2H) 2.11 (s, 3H) 2.14-2.26 (m, 2H) 4.21-4.37 (m, 1H) 4.56 (br s, 2H) 4.75 (dt, J=13.93, 4.83 Hz, 1H) 6.24 (t, J=4.02 Hz, 1H) 6.51-6.58 (m, 1H) 7.51-7.57 (m, 1H) 7.60-7.65 (m, 1H). MS m/z: 274 [M+H]+.

Step 6: Synthesis of Compound WX016-8

Compound WXBB-1 (3.50 g, 13.39 mmol, 1 eq) was added into a dry round bottom flask, followed by addition of dichloromethane (35 mL). The air in the system was charged with a nitrogen balloon twice. N,N-dimethylformamide (0.1 mL, 1.3 mmol, 0.1 eq) and oxalyl chloride (2 mL, 22.85 mmol, 1.7 eq) were added thereto under nitrogen atmosphere. The reaction system was stirred at room temperature (20° C.) for 3 hours until the reaction solution was clear. The reaction solution was concentrated to 15 mL, followed by addition of anhydrous dichloromethane (20 mL), and then concentrated to 15 mL. Such procedures were repeated three times. Afterwards, anhydrous dichloromethane (20 mL) was added, and the air in the system was charged with a nitrogen balloon twice. Compound WX016-7 (3.50 g, 12.03 mmol, 0.9 eq) and N,N-dimethylformamide (2.4 mL, 13.78 mmol, 1 eq) were added thereto under nitrogen atmosphere. The reaction system was stirred at room temperature (20° C.) for 1 hour, followed by addition of water (50 mL), and then adjusted to pH=9 with potassium carbonate solid, and extracted with dichloromethane (50 mL*3). The organic phases were combined, washed with saturated brine (50 mL), and dried over anhydrous sodium sulfate, followed by filtration. The filtrate was rotary evaporated to dry under reduced pressure to give WX016-8. ¹H NMR (400 MHz, DMSO-d6) δ ppm 0.68-0.73 (m, 2H) 0.78-0.83 (m, 2H) 1.81-1.89 (m, 1H) 1.99-2.08 (m, 4H) 2.09 (s, 3H) 2.25 (s, 3H) 4.28-4.36 (m, 1H) 4.71-4.81 (m, 1H) 6.19 (s, 1H) 7.19 (d, J=1.25 Hz, 1H) 7.49 (d, J=11.04 Hz, 1H) 7.64 (d, J=6.53 Hz, 1H) 7.70 (d, J=1.25 Hz, 1H) 7.93 (d, J=7.03 Hz, 1H) 8.04 (t, J=7.91 Hz, 1H) 8.22 (d, J=8.03 Hz, 1H) 11.03 (s, 1H). MS m/z: 516.4 [M+H]+.

Step 7: Synthesis of Compound WX016

Compound WX016-8 (3.00 g, 4.23 mmol, 1 eq) (purity 72.65%) was added into a dry round bottom flask, and a mixture of tetrahydrofuran (15 mL) and water (5 mL) was added to the reaction flask, followed by addition of lithium hydroxide monohydrate (532 mg, 12.68 mmol, 3 eq). The reaction system was stirred at room temperature (24° C.) for 2 hours. Water (50 mL) was added to the reaction solution, followed by extraction with dichloromethane (50 mL*3). The organic phases were combined, washed with saturated brine (50 mL), and dried over anhydrous sodium sulfate, followed by filtration. The filtrate was rotary evaporated to dry under reduced pressure to give WX016. ¹HNMR (400 MHz, DMSO-d6) δ ppm 0.68-0.73 (m, 2H) 0.78-0.83 (m, 2H) 1.81-1.89 (m, 1H) 1.99-2.08 (m, 4H) 2.09 (s, 3H) 2.25 (s, 3H) 4.28-4.36 (m, 1H) 4.71-4.81 (m, 1H) 6.19 (s, 1H) 7.19 (d, J=1.25 Hz, 1H) 7.49 (d, J=11.04 Hz, 1H) 7.64 (d, J=6.53 Hz, 1H) 7.70 (d, J=1.25 Hz, 1H) 7.93 (d, J=7.03 Hz, 1H) 8.04 (t, J=7.91 Hz, 1H) 8.22 (d, J=8.03 Hz, 1H) 11.03 (s, 1H). MS m/z: 474.2 [M+H]+.

Example 017: WX017-WX018

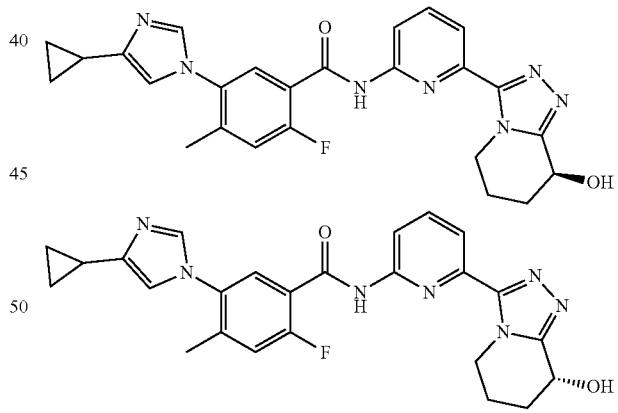

Step 1: Synthesis of Compound WX017, WX018

Compound WX016 was separated by SFC (column: YMC CHIRAL Amylose-C (250 mm*30 mm, 10 μm): mobile phase: [0.1% NH₃.H₂O EtOH]: B: 55%-55%, min) to give WX017 and WX018 with a retention time at 0.921 min and 1.459 min, respectively.

The retention time of WX017 is 0.921 min. ¹H NMR (400 MHz, DMSO-d6) δ ppm 0.67-0.73 (m, 2H) 0.77-0.84 (m, 2H) 1.82-1.97 (m, 4H) 2.14 (br dd, J=9.16, 5.65 Hz, 1H) 2.25 (s, 3H) 4.20-4.30 (m, 1H) 4.68 (br d, J=13.80 Hz, 1H) 4.90 (br d, J=4.77 Hz, 1H) 5.81 (d, J=5.27 Hz, 1H) 7.19 (d, J=1.25 Hz, 1H) 7.49 (d, J=10.79 Hz, 1H) 7.63 (d, J=6.53 Hz, 1H) 7.70 (d, J=1.25 Hz, 1H) 7.91 (d, J=7.53 Hz, 1H) 8.02 (t, J=7.91 Hz, 1H) 8.20 (d, J=8.28 Hz, 1H) 10.99 (s, 1H). MS m/z: 474.5 [M+H]+.

The retention time of WX018 is 1.459 min. $^1$H NMR (400 MHz, DMSO-d6) δ ppm 0.68-0.73 (m, 2H) 0.77-0.84 (m, 2H) 1.81-1.98 (m, 4H) 2.14 (br dd, J=8.91, 5.40 Hz, 1H) 2.25 (s, 3H) 4.21-4.29 (m, 1H) 4.68 (br d, J=14.31 Hz, 1H) 4.87-4.93 (m, 1H) 5.82 (d, J=5.02 Hz, 1H) 7.19 (d, J=1.00 Hz, 1H) 7.49 (d, J=10.79 Hz, 1H) 7.63 (d, J=6.53 Hz, 1H) 7.70 (d, J=1.00 Hz, 1H) 7.91 (d, J=7.28 Hz, 1H) 8.02 (t, J=7.91 Hz, 1H) 8.20 (d, J=8.03 Hz, 1H) 11.00 (s, 1H). MS m/z: 474.2 [M+H]+.

Biological Activity Test:

Experimental Example 1: Enzyme Activity

Reagents:

Primary reaction buffer solution: 20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT, 1% DMSO Treatment of the Compound:

The tested compounds were formulated into a 10 mM stock solution in DMSO, diluted in 3-fold gradient for a total of 10 concentrations, and placed in a 384-well plate (Cyclic Olefin Copolymer LDV Echo®).

Kinase Name: ASK1/MAP3K5 (Invitrogen, Carlsbad, Calif.)

Type: Recombinant Human Full Length Protein, GST-tagged

Final reaction concentration of the enzyme: 20 nM

Substrate: Myelin basic protein, MBP (Active Motif, Carlsbad, Calif.)

Final reaction concentration of the substrate: 20 μM

Experimental Procedures:

1. The substrate was dissolved in a freshly prepared primary reaction buffer solution, 2. The desired coenzyme factor was added to the above substrate solution, 3. The kinase was added to the substrate solution and mix gently, 4. The solution tested compound in DMSO was added to the kinase reaction solution and incubated at room temperature for 20 minutes.

5. The reaction was initiated by adding $^{33}$P-ATP (specific activity 10 μCi/μL) to the reaction solution.

6. Incubated at room temperature for 2 hours.

7. A small portion of the reactants were placed onto the P-81 ion exchange filter paper.

8. The filter paper was washed three times with 0.75% phosphate buffer to wash away unbound phosphate, and then dried.

9. The radioactivity remaining on the filter paper was determined,

10. The data for the kinase activity was expressed as the ratio of the kinase activity remaining in the test sample to the kinase activity in the vehicle (DMSO).

11. $IC_{50}$ values and curve fitting were collected by Prism (GraphPad software). The experimental results were shown in Table 1 and Table 2:

TABLE 1

In vitro screening test results of the compounds of the invention

| No. | Compound | $IC_{50}$ (nM) |
|---|---|---|
| 1 | Example 001: WX001 | 1.82 |
| 2 | Example 002: WX002 | 5.6 |
| 3 | Example 003: WX003 | 943 |
| 4 | Example 004: WX004 | >1000 |
| 5 | Example 005: WX005 | 35.3 |
| 6 | Example 006: WX006 | 19.20 |
| 7 | Example 007: WX007 | 16.60 |
| 8 | Example 008: WX008 | 5.44 |
| 9 | Example 010: WX010 | 7.20 |
| 10 | Example 011: WX011 | 7.61 |
| 11 | Example 012: WX012 | 7.04 |
| 12 | Example 013: WX013 | 7.93 |
| 13 | Example 014: WX014 | 10.70 |
| 14 | Example 015: WX015 | 10.10 |
| 15 | Example 016: WX016 | 4.12 |
| 16 | Example 017: WX017 | 12.50 |
| 17 | Example 017: WX018 | 6.57 |

TABLE 2

In vitro screening test results of the compounds of the invention

| No. | Compound | $IC_{50}$ value |
|---|---|---|
| 1 | Example 001 | A |
| 2 | Example 002 | A |
| 3 | Example 003 | B |
| 4 | Example 004 | B |
| 5 | Example 005 | A |

Note:
A ≤ 100 nM;
B > 100 nM.

Conclusion: The compounds of the present invention have a significant inhibitory effect against ASK1.

Experimental Example 2: Pharmacokinetic Characteristics Study

Experimental Methods:

C57BL/6 male mice were used in this study. The drug concentration in the plasma of mice subjected to intravenous or oral administration of the test compound at different time points were quantitatively determine by LC/MS/MS method, respectively, in order to evaluate the pharmacokinetic characteristics of the tested drugs in mice.

A clear solution of the test compound was injected into C57BL/6 mice via the tail vein (overnight fasting, 7-10 weeks old), and the test compound was intragastrically administered to C57BL/6 mice (overnight fasting, 7-10 weeks old). 30 μL of the blood was collected from the jugular vein or the tail vein of the animals 0.0833, 0.25, 0.5, 1, 2, 4, 6, 8 and 24 hours after administration, and placed in the anticoagulant tube containing EDTA-$K_2$, followed by centrifugation at 4° C. for 15 minutes to collect the plasma. The plasma concentration was determined by LC-MS/MS. The pharmacokinetic parameters were calculated by the non-compartment model linear logarithmic trapezoidal method using WinNonlin™ Version 6.3 (Pharsight, Mountain View, Calif.) pharmacokinetic software. The experimental results were shown in Table 3:

TABLE 3

| Pharmacokinetic test results | | |
|---|---|---|
| Compound | Exposure (nM · h) | Bioavailability |
| WX002 | 408566 | 156% |
| WX017 | 59396 | 165% |
| WX018 | 53367 | 102% |

Experimental Conclusion: The compounds of the invention have high exposure and bioavailability in mice.

What is claimed is:

1. A compound as shown in formula (II), a pharmaceutically acceptable salt thereof or a tautomer thereof, (II)

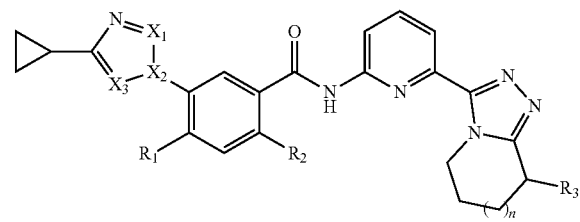

at least one of $X_1$, $X_2$ and $X_3$ is N, the rest of which is CH;
n is selected from 0 or 1;
$R_1$ is selected from H, F, Cl, Br, I, OH, $NH_2$, or selected from the group consisting of $C_{1-4}$ alkyl, $C_{1-4}$ heteroalkyl, 3-6 membered heterocycloalkyl and 5-6 membered heteroaryl, each of which is optionally substituted by 1, 2 or 3 R;
$R_2$ selected from H, F, Cl, Br, I;
$R_3$ is selected from H, F, Cl, Br, I, OH, $NH_2$;
R is selected from F, Cl, Br, I, OH, $NH_2$, or selected from the group consisting of $C_{1-3}$ alkyl, $C_{1-3}$ alkoxy and 3-6 membered heterocycloalkyl, each of which is optionally substituted by 1, 2 or 3 R';
R' is selected from the group consisting of F, Cl, Br, I, OH, $NH_2$ and $C_{1-3}$ alkyl;
each of the "hetero" in the $C_{1-4}$ heteroalkyl, 5-6 membered heteroaryl and 3-6 membered heterocycloalkyl is independently selected from the group consisting of -NH-, N, -O-, and -S-;
in any of the above cases, the number of the heteroatom or the heteroatomic group is independently selected from 1, 2 or 3.

2. The compound, the pharmaceutically acceptable salt thereof or the tautomer thereof according to claim 1, wherein, R is selected from F, Cl, Br, I, OH, $NH_2$, or selected from the group consisting of Me,

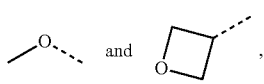

each of which is optionally substituted by 1, 2 or 3 R'.

3. The compound, the pharmaceutically acceptable salt thereof or the tautomer thereof according to claim 2, wherein, R is selected from F, Cl, Br, I, OH, $NH_2$, Me,

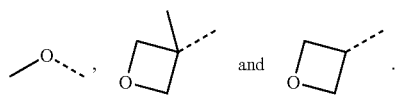

4. The compound, the pharmaceutically acceptable salt thereof or the tautomer thereof according to claim 1, wherein, $R_1$ is selected from H, F, Cl, Br, I, OH, $NH_2$, or selected from the group consisting of $C_{1-3}$ alkyl, $C_{1-3}$ alkoxy, $C_{1-3}$ alkylamino, morpholinyl and pyridyl, each of which is optionally substituted by 1, 2 or 3 R.

5. The compound, the pharmaceutically acceptable salt thereof or the tautomer thereof according to claim 4, wherein, $R_1$ is selected from H, F, Cl, Br, I, OH, $NH_2$, or selected from the group consisting of Me,

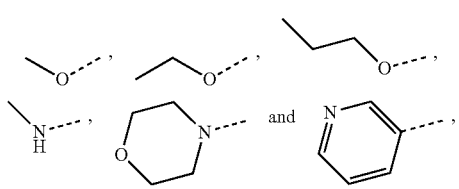

each of which is optionally substituted by 1, 2 or 3 R.

6. The compound, the pharmaceutically acceptable salt thereof or the tautomer thereof according to claim 5, wherein, $R_1$ is selected from H, F, Cl, Br, I, OH, $NH_2$, Me,

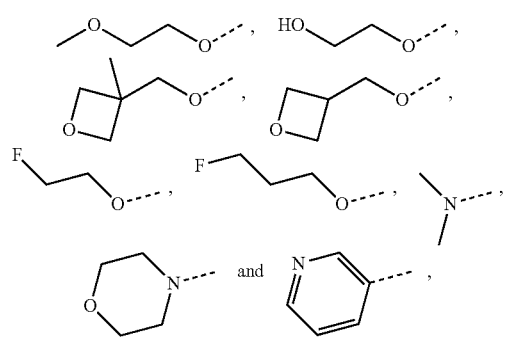

7. The compound, the pharmaceutically acceptable salt thereof or the tautomer thereof according to claim 1, wherein, the moiety

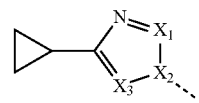

is selected from the group consisting of

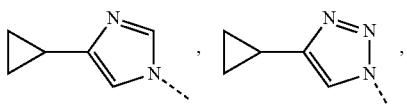

-continued

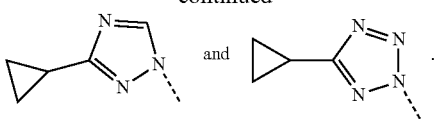

8. The compound, the pharmaceutically acceptable salt thereof or the tautomer thereof according to claim 1, wherein, the moiety

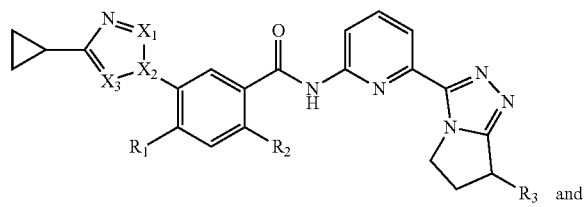

is selected from the group consisting of

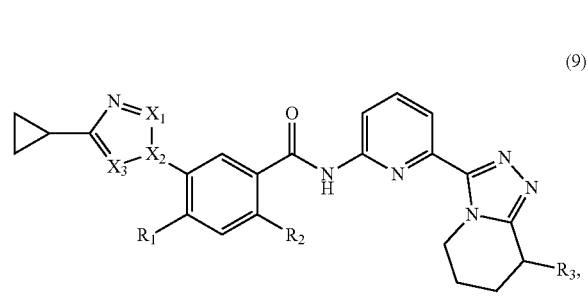

9. The compound, the pharmaceutically acceptable salt thereof or the tautomer thereof according to claim 1 is selected from the group consisting of (8)

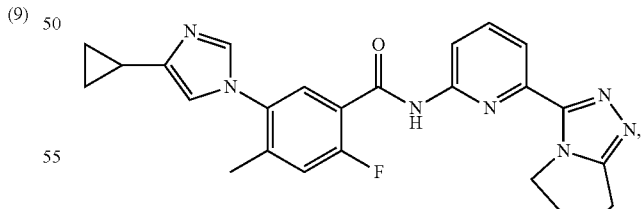

(9)

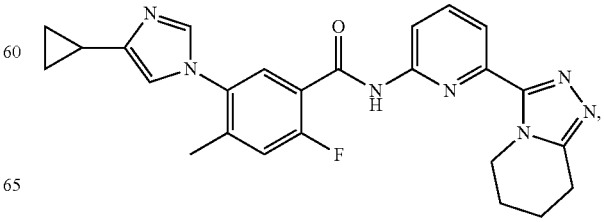

wherein, $X_1$, $X_2$, $X_3$, $R_2$ and $R_3$ are defined as claim 1;

$R_1$ is defined as claim 1.

10. The compound, the pharmaceutically acceptable salt thereof or the tautomer thereof according to claim 9, which is selected from the group consisting of (10)

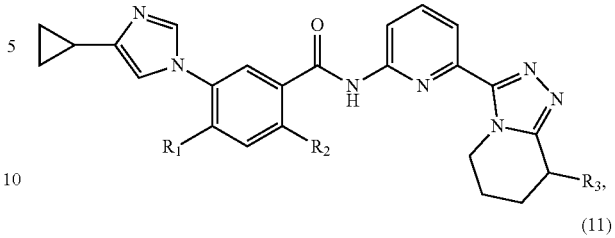

(11)

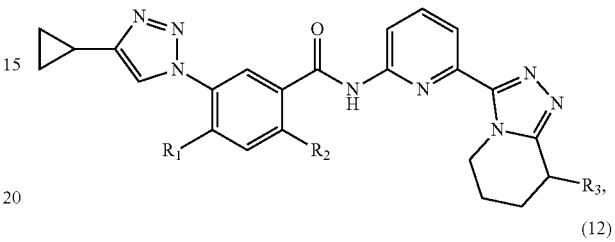

(12)

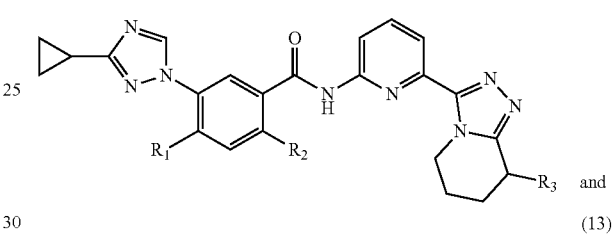

(13)

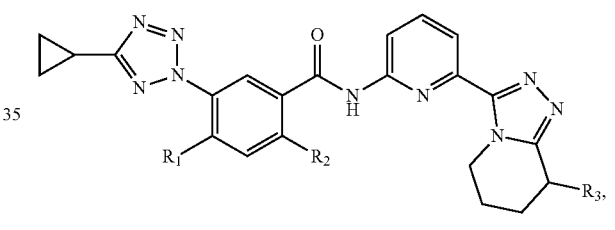

wherein, $R_2$ and $R_3$ are defined as claim 1;

$R_1$ is defined as claim 1.

11. A compound, a pharmaceutically acceptable salt thereof or a tautomer thereof which is selected from the group consisting of

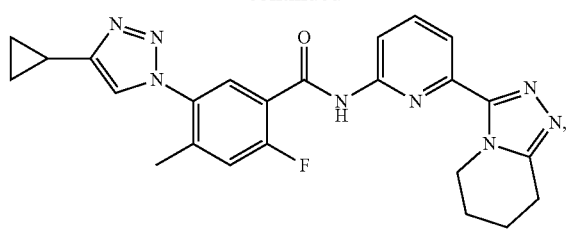
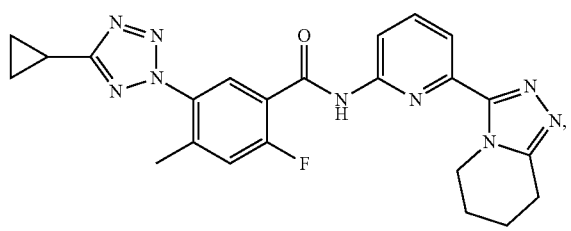
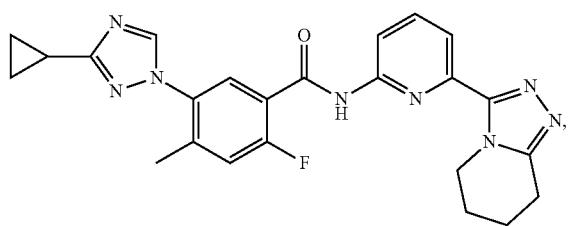
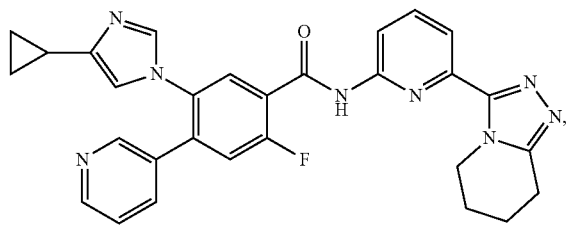
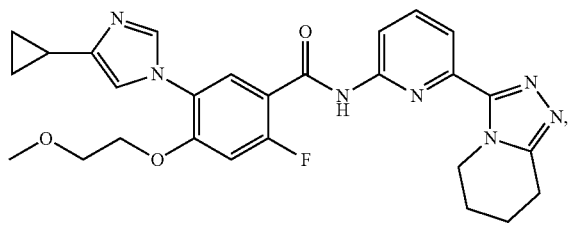
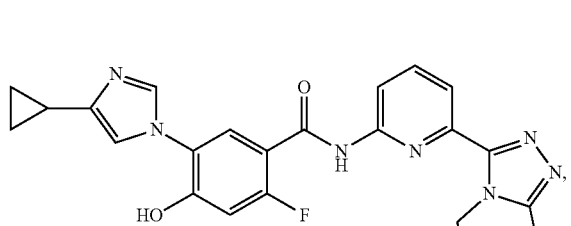
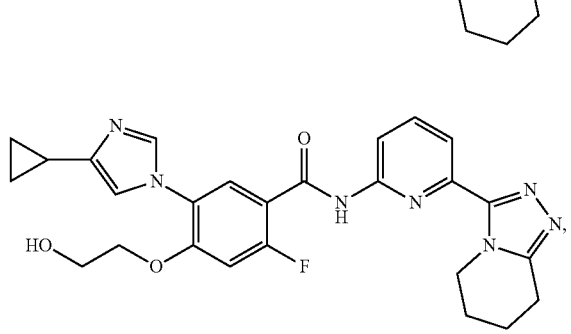
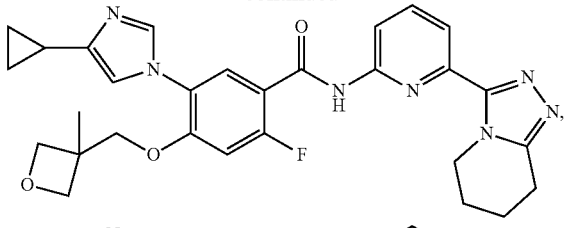
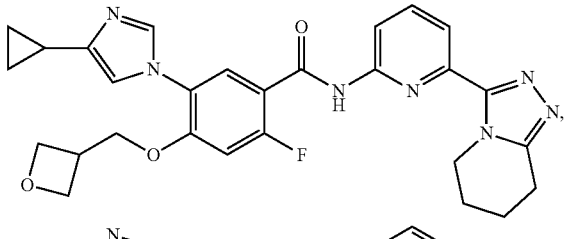
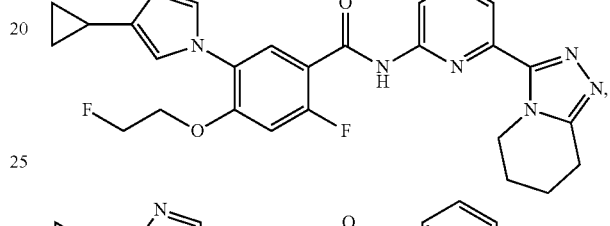
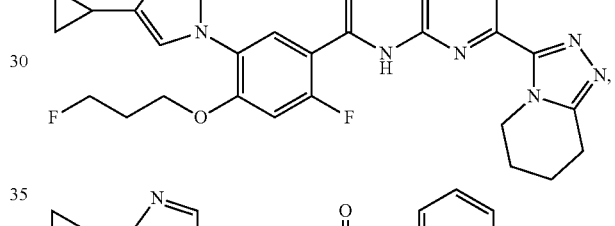
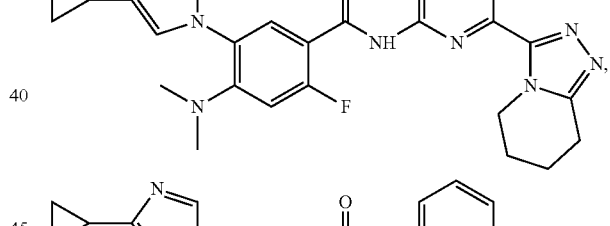
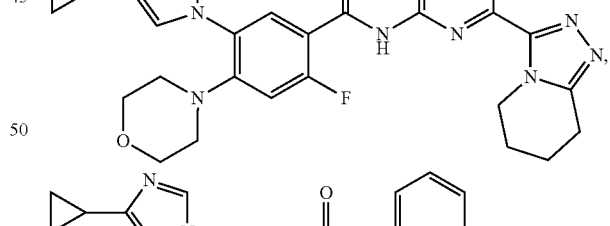
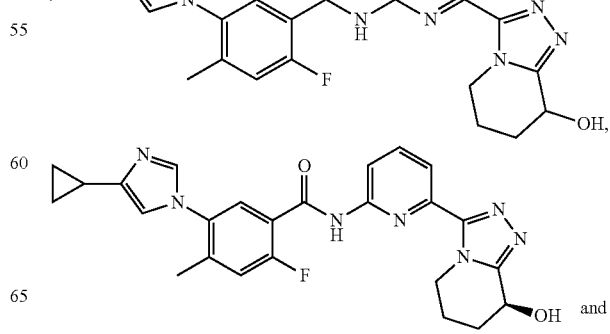

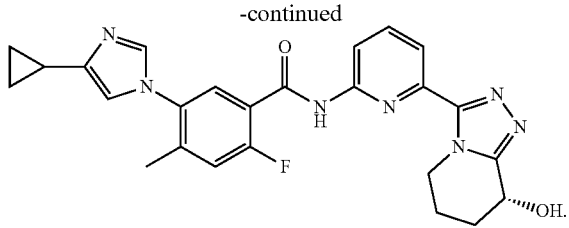

12. A pharmaceutical composition, comprising a therapeutically effective amount of the compound or the pharmaceutically acceptable salt thereof according to claim 1 as the active ingredient, and a pharmaceutically acceptable carrier.

13. A method for inhibiting ASK1 activity in a subject in need thereof, comprising: administering an effective amount of the compound or the pharmaceutically acceptable salt thereof according to claim 1.

14. A method for inhibiting ASK1 activity in a subject in need thereof, comprising: administering an effective amount of the composition according to claim 12.

15. A method for inhibiting ASK1 activity in a subject in need thereof, comprising: administering an effective amount of the compound or the pharmaceutically acceptable salt thereof according to claim 11.

16. A method for treating ASK1-related disease in a subject in need thereof, comprising: administering an effective amount of the compound or the pharmaceutically acceptable salt thereof according to claim 1 to the subject, wherein the ASK1-related disease is COPD.

17. A method for treating ASK1-related disease in a subject in need thereof, comprising: administering an effective amount of the composition according to claim 12 to the subject, wherein the ASK1-related disease is COPD.

18. A method for treating ASK1-related disease in a subject in need thereof, comprising: administering an effective amount of the compound or the pharmaceutically acceptable salt thereof according to claim 11 to the subject, wherein the ASK1-related disease is COPD.

* * * * *